United States Patent
Dymock et al.

(10) Patent No.: US 7,820,658 B2
(45) Date of Patent: Oct. 26, 2010

(54) SUBSTITUTED THIENO[2,3-D]PYRIMIDINES AS HSP90 INHIBITORS

(75) Inventors: Brian William Dymock, Abingdon (GB); Martin James Drysdale, Abington (GB); Christofe Fromont, Abington (GB); Allan Jordan, Abington (GB); Xavier Barril-Alonso, c/o Vernalis (Cambridge) Limited, Granta Park, Abington, Cambridge CB1 6GB (GB)

(73) Assignees: Vernalis (Cambridge) Limited (GB); Cancer Research Technology Ltd. (GB); Institute Of Cancer Research (GB); Xavier Barril-Alonso (GB)

( * ) Notice: Subject to any disclaimer, the term of this patent is extended or adjusted under 35 U.S.C. 154(b) by 622 days.

(21) Appl. No.: 10/569,287

(22) PCT Filed: Aug. 26, 2004

(86) PCT No.: PCT/GB2004/003641

§ 371 (c)(1),
(2), (4) Date: Oct. 6, 2006

(87) PCT Pub. No.: WO2005/021552

PCT Pub. Date: Mar. 10, 2005

(65) Prior Publication Data

US 2007/0043044 A1    Feb. 22, 2007

(30) Foreign Application Priority Data

Aug. 29, 2003  (GB) .................................. 0320300.7
Dec. 2, 2003   (GB) .................................. 0327924.7
Jun. 29, 2004  (GB) .................................. 0414467.1

(51) Int. Cl.
| | |
|---|---|
| C07D 487/04 | (2006.01) |
| A61K 31/519 | (2006.01) |
| C07D 295/04 | (2006.01) |
| C07D 295/104 | (2006.01) |
| A61K 31/5377 | (2006.01) |
| A61K 31/497 | (2006.01) |
| A61P 25/28 | (2006.01) |

(52) U.S. Cl. ............................. 514/234.2; 514/252.16; 514/260.1; 544/117; 544/278

(58) Field of Classification Search .............. 514/260.1, 514/252.16, 234.2; 544/278, 117
See application file for complete search history.

(56) References Cited

FOREIGN PATENT DOCUMENTS

| | | |
|---|---|---|
| EP | 0 438 261 A | 7/1991 |
| WO | WO 03/037860 A | 5/2003 |

OTHER PUBLICATIONS

Vippagunta et al. (Advanced Drug Delivery Reviews, 2001, 48, pp. 3-26).*
Palmer (Trends in Pharmacological Sciences, 2002, 23, pp. 426-433).*
Journal of Heterocyclic Chemistry, vol. 30, No. 4, 1994, pp. 1065-1072, XP002312253, compound12 on p. 1065, 5g on p. 1066.

* cited by examiner

*Primary Examiner*—James O Wilson
*Assistant Examiner*—Susanna Moore
(74) *Attorney, Agent, or Firm*—Banner & Witcoff, Ltd.

(57) ABSTRACT

Compounds of formula (1) are inhibitors of HSP90 activity in vitro or in vivo, and of use in the treatment of inter alia, Cancer: wherein $R_2$ is a group of formula $-(Ar^1)_m$-$(Alk^1)_p$-$(Z)_r$-$(Alk\ 2)_S$-Q wherein $Ar^1$ is an optionally substituted aryl or heteroaryl radical, Alk' and Alk 2 are optionally substituted divalent $C_1$-$C_3$ alkylene or $C_2$-$C_3$ alkenylene radicals, m, p, r and s are independently 0 or 1, Z is $-O-$, $-S-$, $-(C=O)-$, $-(C=S)-$, $-SO_2-$, $-C(=O)O-$, $-C(=O)NR^A-$, $-C(=S)NR^A-$, $-SO_2NR^A-$, $-NR^AC(=O)-$, $-NR^ASO_2-$ or $-NR^A-$ wherein $R^A$ is hydrogen or $C_1$-$C_6$ alkyl, and Q is hydrogen or an optionally substituted carbocyclic or heterocyclic radical; $R_3$ is hydrogen, an optional substituent, or an optionally substituted ($C_1$-$C_6$) alkyl, aryl or heteroaryl radical; and $R_4$ is a carboxylic ester, carboxamide or sulfonamide group.

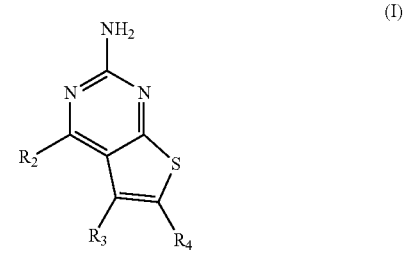

(I)

23 Claims, No Drawings

SUBSTITUTED THIENO[2,3-D]PYRIMIDINES AS HSP90 INHIBITORS

This application is a U.S. National Stage application of co-pending PCT application PCT/GB2004/003641, filed Aug. 26, 2004, which claims the priority of Great Britan Patent Application No. 0320300.7, filed Aug. 29, 2003, Great Britain Patent Application No. 0327924.7, filed Dec. 2, 2003, and Great Britain Patent Application No. 0414467.1, filed Jun. 29, 2004. These applications are incorporation herein by reference in their entireties.

This invention relates to substituted bicyclic thieno[2,3-d] pyrimidine (herein referred to as 'pyrimidothiophene') compounds having HSP90 inhibitory activity, to the use of such compounds in medicine, in relation to diseases which are responsive to inhibition of HSP90 activity such as cancers, and to pharmaceutical compositions containing such compounds.

BACKGROUND TO THE INVENTION

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, HSP90, and HSP27. Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Hunting-ton's disease), misfolded proteins can cause protein aggregation resulting in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromou and Pearl, 2000b).

Known HSP90 Inhibitors

The first class of HSP90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. 17-Allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials.

Radicicol is a macrocyclic antibiotic shown to reverse the malignant phenotype of v-Src and v-Ha-Ras transformed fibroblasts (Kwon et al, 1992; Zhao et al, 1995). It was shown to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Radicicol lacks antitumour activity in vivo due to the unstable chemical nature of the compound.

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

A purine-based HSP90 inhibitor, PU3, has been shown to result in the degradation of signalling molecules, including ERBB2, and to cause cell cycle arrest and differentiation in breast cancer cells (Chiosis et al., 2001).

Patent publications WO 2004/050087 and WO 2004/056782 relate to known classes pyrazole derivatives which are HSP90 inhibitors.

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

Brief Description of the Invention

The present invention relates to the use of a class of substituted thieno[2,3-d]pyrimidine compounds (referred to herein as pyrimidothiophenes) as HSP90 inhibitors, for example for inhibition of cancer cell proliferation. A core pyrimidothiophene ring with aromatic substitution on one ring carbon atom are principle characterising features of the compounds with which the invention is concerned.

DETAILED DESCRIPTION OF THE INVENTION

In one broad aspect the present invention provides the use of a compound of formula (I), or a salt, N-oxide, hydrate, or solvate thereof in the preparation of a composition for inhibition of HSP90 activity in vitro or in vivo:

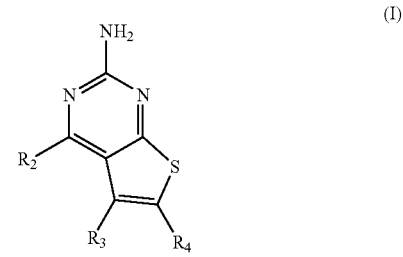

(I)

wherein
R$_2$ is a group of formula (IA):

—(Ar$^1$)$_m$-(Alk$^1$)$_p$-(Z)$_r$-(Alk$^2$)$_s$-Q    (IA)

wherein
Ar$^1$ is an optionally substituted aryl or heteroaryl radical,
Alk$^1$ and Alk$^2$ are optionally substituted divalent C$_1$-C$_3$ alkylene or C$_2$-C$_3$ alkenylene radicals,
m, p, r and s are independently 0 or 1,
Z is —O—, —S—, —(C═O)—, —(C═S)—, —SO$_2$—, —C(═O)O—, —C(═O)NR$^4$—, —C(═S)NR$^4$—, —SO$_2$NR$^4$—, —NR$^4$C(═O)—, —NR$^4$SO$_2$— or —NR$^4$— wherein R$^4$ is hydrogen or C$_1$-C$_6$ alkyl, and
Q is hydrogen or an optionally substituted carbocyclic or heterocyclic radical;

$R_3$ is hydrogen, an optional substituent, or an optionally substituted ($C_1$-$C_6$)alkyl, aryl or heteroaryl radical; and $R_4$ is a carboxylic ester, carboxamide or sulfonamide group.

In another broad aspect, the invention provides a method of treatment of diseases which are responsive to inhibition of HSP90 activity in mammals, which method comprises administering to the mammal an amount of a compound as defined in claim 1 effective to inhibit said HSP90 activity.

The in vivo use, and method, of the invention is applicable to the treatment of diseases in which HSP90 activity is implicated, including use for immunosuppression or the treatment of viral disease, inflammatory diseases such as rheumatoid arthritis, asthma, multiple sclerosis, Type I diabetes, lupus, psoriasis and inflammatory bowel disease; cystic fibrosis angiogenesis-related disease such as diabetic retinopathy, haemangiomas, and endometriosis; or for protection of normal cells against chemotherapy-induced toxicity; or diseases where failure to undergo apoptosis is an underlying factor; or protection from hypoxia-ischemic injury due to elevation of Hsp70 in the heart and brain; scrapie/CJD, Huntingdon's or Alzheimer's disease. Use for the treatment of cancer is especially indicated.

The publications WO 01/62233, Transition Metal Chemistry Vol. 19, 1994, pages 335-339, Journal of Heterocyclic Chemistry Vol. 30, 1993, pages 1065-1072, and Synthesis No. 5, 1983, pages 402-404, disclose specific compounds falling within formula (I) above, or relate to compound classes which encompass some compounds of formula (I). However, the majority of the compounds of formula (I) with which the above broad aspects of the invention are concerned are believed novel in their own right. The invention includes such novel compounds, and in particular compounds of formula (I), and salts, N-oxides, hydrates, or solvates thereof:

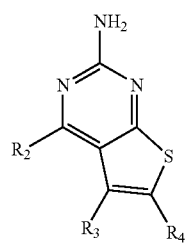

(I)

wherein $R_2$ is a group of formula (IA):

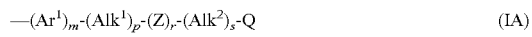

(IA)

wherein $Ar^1$ is an optionally substituted aryl or heteroaryl radical, $Alk^1$ and $Alk^2$ are optionally substituted divalent $C_1$-$C_3$ alkylene or $C_2$-$C_3$ alkenylene radicals, m, p, r and s are independently 0 or 1, Z is —O—, —S—, —(C=O)—, —(C=S)—, —SO$_2$—, —C(=O)O—, —C(=O)NR$^4$—, —C(=S)NR$^4$—, —SO$_2$NR$^4$—, —NR$^4$C(=O)—, —NR$^4$SO$_2$— or —NR$^4$— wherein R$^4$ is hydrogen or $C_1$-$C_6$ alkyl, and Q is hydrogen or an optionally substituted carbocyclic or heterocyclic radical;

$R_3$ is hydrogen, an optional substituent, or an optionally substituted ($C_1$-$C_6$)alkyl, aryl or heteroaryl radical; and $R_4$ is a carboxylic ester, carboxamide or sulfonamide group, PROVIDED THAT (i) $R_3$ is not —NH$_2$ or (ii) when $R_4$ is —COOCH$_3$ and $R_3$ is hydrogen then $R_2$ is not ethylamino, diethylamino, phenylamino or —N(Ph)(C$_2$H$_5$) wherein Ph is phenyl.

As used herein:

the term "carboxyl group" refers to a group of formula —COOH;

the term "carboxyl ester group" refers to a group of formula —COOR, wherein R is a radical actually or notionally derived from the hydroxyl compound ROH; and the term "carboxamide group" refers to a group of formula —CONR$_a$R$_b$, wherein —NR$_a$R$_b$ is an amino (including cyclic amino) group actually or notionally derived from ammonia or the amine HNR$_a$R$_b$.

the term "sulfonamide group" refers to a group of formula —SO$_2$NR$_a$R$_b$, wherein —NR$_a$R$_b$ is an amino (including cyclic amino) group actually or notionally derived from ammonia or the amine HNR$_a$R$_b$ As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" refers to a hydrocarbon chain having from a to b carbon atoms, at least one double bond, and two unsatisfied valences.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic radical whose ring atoms are all carbon, and includes monocyclic aryl, cycloalkyl, and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from $(C_1\text{-}C_6)$alkyl, $(C_1\text{-}C_6)$alkoxy, hydroxy, hydroxy$(C_1\text{-}C_6)$alkyl, mercapto, mercapto$(C_1\text{-}C_6)$alkyl, $(C_1\text{-}C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1\text{-}C_6)$alkyl group. An "optional substituent" may be one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see *Handbook of Pharmaceutical Salts: Properties. Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Also included within the scope of the invention are metabolites of compounds of formula (I), that is, compounds formed in vivo upon administration of the drug. Some examples of metabolites include
(i) where the compound of formula (I) contains a methyl group, an hydroxymethyl derivative thereof (—CH$_3$—>—CH$_2$OH):
(ii) where the compound of formula (I) contains an alkoxy group, an hydroxy derivative thereof (—OR—>—OH);
(iii) where the compound of formula (I) contains a tertiary amino group, a secondary amino derivative thereof (—NR$^1$R$^2$—>—NHR$^1$ or —NHR$^2$);
(iv) where the compound of formula (I) contains a secondary amino group, a primary derivative thereof (—NHR$^1$—>—NH$_2$);
(v) where the compound of formula (I) contains a phenyl moiety, a phenol derivative thereof (—Ph—>—PhOH); and
(vi) where the compound of formula (I) contains an amide group, a carboxylic acid derivative thereof (—CONH$_2$—>COOH).

The Radical R$_2$

As stated, R$_2$ is a group of formula (IA):

—(Ar$^1$)$_m$-(Alk$^1$)$_p$-(Z)$_r$-(Alk$^2$)$_s$-Q     (IA)

wherein in any compatible combination Ar$^1$ is an optionally substituted aryl or heteroaryl radical, Alk$^1$ and Alk$^2$ are optionally substituted divalent $C_1$-$C_3$ alkylene or $C_2$-$C_3$ alkenylene radicals, m, p, r and s are independently 0 or 1, Z is —O—, —S—, —(C=O)—, —(C=S)—, —SO$_2$—, —C(=O)O—, —C(=O)NR$^A$—, —C(=S)NR$^A$—, —SO$_2$NR$^A$—, —NR$^A$C(=O)—, —NR$^A$SO$_2$— or —NR$^A$— wherein R$^A$ is hydrogen or $C_1$-$C_6$ alkyl, and Q is hydrogen or an optionally substituted carbocyclic or heterocyclic radical When present in the radical R$_2$, Ar$^1$ may be, for example, a phenyl, cyclohexyl, pyridyl, morpholino, piperidinyl or piperazinyl ring. Presently it is preferred that Ar$^1$, when present, by a phenyl ring;

Alk$^1$ and Alk$^2$ may be, for example, optionally substituted divalent radicals selected from —CH$_2$, CH$_2$CH$_2$— or —CH=CH—. Optional substituents in Alk$^1$ and Alk$^2$ include, for example mono- or di($C_1$-$C_3$alkyl)amino and $C_1$-$C_3$alkoxy; and Z may be, for example, —O— or —NH—; and Q is hydrogen.

In a simple subclass of compounds with which the invention is concerned, m is 1 and each of p, r and s is 0, and Q is hydrogen, so that R$_2$ is optionally substituted aryl or heteroaryl. In such cases, R$_2$ may be, for example, optionally substituted phenyl, 2- or 3-thienyl, 2- or 3-furanyl, 2-, 3- or 4-pyridinyl, morpholinyl, or piperidinyl. Currently preferred are compounds wherein R$_2$ is optionally substituted phenyl, for example where the optional substituents are selected from methyl, ethyl, n- or isopropyl, vinyl, allyl, methoxy, ethoxy, n-propyloxy, benzyloxy, allyloxy, cyanomethoxy chloro, bromo, cyano, formyl, methyl-, ethyl-, or n-propyl-carbonyloxy, methyl- or ethylaminocarbonyl. More complex substituent groups which may be present in the R$_2$ ring include those (i) of formula —O(CH$_2$)$_n$Z$^1$ wherein n is 1, 2 or 3 and Z$^1$ is a primary, secondary, tertiary or cyclic amino group, or a $C_1$-$C_6$alkoxy group; or (ii) of formula -(Alk$^3$)$_m$Z$^1$ wherein Alk$^3$ is a divalent straight or branched chain ($C_1$-$C_3$) alkylene, m is 0 or 1, and Z$^1$ is a primary, secondary, tertiary or cyclic amino group, or a $C_1$-$C_6$alkoxy group. Preferred substitution positions in the phenyl ring are positions 2, 4 and 5.

In other simple structures, m is 1, p, r and s are again each 0, and Q may be an optionally substituted carbocyclic or heterocyclic ring, for example phenyl, cyclohexyl, pyridyl, morpholino, piperidinyl, or piperazinyl ring. In such cases, Q is a direct substituent in the optionally substituted Ar$^1$ ring.

In more complex structures with which the invention is concerned, one or more of m, p, r and s may be 1, and Q may be hydrogen or an optionally substituted carbocyclic or heterocyclic ring. For example, p and/or s may be 1 and r may be 0, so that Q is linked to Ar$^1$ by an alkylene or alkenylene radical, for example a $C_1$-$C_3$ alkylene radical, which is optionally substituted. In other cases each of p, r, and s may be 1, in which cases, Q is linked to Ar$^1$ by an alkylene or alkenylene radical which is interrupted by the hetero atom-containing Z radical. In still other cases, p and s may be 0 and r may be 1, in which case Q is linked to Ar$^1$ via the hetero atom-containing Z radical.

Specific examples of R$_2$ groups usable in compounds of the invention include those present in the compounds of the Examples herein.

The Optional Substituent R$_3$

R$_3$ is hydrogen or an optional substituent, as defined above. Presently it is preferred that R$_3$ be hydrogen.

The Group R$_4$

When R$_4$ is a carboxamide or sulfonamide group, examples include those of formula —CONR$^B$(Alk)$_n$R$^A$ or —SO$_2$NR$^B$(Alk)$_n$R$^A$ wherein Alk is a divalent alkylene, alkenylene or alkynylene radical, for example a —CH$_2$—, —CH$_2$CH$_2$—, —CH$_2$CH$_2$CH$_2$—, —CH$_2$CH=CH—, or —CH$_2$CCCH$_2$-radical, and the Alk radical may be optionally substituted, n is 0 or 1, R$^B$ is hydrogen or a $C_1$-$C_6$ alkyl or $C_2$-$C_6$ alkenyl group, for example methyl, ethyl, n- or iso-propyl, or allyl, Currently it is preferred that R$^B$ be hydrogen.

R$^A$ is an optional substituent such as hydroxyl, amino (including mono- and di-($C_1$-$C_3$)alkylamino), carbamoyl (—C(=O)NH$_2$), —SO$_2$OH, trifluoromethyl; or optionally substituted carbocyclic, for example cyclopropyl, cyclopentyl, cyclohexyl, phenyl optionally substituted by hydroxyl, amino, fluoro, chloro, bromo, 3,4 methylenedioxy, sulfamoyl (—SO$_2$NH$_2$), —SO$_2$OH, methoxy, methylsulfonyl, trifuoromethyl; or heterocyclyl, for example pyridyl, furyl, thienyl, diazolyl, N-piperazinyl, pyrrolyl, tetrahydrofuranyl, thiazolyl, 1-aza-bicyclo[2,2,2]octanyl, or N-morpholinyl any of which heterocyclic rings may be substituted, for example on a ring nitrogen by ($C_1$-$C_3$)alkyl, or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms, examples of such N-heterocyclic rings including morpholino, piperidinyl, piperazinyl and N-phenylpiperazinyl.

Presently it is preferred that R$_4$ be a corboxamide group.

When R$_4$ is a carboxylic ester group, examples include those of formula —COOR$^C$ wherein R$^C$ is a $C_1$-$C_6$ alkyl or $C_2$-$C_6$ alkenyl group, for example methyl, ethyl, n- or iso-propyl, or allyl; or an optionally substituted aryl or heteroaryl group, for example optionally substituted phenyl, pyridyl or thiazolyl; or an optionally substituted aryl($C_1$-$C_6$ alkyl)- or heteroaryl($C_1$-$C_6$ alkyl)- group such as benzyl or pyridylmethyl; or an optionally substituted cycloalkyl group such as cyclopentyl or cyclohexyl.

Specific examples of R$_4$ groups usable in compounds of the invention include those present in the compounds of the Examples herein.

A preferred subclass of the compounds with which the invention is concerned has formula (II)

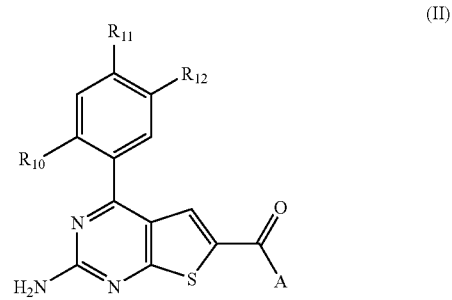

(II)

wherein

A is a secondary amino group

R$_{10}$ is H, Cl, Br, or CH$_3$;

R$_{11}$ is hydrogen, Cl, Br, CN, methyl, ethyl, n- or iso-propyl, vinyl or allyl;

R$_{12}$ is (i) a radical of formula —O(CH$_2$)$_n$Z$^1$ wherein n is 1, 2 or 3 and Z$^1$ is a primary, secondary, tertiary or cyclic amino group, or a $C_1$-$C_6$alkoxy group; or (ii) a radical of formula -(Alk$^3$)$_m$Z$^1$ wherein Alk$^3$ is a divalent straight or branched chain ($C_1$-$C_3$) alkylene, m is 0 or 1, and Z$^1$ is a primary, secondary, tertiary or cyclic amino group, or a $C_1$-$C_6$alkoxy group. In this subclass of compounds (II) it is preferred that A is a secondary $C_1$-$C_6$alkylamino group, for example wherein the $C_1$-$C_6$alkyl substituent is selected from methyl, ethyl, and n- and iso-propyl, and R$_{12}$ is (i) a radical of formula —O(CH$_2$)$_n$Z$^1$ wherein n is 1, 2 or 3 and Z$^1$ is di($C_1$-$C_3$alkyl)amino or $C_1$-$C_3$alkoxy, for example wherein the $C_1$-$C_3$alkyl component(s) is/are selected from methyl, ethyl, and n- and iso-propyl.

Specific compounds with which the invention is concerned include those of the Examples, particularly those exemplified compounds which have structure (II) above.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*". Such literature methods include those of the preparative Examples herein, and methods analogous thereto.

For example the following general reaction scheme can be employed:

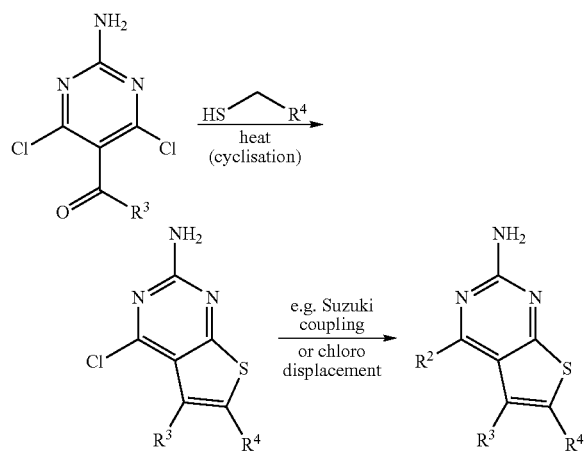

Starting material are either available commercially or can be made according to literature methods. Subsequent reactions may be carried out on $R^2$, $R^3$ or $R^4$ to prepare additional compounds of formula (I)

The compounds of the invention are inhibitors of HSP90 and are useful in the treatment of diseases which are responsive to inhibition of HSP90 activity such as cancers; viral diseases such as Hepatitis C(HCV) (Waxman, 2002); Immunosupression such as in transplantation (Bijimakers, 2000 and Yorgin, 2000); Anti-inflammatory diseases (Bucci, 2000) such as Rheumatoid arthritis, Asthma, MS, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis. Also an Hsp90 inhibitor of the invention may protect normal cells against chemotherapy-induced toxicity and be useful in diseases where failure to undergo apoptosis is an underlying factor. Such an Hsp90 inhibitor may also be useful in diseases where the induction of a cell stress or heat shock protein response could be beneficial, for example, protection from hypoxia-ischemic injury due to elevation of Hsp70 in the heart (Hutter, 1996 and Trost, 1998) and brain (Plumier, 1997 and Rajder, 2000). An Hsp90 inhibitor—induced increase in Hsp70 levels could also be useful in diseases where protein misfolding or aggregation is a major causal factor, for example, neurogenerative disorders such as scrapie/CJD, Huntingdon's and Alzheimer's (Sittler, 2001; Trazelt, 1995 and Winklhofer, 2001)".

Accordingly, the invention also includes:
(i) A pharmaceutical or veterinary composition comprising a compound of formula (I) above, together with a pharmaceutically or veterinarily acceptable carrier.
(ii) The use of a compound a compound of formula (I) above in the preparation of a composition for composition for inhibition of HSP90 activity in vitro or in vivo.
(iii). A method of treatment of diseases or conditions which are responsive to inhibition of HSP90 activity in mammals which method comprises administering to the mammal an amount of a compound of formula (I) above effective to inhibit said HSP90 activity.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation and activities of specific compounds of the invention.

EXAMPLE 1

2-Amino-4-phenyl-thieno[2,3-d]pyrimidine-6-carboxylic acid ethyl ester

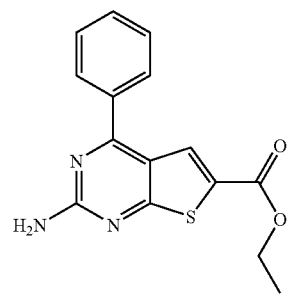

Step 1

2-Amino-4-chloro-thieno[2,3-d]pyrimidine-6-carboxylic acid ethyl ester

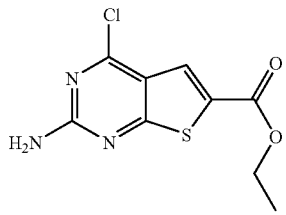

To a stirred mixture of 2-amino-4,6-dichloro-5-formyl-pyrimidine (1 eq.) and potassium carbonate (1 eq.) in acetonitrile at ambient temperature was added ethyl-2-mercaptoacetate (0.95 eq.) and the mixture stirred at ambient temperature for three hours, followed by heating at 80° C. for one hour. After cooling, the mixture was concentrated to dryness in vacuo. Column chromatography on silica, eluting with ethyl acetate and hexanes, gave example 1 as a yellow powder.

LC-MS retention time: 2.371 minutes, [M+H]+ 258.0

Step 2 (Suzuki Reaction):

2-Amino-4-phenyl-thieno[2,3-d]pyrimidine-6-carboxylic acid ethyl ester

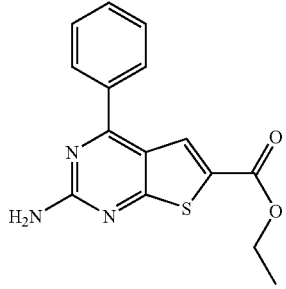

A solution of example 1 step 1 (1 eq.), phenyl boronic acid (1.2 eq) and sodium carbonate (1.2 eq) in 1,4-dioxane and water (3.5:1) were degassed by bubbling though nitrogen gas for 5 mins. Pd(PPh$_3$)$_4$ (0.05 eq.) was added and the mixture heated in a Personal Chemistry Synthesiser microwave at 150° C. for 10 minutes. After cooling and concentration in vacuo, perparative HPLC gave example 2 as a white powder.

LC-MS retention time: 2.545 minutes, [M+H]+ 300.10

This compound had activity 'A' in the fluorescence polarization assay described below.

EXAMPLE 2

2-Amino-4-(4-trifluoromethyl-phenyl)-thieno[2,3-d]pyrimidine-6-carboxylic acid ethyl ester

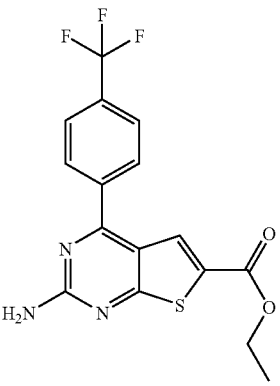

prepared as for Example 1.

LC-MS retention time: 2.768 minutes, [M+H]+ 368.1

$^1$H NMR (400 MHz, d6-DMSO): δ=1.07 (3H, t, J=7.1 Hz), 4.09 (2H, q, J=7.1 Hz), 7.25 (2H, br s), 7.68 (1H, s), 7.76 (2H, d, J=8.0 Hz), 7.85 (2H, d, J=8.0 Hz).

This compound had activity 'B' in the fluorescence polarization assay described below.

The following compounds in Table 1 were synthesised and tested in the fluorescence polarization assay described below. Suzuki reactions were carried out as in Example 1 Step 2. Reductive amination reactions were carried out as for Example 33, as follows:

2-Amino-4-(4-piperidin-1-ylmethyl-phenyl)-thieno[2,3-d]pyrimidine-6-carboxylic acid ethyl ester (Example 33 in Table 1)

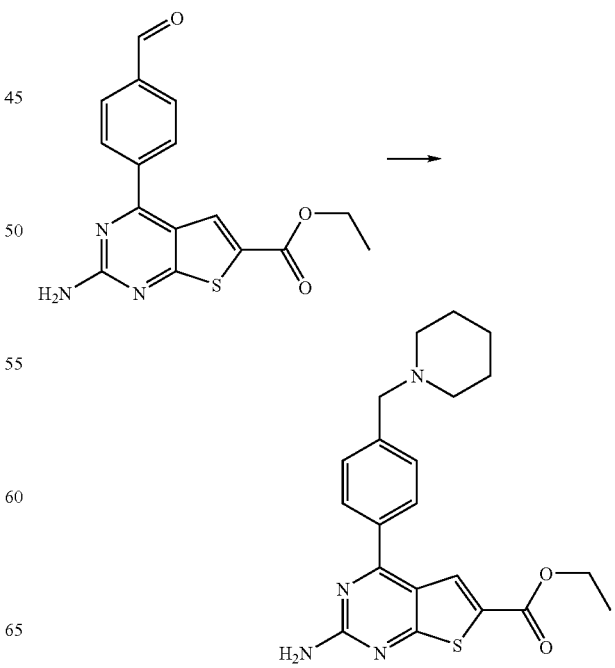

Pyrrolidine (5 equiv) was added to a suspension of 2-amino-4-(4-formyl-phenyl)-thieno[2,3-d]pyrimidine-6-carboxylic acid ethyl ester (1 equiv) in methanol. Reaction mixture was heated to reflux for 3.5 hours then cooled to room temperature. Sodium borohydride (3 equiv) was added and stirred for 10 mins. The mixture was concentrated in vacuo then partitioned between ethyl acetate and water. The phases were separated and the organic layer was washed with brine, dried and evaporated to a yellow oil. The crude product was purified by preparative HPLC.

LC-MS retention time: 1.803 minutes, $[M+H]^+$ 383.

Chloride displacement reactions were carried out as for Example 22 as follows:

2-Amino-4-benzylamino-thieno[2,3-d]pyrimidine-6-carboxylic acid methyl ester (Example 22 in Table 1)

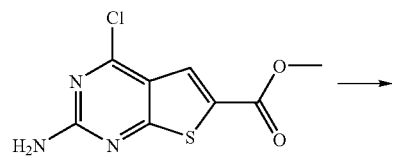

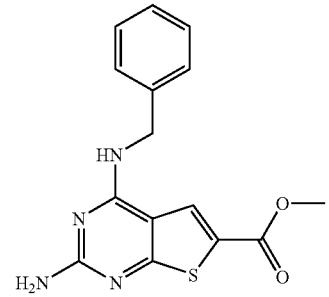

The 2-amino-4-chloro-thieno[2,3-d]pyrimidine-6-carboxylic acid methyl ester (100 mg, 0.39 mmol), benzylamine (100 µL) in 4 mL of THF are submitted to MW irradiation at 110° C. for 35 mins. The reaction was cooled to room temperature and worked up (acidic) and purified using standard conditions for a neutral compound.

LC-MS: RT=2.391 mins; MS m/z=329 (M+1).

Note: Intensity and reaction time depends on reactivity of amine. For example, for less reactive amines (such as N-methyl aniline), suitable reaction conditions are MW 160° C. for 30 mins and 0.5 mL of amine.

The fourth column of Table 1 states the activity of the compound in the fluorescence polarization assay described below.

TABLE 1

| Example | Structure | MH+ | Hsp90 FP IC50 | Synthesis Comment |
|---|---|---|---|---|
| 3 | 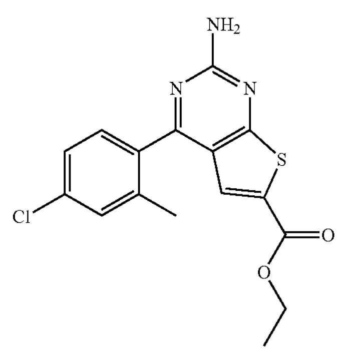 | 348 | A | Suzuki |
| 4 | 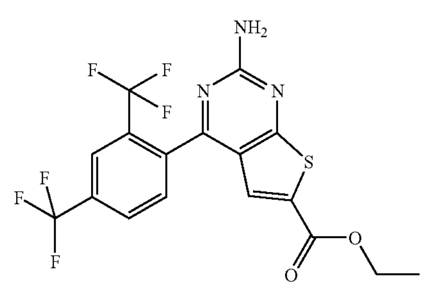 | 436 | A | Suzuki |

TABLE 1-continued

| Example | Structure | MH+ | Hsp90 FP IC50 | Synthesis Comment |
|---------|-----------|-----|---------------|-------------------|
| 5 | 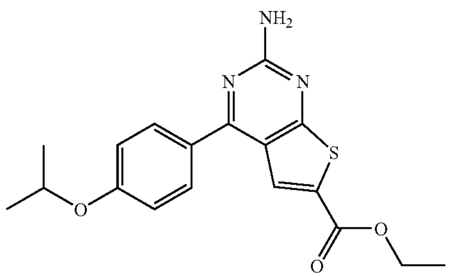 | 358 | B | Suzuki |
| 6 | 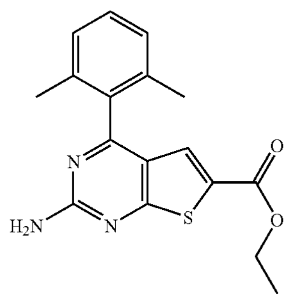 | 328 | A | Suzuki |
| 7 | 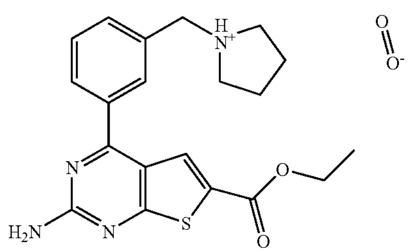 | 383 | B | reductive amination on 4-aldehyde (made by Suzuki reaction) |
| 8 | 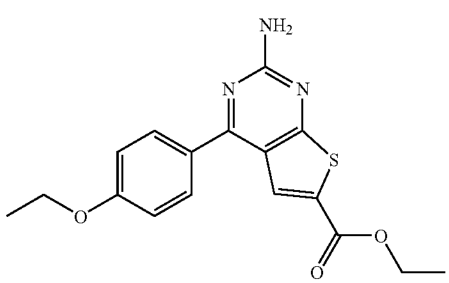 | 344 | A | Suzuki |
| 9 | 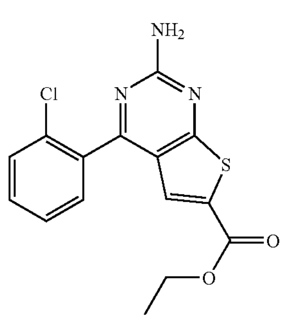 | 334 | A | Suzuki |

TABLE 1-continued

| Example | Structure | MH+ | Hsp90 FP IC50 | Synthesis Comment |
|---------|-----------|-----|---------------|-------------------|
| 10 | 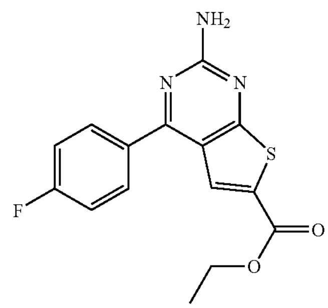 | 318 | B | Suzuki |
| 11 | 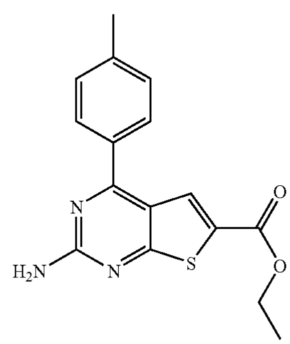 | 314 | A | Suzuki |
| 12 | 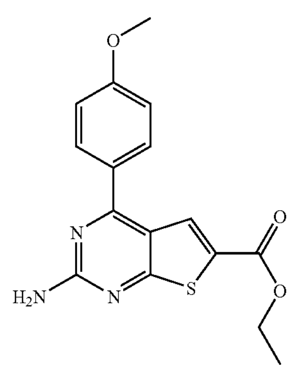 | 330 | B | Suzuki |
| 13 | 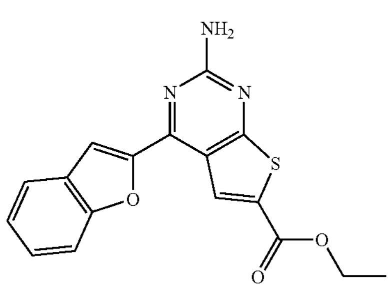 | 340 | B | Suzuki |

TABLE 1-continued

| Example | Structure | MH+ | Hsp90 FP IC50 | Synthesis Comment |
|---------|-----------|-----|---------------|-------------------|
| 14 | 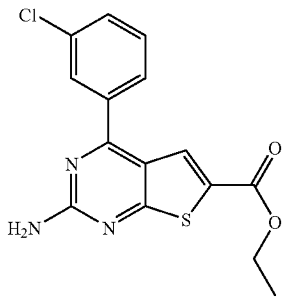 | 334 | B | Suzuki |
| 15 | 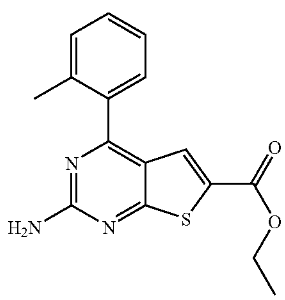 | 314 | A | Suzuki |
| 16 | 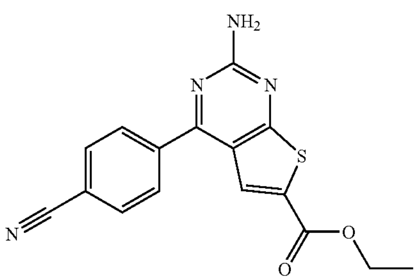 | 325 | A | Suzuki |
| 17 | 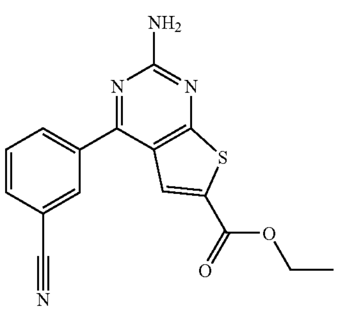 | 325 | B | Suzuki |
| 18 | 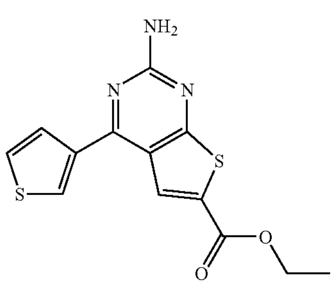 | 306 | B | Suzuki |

TABLE 1-continued

| Example | Structure | MH+ | Hsp90 FP IC50 | Synthesis Comment |
| --- | --- | --- | --- | --- |
| 19 | 4-phenoxy-2-amino-thieno[2,3-d]pyrimidine-6-carboxylic acid ethyl ester | 316 | B | chloride displacement |
| 20 | 4-(ethoxycarbonylmethylthio)-2-amino-thieno[2,3-d]pyrimidine-6-carboxylic acid ethyl ester | 342 | B | chloride displacement |
| 21 | 4-phenylamino-2-amino-thieno[2,3-d]pyrimidine-6-carboxylic acid methyl ester | 301 | B | chloride displacement |
| 22 | 4-benzylamino-2-amino-thieno[2,3-d]pyrimidine-6-carboxylic acid methyl ester | 315 | B | chloride displacement |
| 23 | 4-(N-methyl-N-benzylamino)-2-amino-thieno[2,3-d]pyrimidine-6-carboxylic acid methyl ester | 329 | B | chloride displacement |

TABLE 1-continued

| Example | Structure | MH+ | Hsp90 FP IC50 | Synthesis Comment |
|---------|-----------|-----|---------------|-------------------|
| 24 | 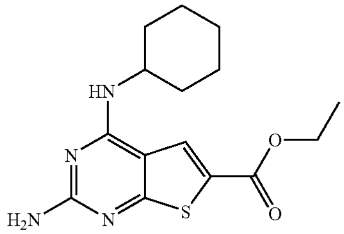 | 321 | B | chloride displacement |
| 25 | 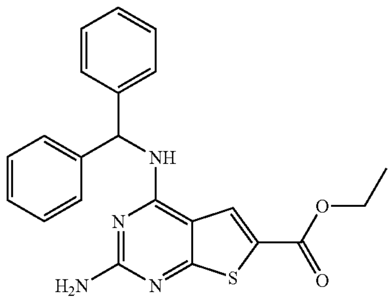 | 405 | B | chloride displacement |
| 26 | 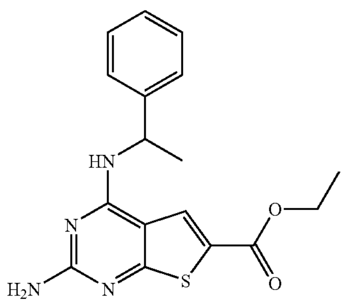 | 343 | B | chloride displacement |
| 27 | 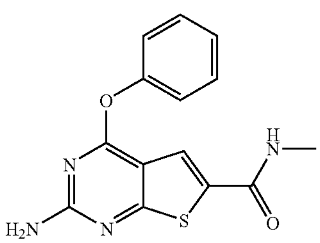 | 301 | B | chloride displacement |
| 28 | 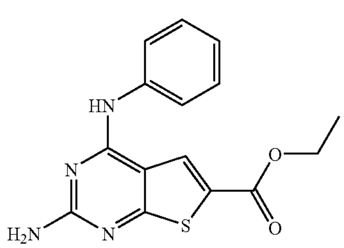 | 315 | B | chloride displacement |

TABLE 1-continued

| Example | Structure | MH+ | Hsp90 FP IC50 | Synthesis Comment |
|---------|-----------|-----|---------------|-------------------|
| 29 | 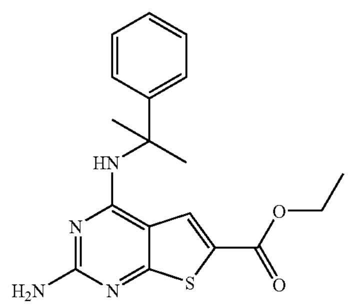 | 357 | B | chloride displacement |
| 30 | 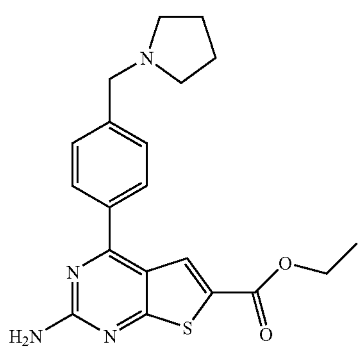 | 383 | B | reductive amination on 4-aldehyde (made by Suzuki reaction) |
| 31 | 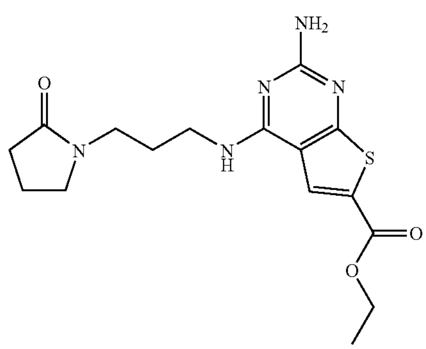 | 364 | B | chloride displacement |
| 32 | 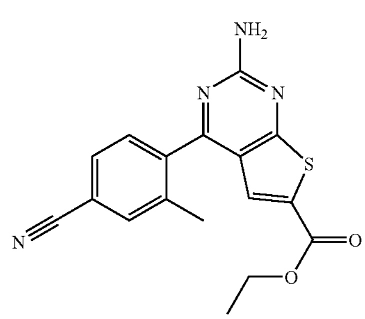 | 339 | A | Suzuki |

TABLE 1-continued

| Example | Structure | MH+ | Hsp90 FP IC50 | Synthesis Comment |
|---------|-----------|-----|---------------|-------------------|
| 33 | 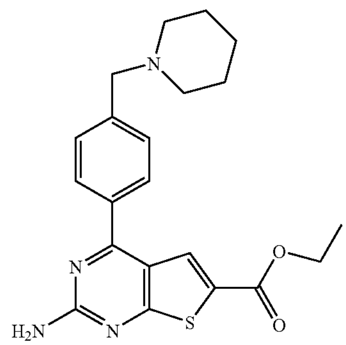 | 397 | B | reductive amination on 4-aldehyde (made by Suzuki reaction) |
| 34 | 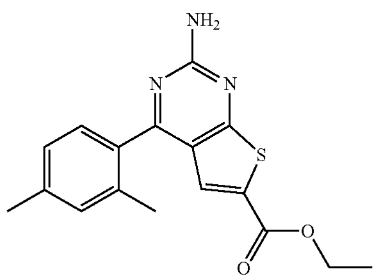 | 328 | A | Suzuki |
| 35 | 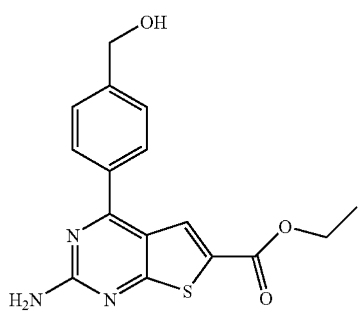 | 330 | A | reductive of 4-aldehyde (made by Suzuki reaction) |
| 36 | 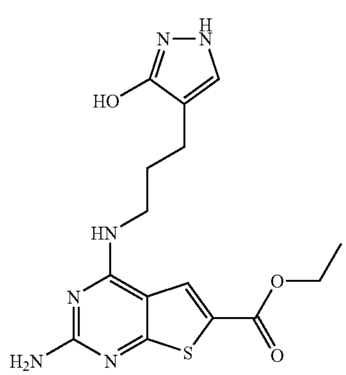 | 363 | B | chloride displacement |

TABLE 1-continued

| Example | Structure | MH+ | Hsp90 FP IC50 | Synthesis Comment |
|---------|-----------|-----|---------------|-------------------|
| 37 | 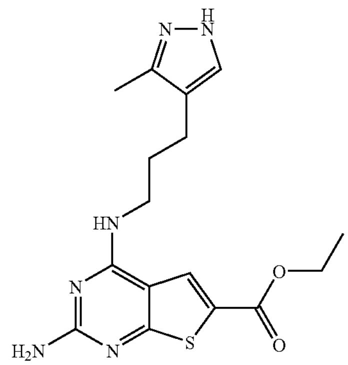 | 361 | B | chloride displacement |
| 38 | 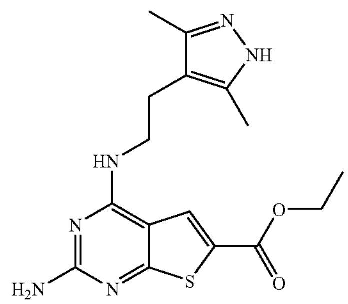 | 355 | B | chloride displacement |
| 39 | 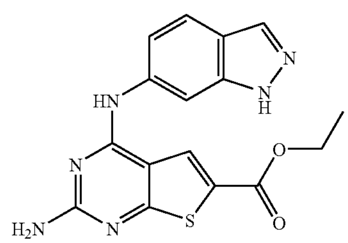 | 355 | B | chloride displacement |
| 40 | 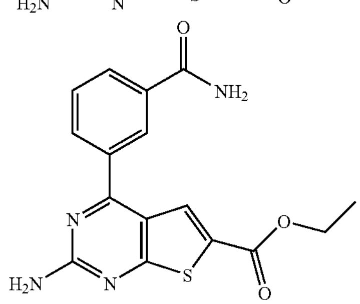 | 343 | B | Suzuki |
| 41 | 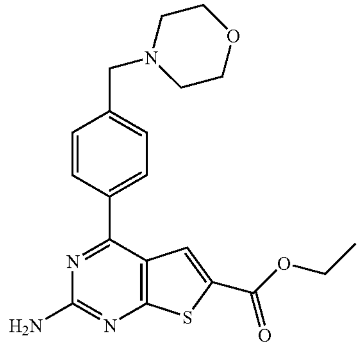 | 399 | B | reductive amination on 4-aldehyde (made by Suzuki reaction) |

EXAMPLE 42

2-Amino-4-phenyl-thieno[2,3-d]pyrimidine-6-carboxylic acid amide

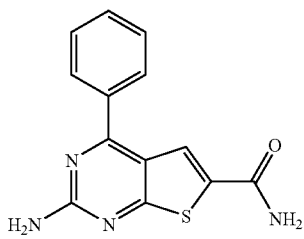

The compound of example 1 was suspended in concentrated ammonium hydroxide and heated in a Personal Chemistry Synthesiser microwave at 140° C. for 20 minutes. Concentration in vacuo gave example 42 as a white solid.

LC-MS retention time: 1.824 minutes, [M+H]$^+$ 271.10

EXAMPLE 43

2-Amino-4-phenyl-thieno[2,3-d]pyrimidine-6-carboxylic acid ethylamide

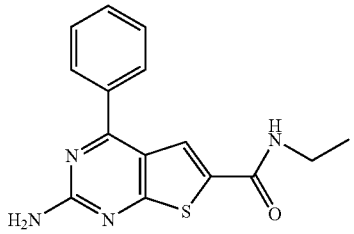

Step 1

2-Amino-4-phenyl-thieno[2,3-d]pyrimidine-6-carboxylic acid

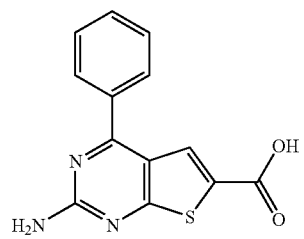

Sodium Hydroxide (0.66 g; 16.5 mmol) was added to a suspension of 2-amino-4-phenyl-thieno[2,3-d]pyrimidine-6-carboxylic acid ethyl ester (Example 1) (1.00 g; 3.34 mmol) in ethanol (20 ml) and water (2 ml). The mixture was heated at reflux for 1 hour (affording a homogeneous pale-yellow solution) and allowed to cool to ambient temperature. Solvents were removed in vacuo and the solid residue was dissolved in water (30 mL) and cooled with ice-water bath. The mixture was stirred and adjusted to pH 1-2 by drop-wise addition of concentrated Hydrochloric acid. The resulting precipitate was filtered, washed with water, then ethanol and finally diethyl ether. The off-white product was dried in vacuo to afford 2-amino-4-phenyl-thieno[2,3-d]pyrimidine-6-carboxylic acid as a colourless solid (0.784 g; 87%).

LC/MS RT=1.845 min; m/z=272 (M+H)+

Step 2

2-Amino-4-phenyl-thieno[2,3-d]pyrimidine-6-carboxylic acid ethylamide

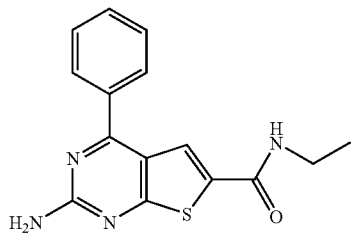

O-(7-Azabenzotriazol-1-yl)-N,N,N',N'-tetramethyluronium hexafluorophosphate (0.380 g, 1.0 mmol) was added to 2-amino-4-phenyl-thieno[2,3-d]pyrimidine-6-carboxylic acid (0.187 g, 0.69 mmol). This mixture was suspended in dimethylformamide (DMF) (5.0 ml) and diisopropylethylamine (0.696 ml; 4.0 mmol) added to afford a yellow solution. Diethylamine hydrochloride (0.122 g; 5.0 mmol) was added and the reaction mixture was heated for ten minutes at 100° C. in a sealed vial in a microwave synthesiser. DMF was removed in vacuo and the residue was partitioned between ethyl acetate (30 ml) and water (30 ml). The phases were separated and the organic phase was washed with saturated sodium chloride solution and dried over sodium sulphate. Mixture was filtered and the filtrate solvents were removed in vacuo to leave a yellow solid which was adsorbed onto silica gel and purified by flash chromatography on silica gel (20 g), eluting with a solvent gradient of 15 to 50% ethyl acetate in hexane. This affords 2-amino-4-phenyl-thieno[2,3-d]pyrimidine-6-carboxylic acid ethylamide as a pale yellow solid (0.051 g; 25%).

LC/MS RT=2.08 min; m/z=299 (M+H)+ $^1$H NMR (400 MHz, d6 DMSO) δ 1.11 (t, 3H), 3.26 (m, 2H), 7.12 (s, 2H), 7.61 (m, 3H), 7.86 (m, 2H), 8.03 (s, 1H, 8.71 (t, 1H).

The compound of Example 43 had activity 'A' in the fluorescence polarization assay described below.

The following compounds (Table 2) were made by the method of Example 43 from the corresponding ester (Table 1) and the appropriate amine.

The final column of Table 2 states the activity of the compound in the fluorescence polarization assay described below.

TABLE 2

| Example | Structure | MH+ | Hsp90 FP IC50 |
|---|---|---|---|
| 44 | 2-amino-4-phenyl-N-(2-(dimethylamino)ethyl)thieno[2,3-d]pyrimidine-6-carboxamide | 342 | A |
| 45 | 2-amino-4-phenyl-N-(3-(dimethylamino)propyl)thieno[2,3-d]pyrimidine-6-carboxamide | 356 | B |
| 46 | 2-amino-4-phenyl-N-(2-morpholinoethyl)thieno[2,3-d]pyrimidine-6-carboxamide | 384 | B |
| 47 | 2-amino-4-phenyl-N-propylthieno[2,3-d]pyrimidine-6-carboxamide | 313 | A |
| 48 | 2-amino-N-butyl-4-phenylthieno[2,3-d]pyrimidine-6-carboxamide | 327 | B |
| 49 | 2-amino-4-phenyl-N-phenethylthieno[2,3-d]pyrimidine-6-carboxamide | 375 | B |

TABLE 2-continued
| Example | Structure | MH+ | Hsp90 FP IC50 |
|---|---|---|---|
| 50 | 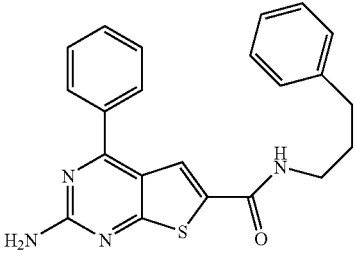 | 389 | B |
| 51 | 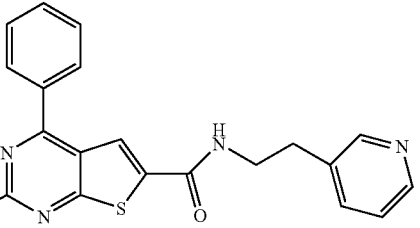 | 376 | B |
| 52 | 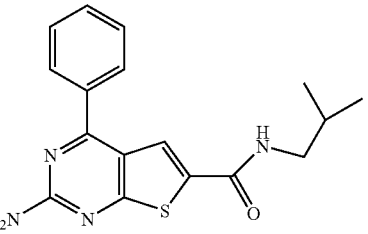 | 327 | B |
| 53 | 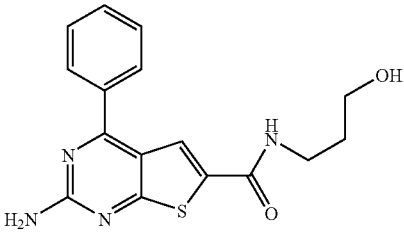 | 329 | A |
| 54 | 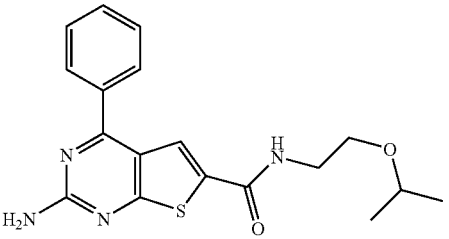 | 357 | A |
| 55 | 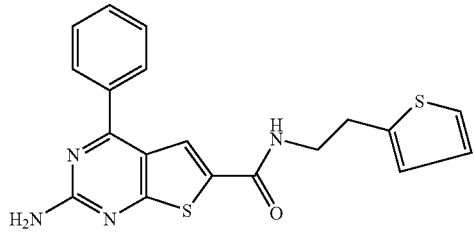 | 381 | B |

TABLE 2-continued

| Example | Structure | MH+ | Hsp90 FP IC50 |
|---|---|---|---|
| 56 | 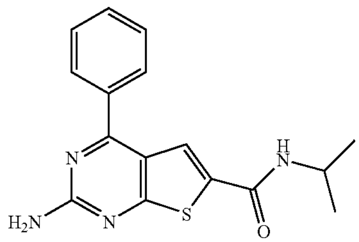 | 313 | A |
| 57 | 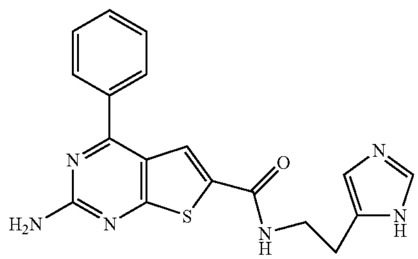 | 365 | A |
| 58 | 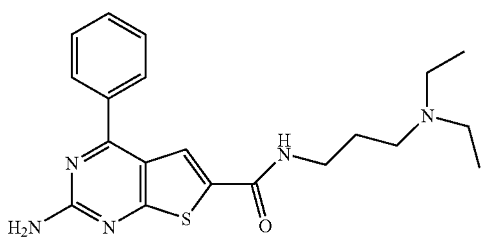 | 384 | B |
| 59 | 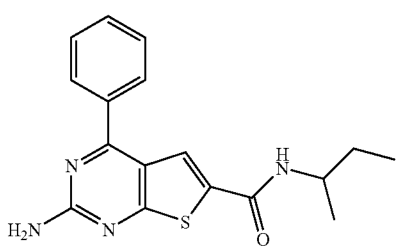 | 327 | B |
| 60 | 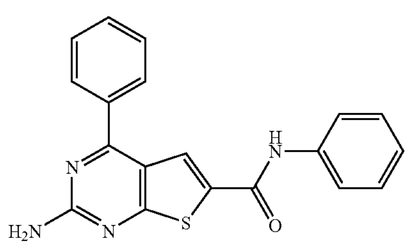 | 347 | B |

TABLE 2-continued

| Example | Structure | MH+ | Hsp90 FP IC50 |
|---|---|---|---|
| 61 | 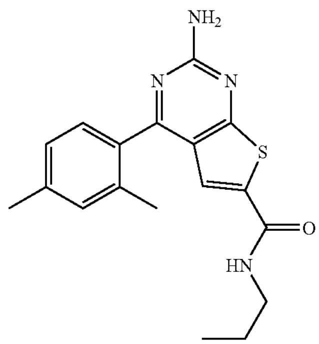 | 341 | A |
| 62 | 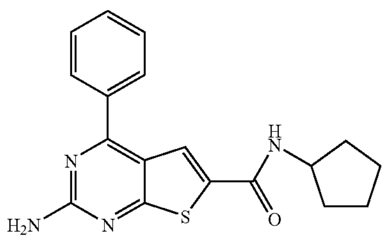 | 339 | A |
| 63 | 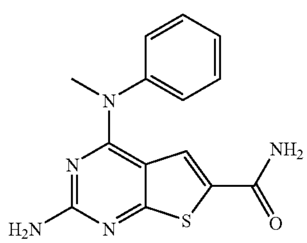 | 300 | B |
| 64 | 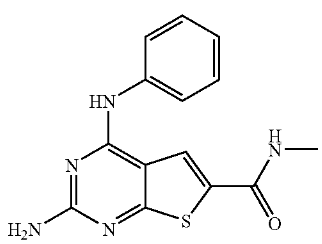 | 300 | B |
| 65 | 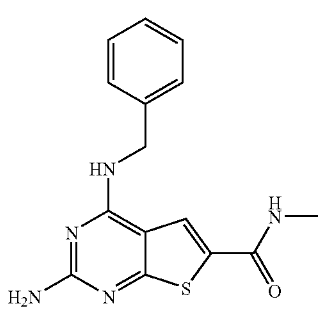 | 314 | B |

TABLE 2-continued

| Example | Structure | MH+ | Hsp90 FP IC50 |
|---|---|---|---|
| 66 | 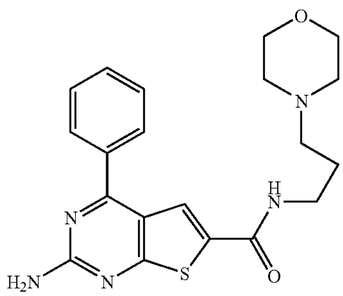 | 398 | B |
| 67 | 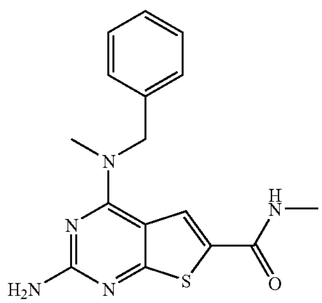 | 328 | B |
| 68 | 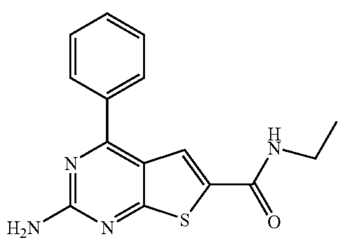 | 299 | A |
| 69 | 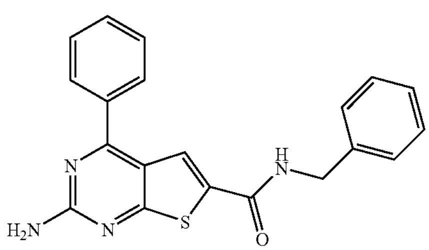 | 361 | |
| 70 | 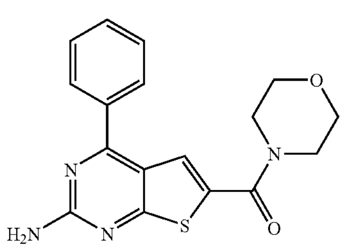 | 341 | B |

TABLE 2-continued
| Example | Structure | MH+ | Hsp90 FP IC50 |
|---|---|---|---|
| 71 | 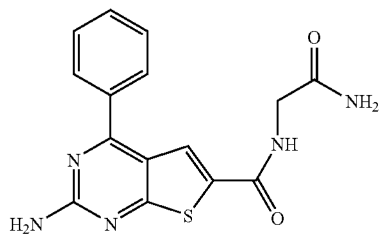 | 328 | A |
| 72 | 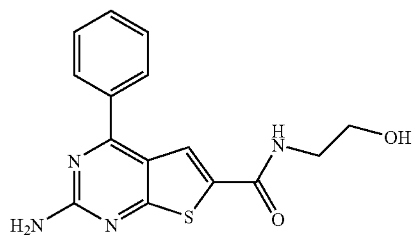 | 315 | A |
| 73 | 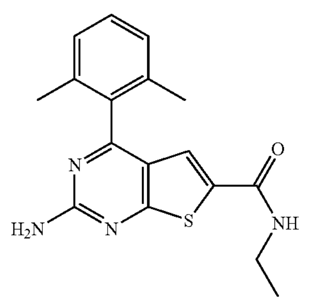 | 327 | A |
EXAMPLE 74
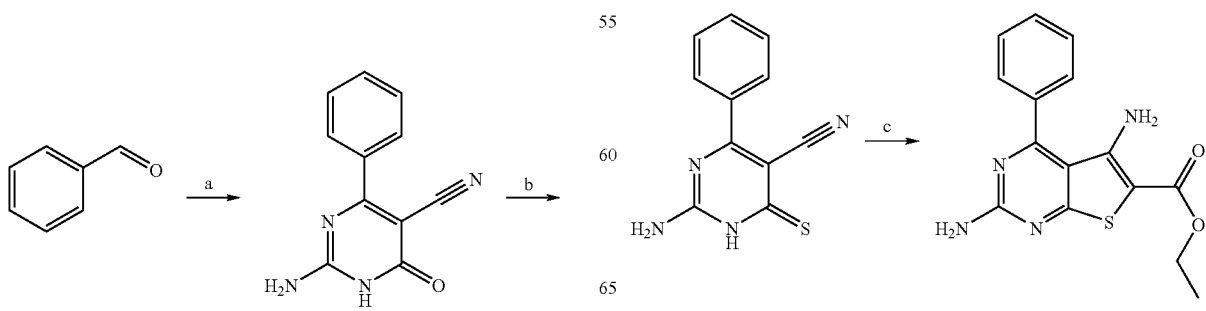

2,5-Diamino-4-phenyl-thieno[2,3-d]pyrimidine-6-carboxylic acid ethyl ester

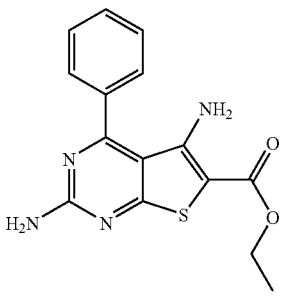

Step 1

2-Amino-6-oxo-4-phenyl-1,6-dihydro-pyrimidine-5-carbonitrile

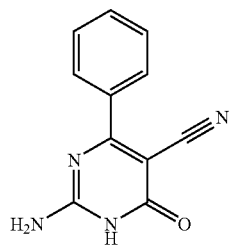

Benzaldehyde (15 g, 141.3 mmol, 1 eq), guanidine carbonate (25.47 g, 141.3 mmol, 1 eq), ethyl cyanoacetate (15.99 g, 141.3 mmol, 1 eq) and anhydrous sodium acetate (11.59 g, 141.3 mmol, 1 eq) were added to 300 ml anhydrous pyridine and refluxed for 4 hours. The reaction was then cooled to room temperature and the solvent was removed under reduced pressure. The brown residue was triturated with 400 ml aqueous acetic acid (30%) and filtered off. The yellow solid was then triturated with 300 ml diethyl ether and filtered off to yield 2-amino-6-oxo-4-phenyl-1,6-dihydro-pyrimidine-5-carbonitrile as an off-white solid.

Yield: 14.46 g (48%)

LCMS retention time=1.34 min, m/z calcd for $C_{11}H_9N_4O$ 213.22 (M+H), found 213.1

Step 2

2-Amino-4-phenyl-6-thioxo-1,6-dihydro-pyrimidine-5-carbonitrile

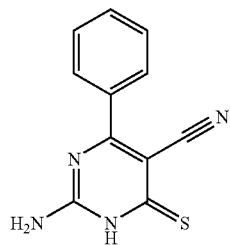

2-Amino-6-oxo-4-phenyl-1,6-dihydro-pyrimidine-5-carbonitrile (0.200 g, 0.942 mmol, 1 eq) and phosphorous pentasulfide (0.838 g, 3.770 mmol, 4 eq) were dissolved in 5 ml pyridine. The reaction was heated under reflux for 2 hours, cooled to room temperature and poured onto 100 ml water. The mixture was boiled for 1 hour, cooled to room temperature and extracted with dichloromethane. The combined organic extracts were washed with saturated brine and dried over anhydrous sodium sulphate. The solvent was removed in vacuo and the orange residue was triturated with diethyl ether to give 2-amino-4-phenyl-6-thioxo-1,6-dihydro-pyrimidine-5-carbonitrile as a yellow solid.

Yield: 0.118 g (55%)

LCMS retention time=1.94 min, m/z calcd for $C_{11}H_9N_4S$ 229.29 (M+H), found 229.1

Step 3

2,5-Diamino-4-phenyl-thieno[2,3-d]pyrimidine-6-carboxylic acid ethyl ester

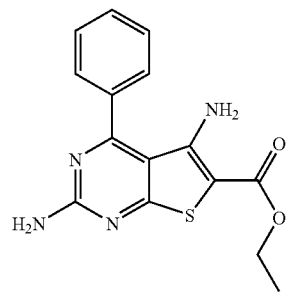

Sodium (0.010 g, 0.438 mmol, 1 eq) was dissolved in 4 ml anhydrous ethanol under nitrogen. 2-Amino-4-phenyl-6-thioxo-1,6-dihydro-pyrimidine-5-carbonitrile (0.100 g, 0.438 mmol, 1 eq) was added and the reaction was stirred at room temperature for 1 hour. 2-Bromoethylacetate (0.073 g, 0.438 mmol, 1 eq) was added. The reaction was stirred for further 30 minutes at room temperature. Then sodium (0.010 g, 0.438 mmol, 1 eq) dissolved in 1 ml anhydrous ethanol was added. The reaction was then refluxed for 5 hours. The reaction was cooled to room temperature and quenched with water. The precipitate was filtered off and triturated with diethyl ether to yield 2,5-diamino-4-phenyl-thieno[2,3-d]pyrimidine-6-carboxylic acid ethyl ester as a yellow solid.

Yield: 0.059 g (43%)

LCMS retention time=2.42 min, m/z calcd for $C_{15}H_{15}N_4O_2S$ 315.38 (M+H), found 315.1

$^1$H NMR (DMSO-$d_6$, 2.50)δ 1.19 (t, 3H, J=7.1), 4.13 (q, 2H, J=7.1), 5.79 (bs, 2H), 7.29 (bs, 2H), 7.50-7.56 (m, 5H)

This compound had activity B in the fluorescence polarisation assay described below.

EXAMPLE 75

2-Amino-5-methyl-4-phenyl-thieno[2,3-d]pyrimidine-6-carboxylic acid amide

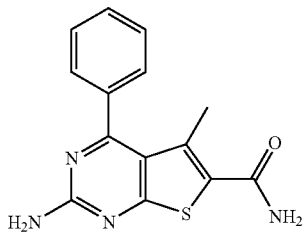

Step 1

5-Amino-4-benzoyl-3-methyl-thiophene-2-carboxylic acid ethyl ester

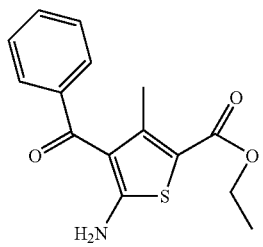

Prepared by Literature Method
Bryan P. McKibben, Craig H. Cartwright, Arlindo L. Castelhano Tetrahedron Lett. 1999, 44, 5471
Step 2

2-Amino-5-methyl-4-phenyl-thieno[2,3-d]pyrimidine-6-carboxylic acid amide

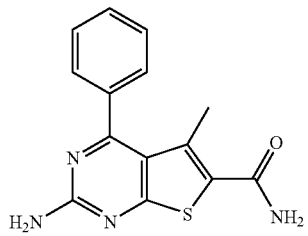

Guanidine carbonate was added to a solution of 5-amino-4-benzoyl-3-methylthiophene-2-carboxylic acid ethyl ester, and the suspension heated, 175° C., for ~3 hrs. under a nitrogen atmosphere. The suspension was allowed to cool and water added. The mixture was extracted with ethyl acetate, extracts were washed and dried. Solution was concentrated and the residue purified by chromatography eluting with mixtures of ethyl acetate and hexane.

LC retention time 2.17 minutes [M+H]+ 285.1 (Run time 3.75 mins)

This compound had activity B in the fluorescence polarization assay described below.

Additional examples prepared by methods similar to those described above are listed in Table 3. The fourth column of Table 3 states the activity of the compound in the fluorescence polarization assay described below.

TABLE 3

| Example | Structure | MH+ | Hsp90 FP IC50 | Synthesis Comment |
|---------|-----------|-----|---------------|-------------------|
| 76 | 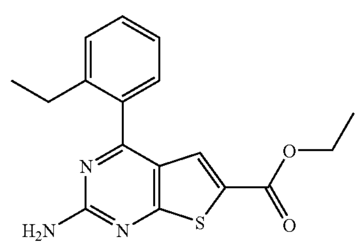 | 328 | B | Suzuki |
| 77 | 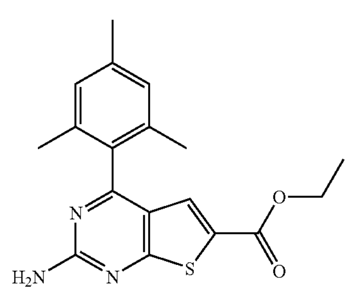 | 342 | A | Suzuki |

TABLE 3-continued

| Example | Structure | MH+ | Hsp90 FP IC50 | Synthesis Comment |
|---|---|---|---|---|
| 78 | 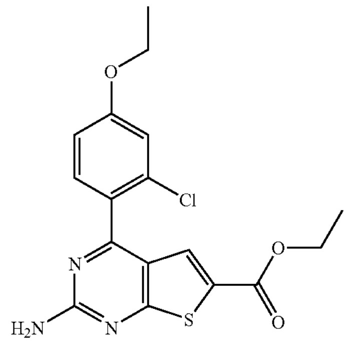 | 378 | A | Suzuki |
| 79 | 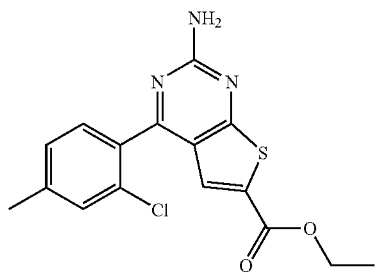 | 348 | A | Suzuki |
| 80 | 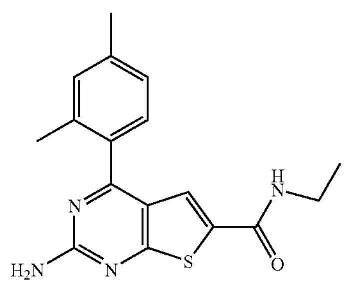 | 327 | A | Suzuki then amide |
| 81 | 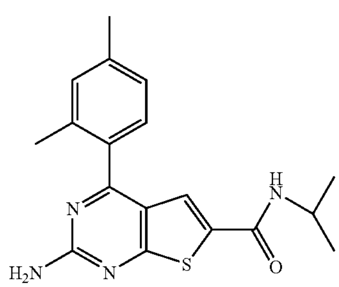 | 341 | A | Suzuki then amide |
| 82 | 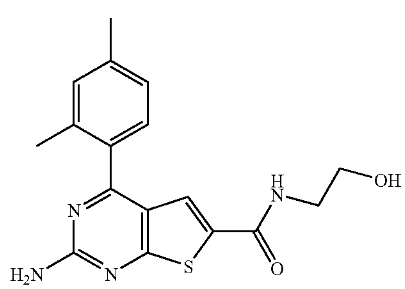 | 343 | A | Suzuki then amide |

TABLE 3-continued

| Example | Structure | MH+ | Hsp90 FP IC50 | Synthesis Comment |
|---------|-----------|-----|---------------|-------------------|
| 83 | 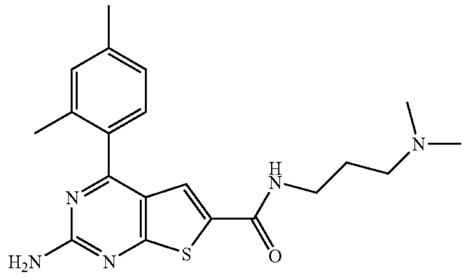 | 384 | A | Suzuki then amide |
| 84 | 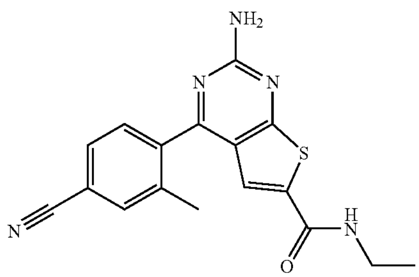 | 338 | A | Suzuki then amide |
| 85 | 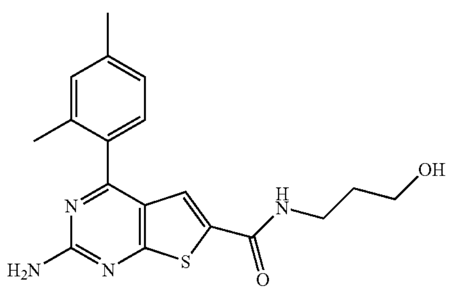 | 357 | A | Suzuki then amide |
| 86 | 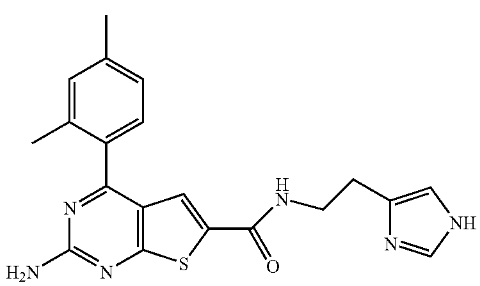 | 393 | A | Suzuki then amide |
| 87 | 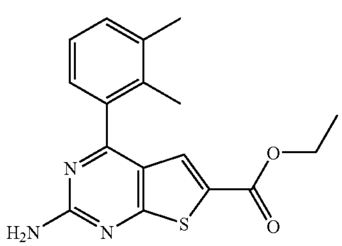 | 328 | A | Suzuki |

TABLE 3-continued

| Example | Structure | MH+ | Hsp90 FP IC50 | Synthesis Comment |
|---|---|---|---|---|
| 88 | 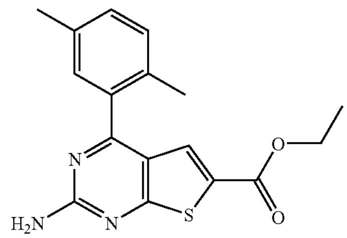 | 328 | A | Suzuki |
| 89 | 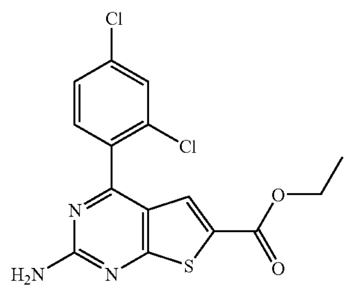 | 367 | A | Suzuki |
| 90 | 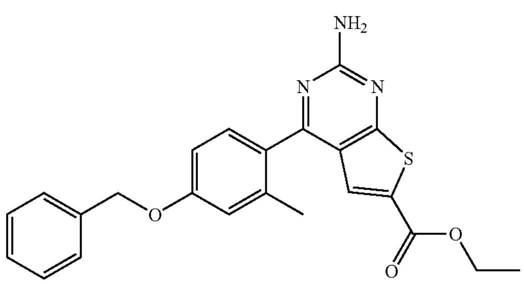 | 420 | B | Suzuki |
| 91 | 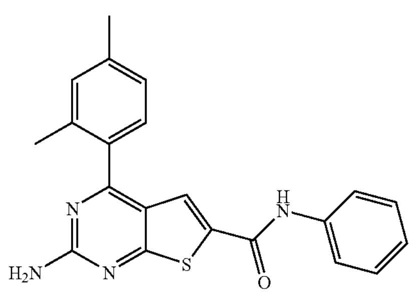 | 375 | A | Suzuki then amide |
| 92 | 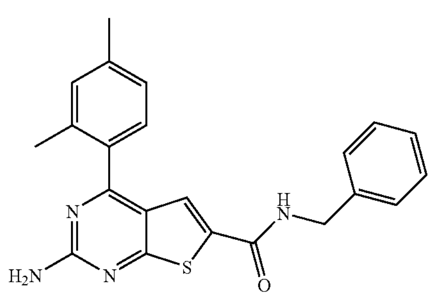 | 389 | A | Suzuki then amide |

TABLE 3-continued

| Example | Structure | MH+ | Hsp90 FP IC50 | Synthesis Comment |
|---|---|---|---|---|
| 93 | 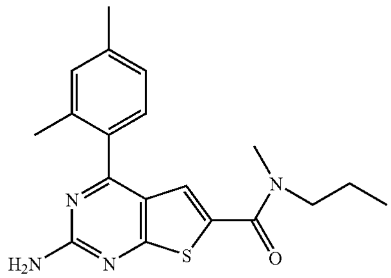 | 355 | B | Suzuki then amide |
| 94 | 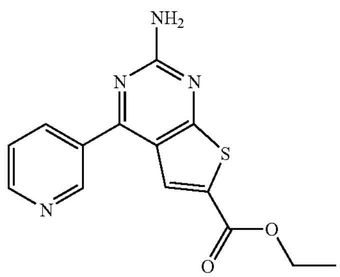 | 301 | B | Suzuki |
| 95 | 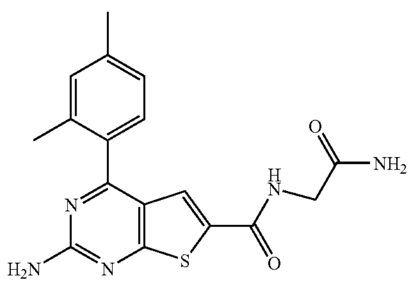 | 356 | A | Suzuki then amide |
| 96 | 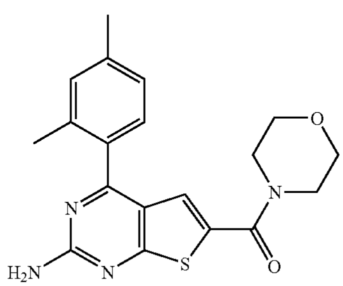 | 369 | B | Suzuki then amide |
| 97 | 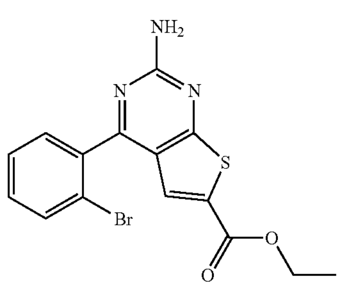 | 379 | A | Suzuki |

TABLE 3-continued

| Example | Structure | MH+ | Hsp90 FP IC50 | Synthesis Comment |
|---|---|---|---|---|
| 98 | 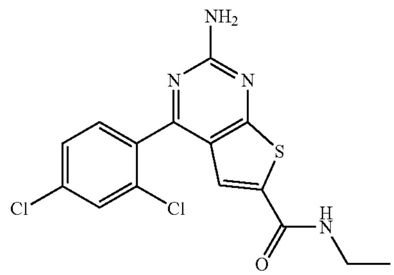 | 367 | A | Suzuki then amide |
| 99 | 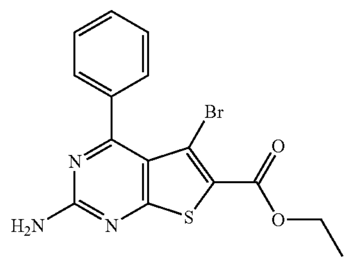 | 379 | B | diazotisation and bromination of Example 75 |
| 100 | 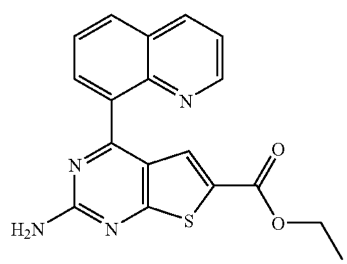 | 351 | B | Suzuki |
| 101 | 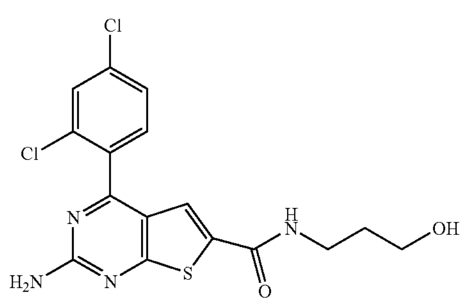 | 397 | A | Suzuki then amide |
| 102 | 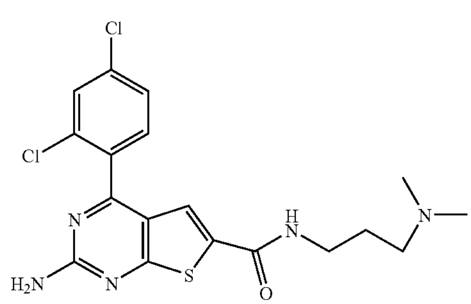 | 424 | A | Suzuki then amide |

TABLE 3-continued

| Example | Structure | MH+ | Hsp90 FP IC50 | Synthesis Comment |
|---------|-----------|-----|---------------|-------------------|
| 103 | 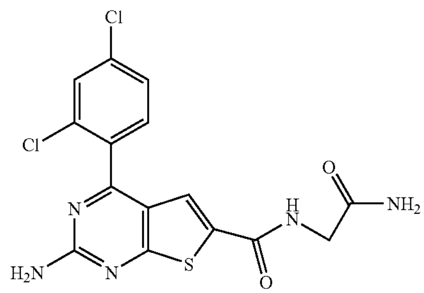 | 396 | A | Suzuki then amide |
| 104 | 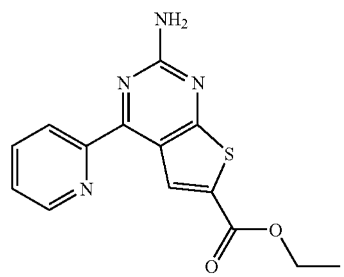 | 301 | B | Suzuki |
| 105 | 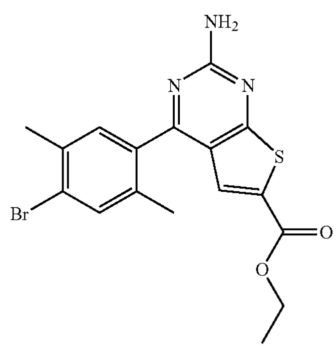 | 407 | A | Suzuki |
| 106 | 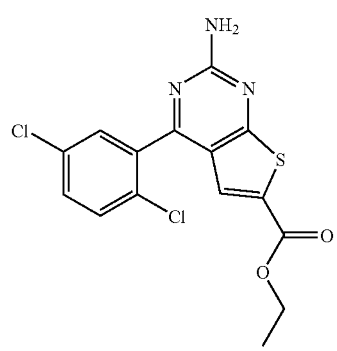 | 368 | B | Suzuki |
| 107 | 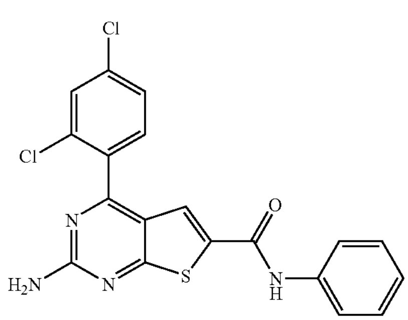 | 415 | A | Suzuki then amide |

TABLE 3-continued

| Example | Structure | MH+ | Hsp90 FP IC50 | Synthesis Comment |
|---------|-----------|-----|---------------|-------------------|
| 108 | 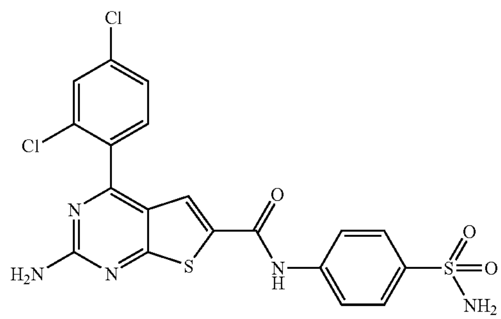 | 494 | A | Suzuki then amide |
| 109 | 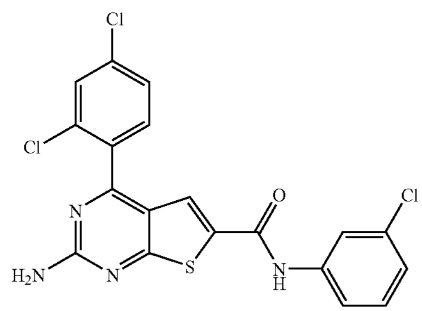 | 449 | A | Suzuki then amide |
| 110 | 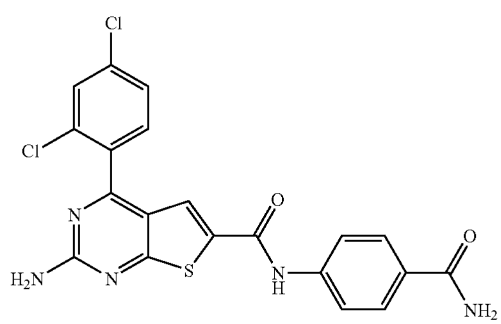 | 458 | A | Suzuki then amide |
| 111 | 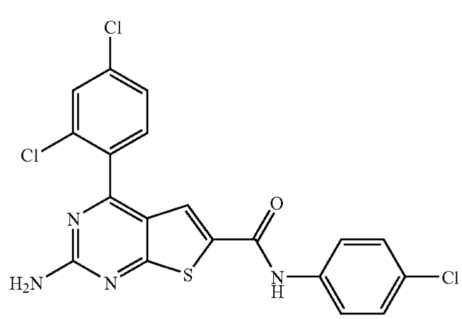 | 449 | A | Suzuki then amide |

TABLE 3-continued
| Example | Structure | MH+ | Hsp90 FP IC50 | Synthesis Comment |
|---|---|---|---|---|
| 112 | 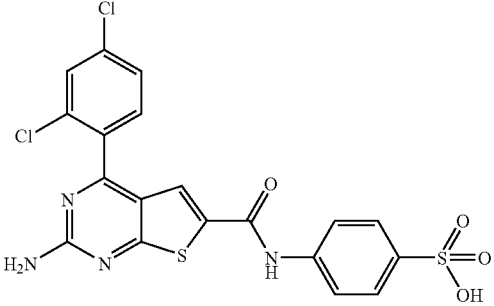 | 495 | A | Suzuki then amide |
| 113 | 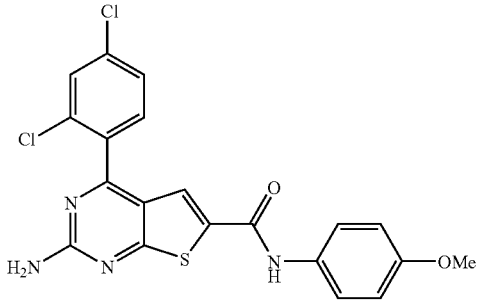 | 445 | A | Suzuki then amide |
| 114 | 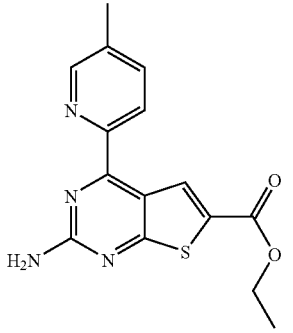 | 315 | A | Suzuki |
| 115 | 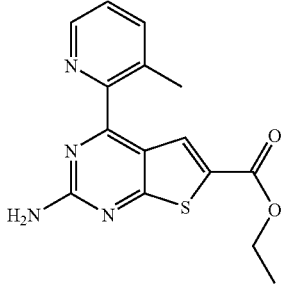 | 315 | A | Suzuki |
| 116 | 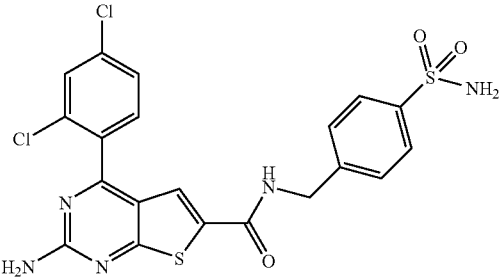 | 508 | A | Suzuki then amide |

TABLE 3-continued

| Example | Structure | MH+ | Hsp90 FP IC50 | Synthesis Comment |
|---------|-----------|-----|---------------|-------------------|
| 117 | 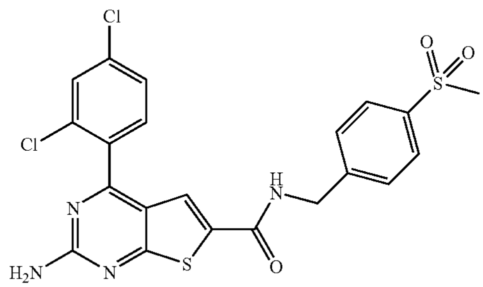 | 507 | A | Suzuki then amide |
| 118 | 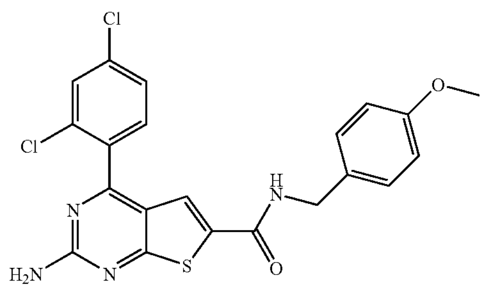 | 459 | A | Suzuki then amide |
| 119 | 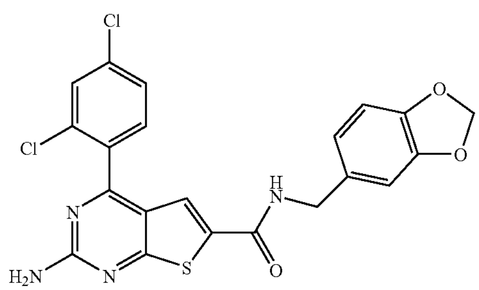 | 473 | A | Suzuki then amide |
| 120 | 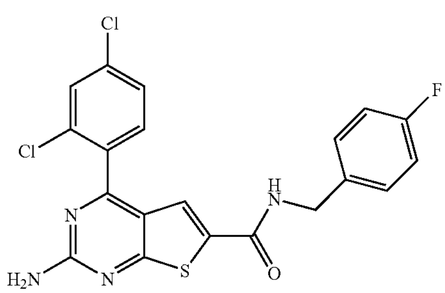 | 447 | A | Suzuki then amide |
| 121 | 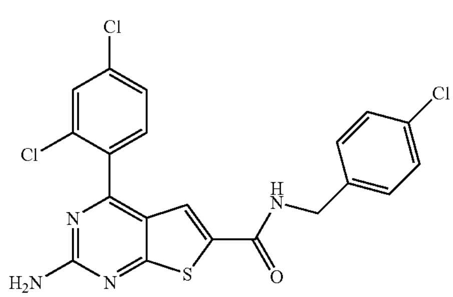 | 463 | A | Suzuki then amide |

TABLE 3-continued

| Example | Structure | MH+ | Hsp90 FP IC50 | Synthesis Comment |
|---|---|---|---|---|
| 122 | 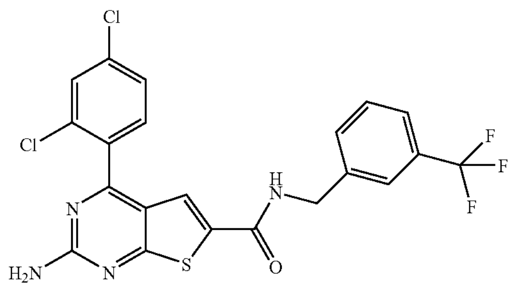 | 497 | A | Suzuki then amide |
| 123 | 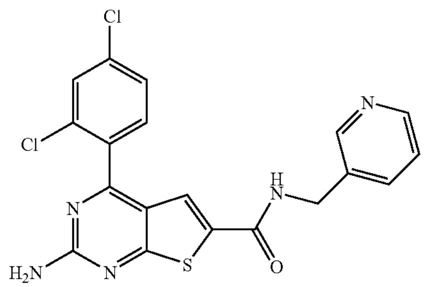 | 432 | A | Suzuki then amide |
| 124 | 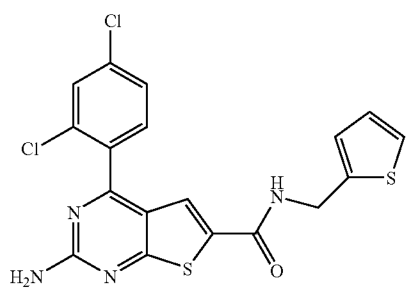 | 435 | A | Suzuki then amide |
| 125 | 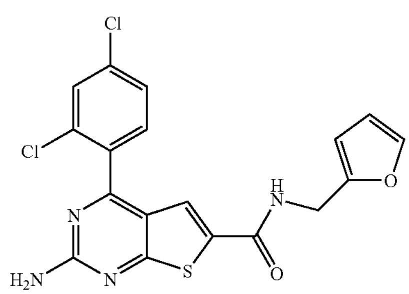 | 419 | A | Suzuki then amide |
| 126 | 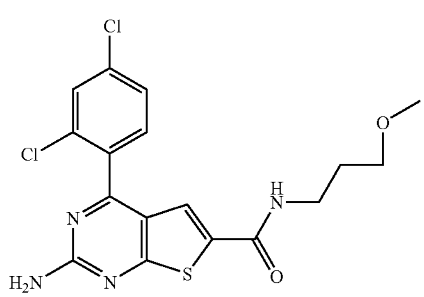 | 411 | A | Suzuki then amide |

TABLE 3-continued

| Example | Structure | MH+ | Hsp90 FP IC50 | Synthesis Comment |
|---|---|---|---|---|
| 127 | 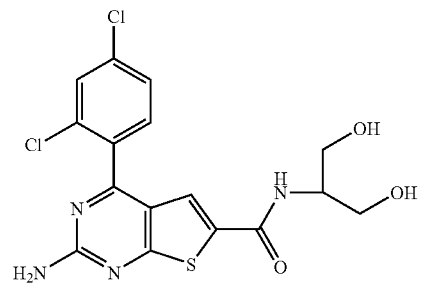 | 413 | A | Suzuki then amide |
| 128 | 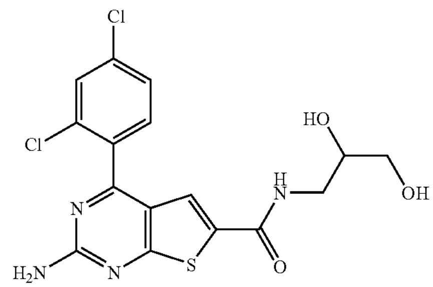 | 413 | A | Suzuki then amide |
| 129 | 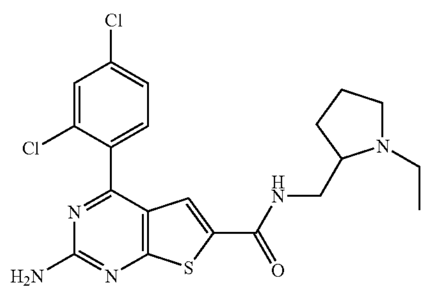 | 450 | A | Suzuki then amide |
| 130 | 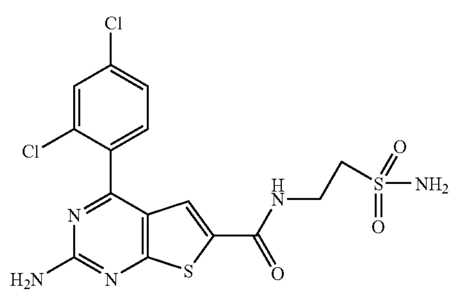 | 446 | A | Suzuki then amide |
| 131 | 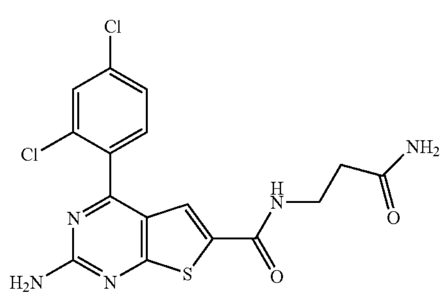 | 410 | A | Suzuki then amide |

TABLE 3-continued

| Example | Structure | MH+ | Hsp90 FP IC50 | Synthesis Comment |
|---|---|---|---|---|
| 132 | 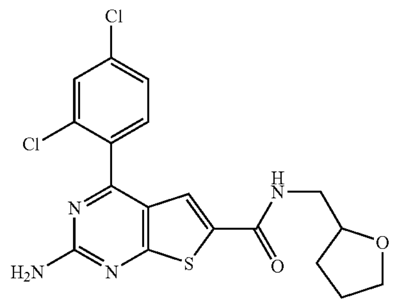 | 423 | A | Suzuki then amide |
| 133 | 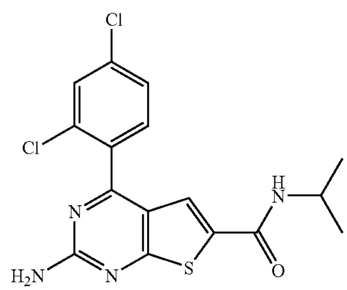 | 381 | A | Suzuki then amide |
| 134 | 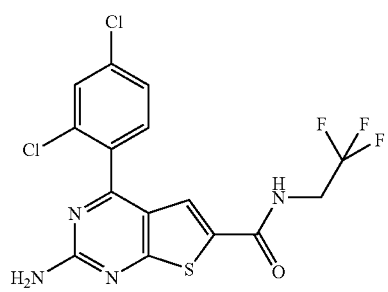 | 421 | A | Suzuki then amide |
| 135 | 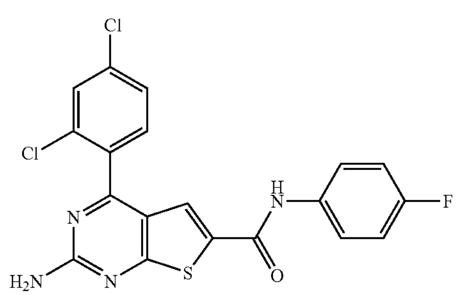 | 433 | A | Suzuki then amide |
| 136 | 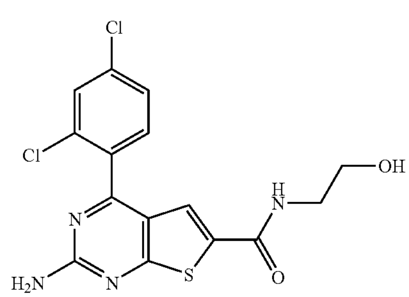 | 383 | A | Suzuki then amide |

TABLE 3-continued

| Example | Structure | | MH+ | Hsp90 FP IC50 | Synthesis Comment |
|---|---|---|---|---|---|
| 137 | [2-amino-4-(2,4-dichlorophenyl)thieno[2,3-d]pyrimidine-6-carboxamide with N-(1-methylpiperidin-4-yl)] | | 436 | A | Suzuki then amide |
| 138 | [2-amino-4-(2,4-dichlorophenyl)thieno[2,3-d]pyrimidine-6-carboxamide with N-((R)-1-phenylethyl)] | Chiral | 443 | A | Suzuki then amide |
| 139 | [2-amino-4-(2,4-dichlorophenyl)thieno[2,3-d]pyrimidine-6-carboxamide with N-((S)-1-phenylethyl)] | Chiral | 443 | A | Suzuki then amide |
| 140 | [2-amino-4-(2,4-dichlorophenyl)thieno[2,3-d]pyrimidine-6-carboxamide with N-(2-phenylpropan-2-yl)] | | 457 | A | Suzuki then amide |
| 141 | [2-amino-4-(3,4-dichlorophenyl)thieno[2,3-d]pyrimidine-6-carboxamide with N-(pyridin-4-ylmethyl)] | | 430 | A | Suzuki then amide |

TABLE 3-continued

| Example | Structure | MH+ | Hsp90 FP IC50 | Synthesis Comment |
|---|---|---|---|---|
| 142 | 4-(2,4-dichlorophenyl)-2-amino-N-(thiazol-2-yl)thieno[2,3-d]pyrimidine-6-carboxamide | 422 | A | Suzuki then amide |
| 143 | 4-(2,4-dichlorophenyl)-2-amino-N-(1H-pyrazol-3-yl)thieno[2,3-d]pyrimidine-6-carboxamide | 405 | A | Suzuki then amide |
| 144 | 4-(2,4-dichlorophenyl)-2-amino-N-(3-sulfopropyl)thieno[2,3-d]pyrimidine-6-carboxamide | 461 | A | Suzuki then amide |
| 145 | 4-(2,4-dichlorophenyl)-2-amino-N-(3-(pyrrolidin-1-yl)propyl)thieno[2,3-d]pyrimidine-6-carboxamide | 450 | A | Suzuki then amide |
| 146 | 4-(2,4-dichlorophenyl)-2-amino-N-(3-(1H-imidazol-1-yl)propyl)thieno[2,3-d]pyrimidine-6-carboxamide | 447 | A | Suzuki then amide |

TABLE 3-continued

| Example | Structure | MH+ | Hsp90 FP IC50 | Synthesis Comment |
|---|---|---|---|---|
| 147 | 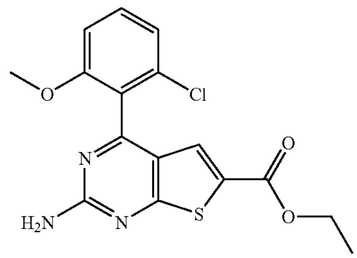 | 364 | B | Suzuki |
| 148 | 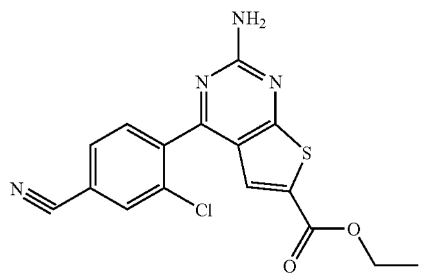 | 359 | A | Suzuki |
| 149 | 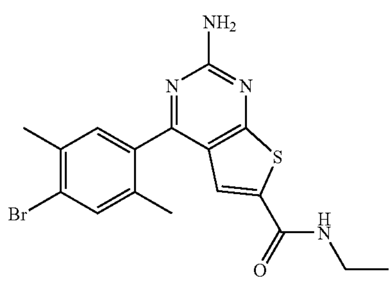 | 406 | A | Suzuki then amide |
| 150 | 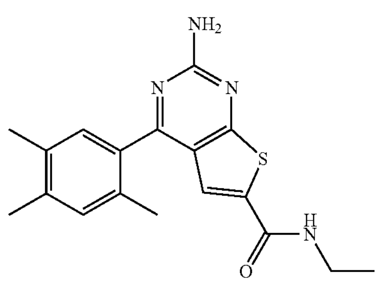 | 341 | A | Suzuki then amide |
| 151 | 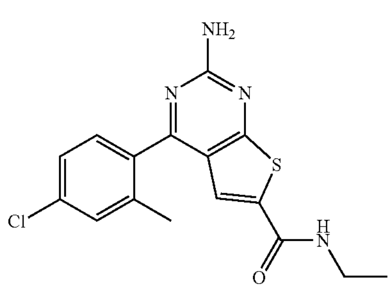 | 347 | A | Suzuki then amide |

TABLE 3-continued
| Example | Structure | MH+ | Hsp90 FP IC50 | Synthesis Comment |
|---|---|---|---|---|
| 152 | 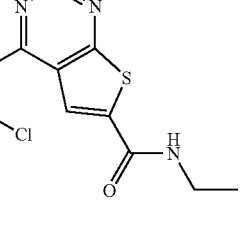 | 347 | A | Suzuki then amide |
| 153 | 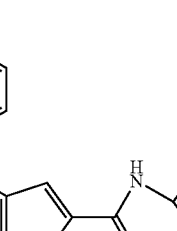 | 407 | A | Suzuki then amide |
| 154 | 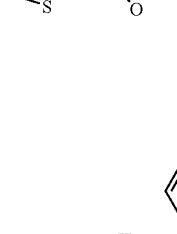 | 430 | A | Suzuki then amide |
| 155 | 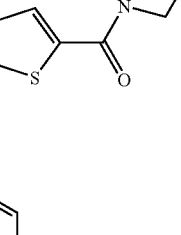 | 379 | A | Suzuki then amide |
| 156 | 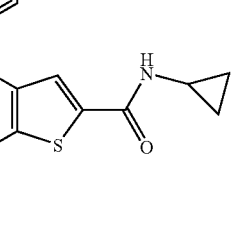 | 444 | A | Suzuki then amide |

TABLE 3-continued

| Example | Structure | MH+ | Hsp90 FP IC50 | Synthesis Comment |
|---------|-----------|-----|---------------|-------------------|
| 157 | 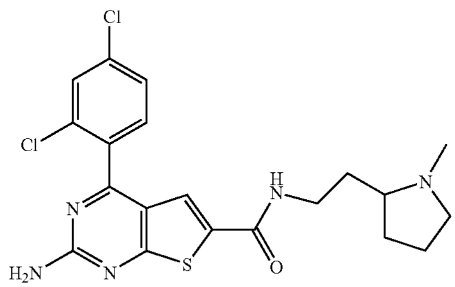 | 450 | A | Suzuki then amide |
| 158 | 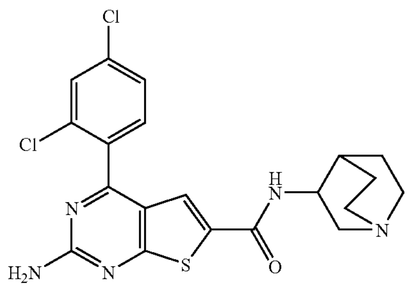 | 448 | A | Suzuki then amide |
| 159 | 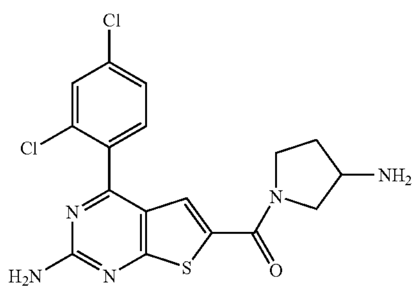 | 408 | A | Suzuki then amide |
| 160 | Chiral | 410 | A | Suzuki then amide |
| 161 | Chiral | 452 | A | Suzuki then amide |

TABLE 3-continued

| Example | Structure | | MH+ | Hsp90 FP IC50 | Synthesis Comment |
|---|---|---|---|---|---|
| 162 | 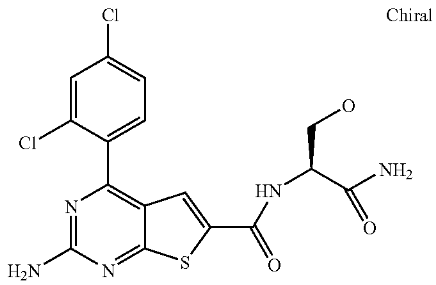 | Chiral | 426 | A | Suzuki then amide |
| 163 | 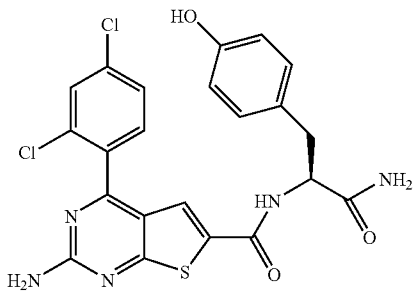 | Chiral | 502 | A | Suzuki then amide |
| 164 | 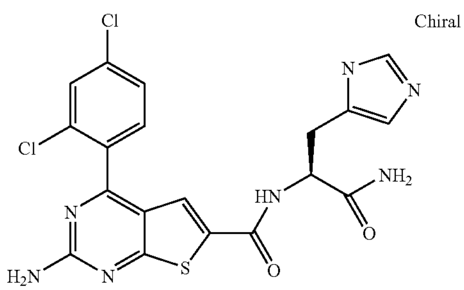 | Chiral | 476 | A | Suzuki then amide |
| 165 | 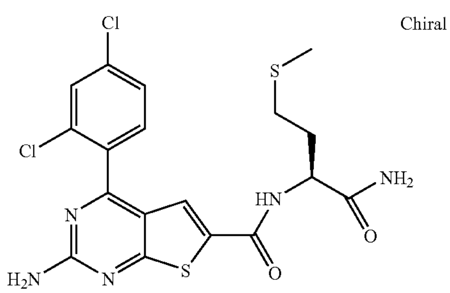 | Chiral | 477 | A | Suzuki then amide |
| 166 | 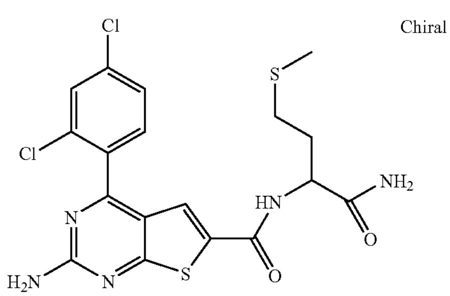 | Chiral | 472 | A | Suzuki then amide |

TABLE 3-continued

| Example | Structure | MH+ | Hsp90 FP IC50 | Synthesis Comment |
|---|---|---|---|---|
| 167 | 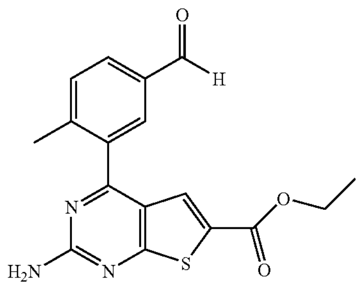 | 342 | A | Suzuki |
| 168 | 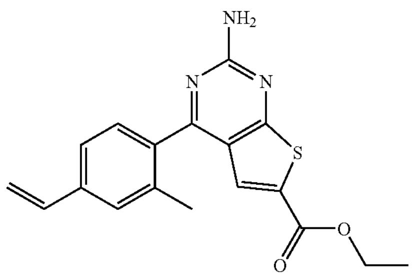 | 340 | A | Suzuki |
| 169 | 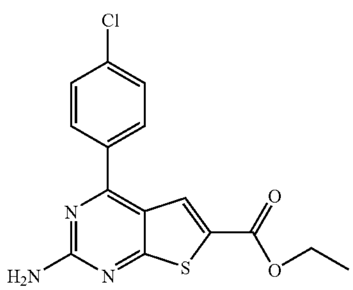 | 334 | A | Suzuki |
| 170 | 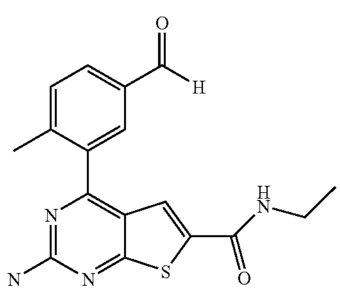 | 341 | A | Suzuki then amide |
| 171 | 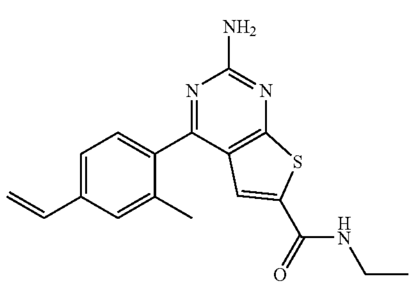 | 339 | A | Suzuki then amide |

TABLE 3-continued

| Example | Structure | MH+ | Hsp90 FP IC50 | Synthesis Comment |
|---|---|---|---|---|
| 172 | 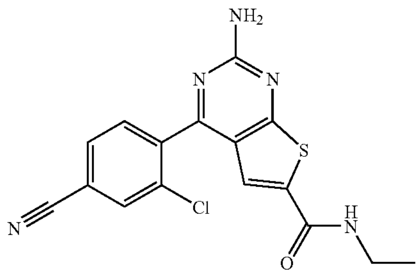 | 358 | A | Suzuki then amide |
| 173 | 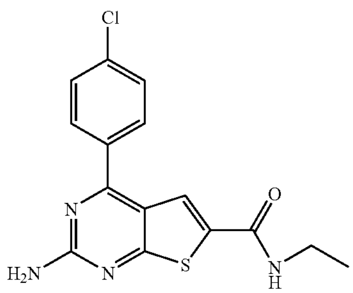 | 333 | A | Suzuki then amide |
| 174 | 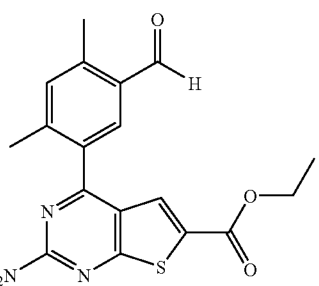 | 356 | A | Suzuki |
| 175 | 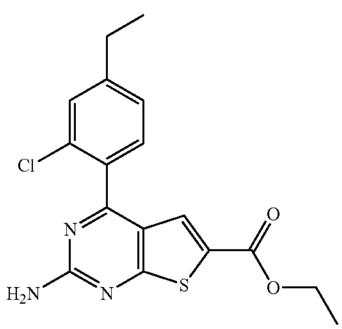 | 362 | A | Suzuki |
| 176 | 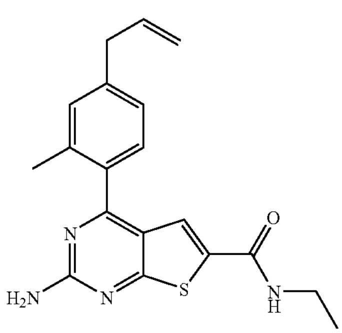 | 353 | A | Suzuki then amide |

TABLE 3-continued

| Example | Structure | MH+ | Hsp90 FP IC50 | Synthesis Comment |
|---------|-----------|-----|---------------|-------------------|
| 177 | 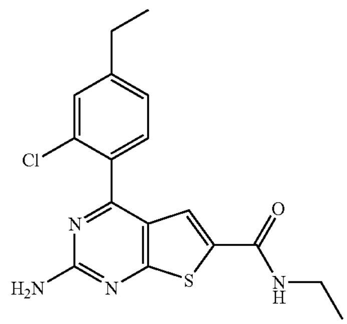 | 361 | A | Suzuki then amide |
| 178 | 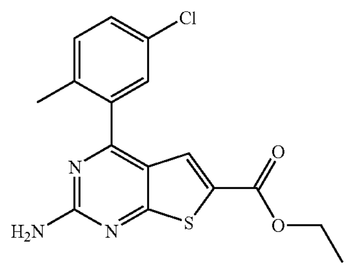 | 348 | A | Suzuki |
| 179 | 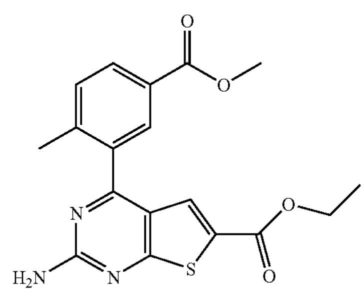 | 372 | A | Suzuki |
| 180 | 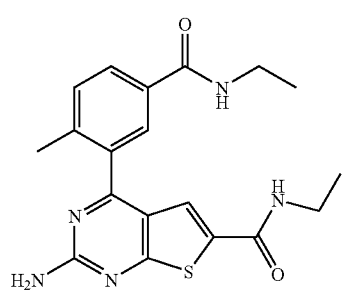 | 384 | A | Suzuki then amide |
| 181 | 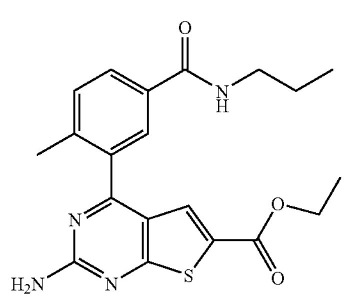 | 399 | A | Suzuki |

TABLE 3-continued

| Example | Structure | MH+ | Hsp90 FP IC50 | Synthesis Comment |
|---|---|---|---|---|
| 182 | 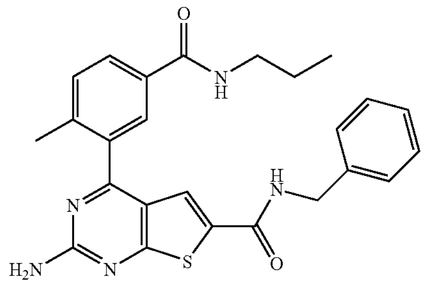 | 460 | B | Suzuki then amide |
| 183 | 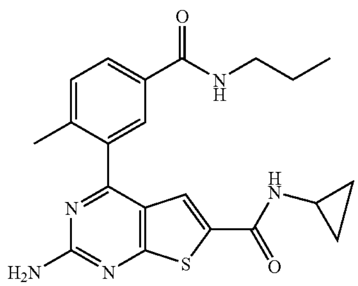 | 410 | A | Suzuki then amide |

EXAMPLE 184

2-Amino-4-(4-hydroxy-2-methyl-phenyl-thieno[2,3-d]pyrimidine-6-carboxylic acid ethyl ester

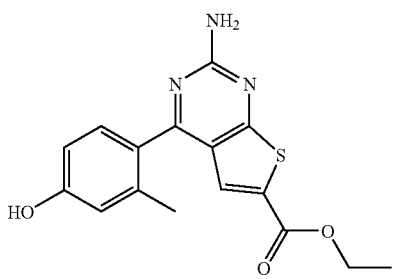

Step 1

2-Amino-4-(4-benzyloxy-2-methyl-phenyl)-thieno[2,3-d]pyrimidine-6-carboxylic acid ethyl ester

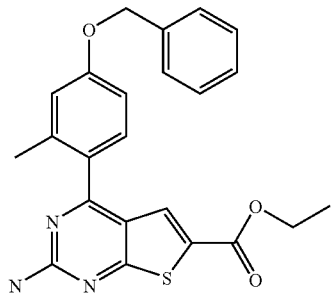

2-methyl-4-benzyloxyphenylboronic acid (225 mg; 0.93 mmol) was added to 2-Amino-4-chloro-thieno[2,3-d]pyrimidine-6-carboxylic acid ethyl ester (example 1; step 1) (200 mg; 0.776 mmol) in DMF (10 mL). NaHCO₃ (1.0M aq. Solution; 2.33 mL) was added and mixture degassed with N₂. Pd(PPh₃)₂Cl₂ was added and reaction mixture heated at 80 degrees C. for 5 hours Reaction mixture was allowed to cool to room temperature and DMF removed in vacuo. The residue was partitioned between ethyl acetate (50 mL) and sat. NaCl (aq) (50 mL) Organic phase was dried over Na₂SO₄ and filtered, filtrate solvents removed in vacuo to afford a yellow oil which was purified by ion-exchange chromatography (IST SCX-2 column) to afford product as a brown-yellow solid (230 mg; 71%)

LC-MS retention time: 2.852 minutes, [M+H]⁺ 420 (Run time 3.75 mins)

Step 2

2-Amino-4-(4-hydroxy-2-methyl-phenyl)-thieno[2,3-d]pyrimidine-6-carboxylic acid ethyl ester

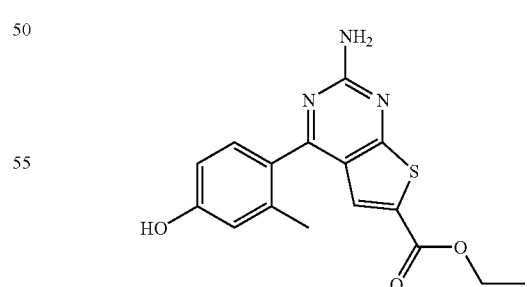

To an ice-bath cooled solution of 2-Amino-4-(4-benzyloxy-2-methyl-phenyl-thieno[2,3-d]pyrimidine-6-carboxylic acid ethyl ester (211 mg; 0.5 mmol) in dichloromethane (8 mL), was added BCl₃ (1.0M solution in DCM; 1.51 mL; 1.5 mmol). Reaction mixture was stirred for 30 mins and then aqueous ammonia was added (20 mL) and reaction mixture extracted with ethyl acetate (2×30 mL). Organic phase was dried over Na$_2$SO$_4$ and filtered, filtrate solvents removed in vacuo to afford a yellow solid which was purified by flash chromatography on silica gel (10 g IST Flash; eluting 10 to 40% ethyl acetate in hexane) to afford product as a colourless solid (102 mg, 62%)

LC-MS retention time: 2.852 minutes, [M+H]$^+$ 420 (Run time 3.75 mins)

This compound had activity A in the fluorescence polarization assay described below

EXAMPLE 185

2-Amino-4-(2-methyl-4-propoxy-phenyl)-thieno[2,3-d]pyrimidine-6-carboxylic acid ethyl ester

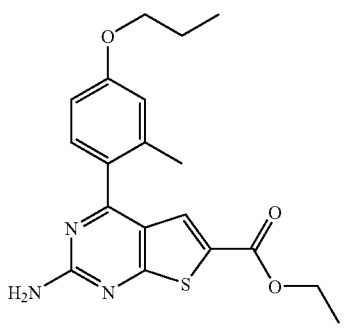

1-Bromopropane (15 uL; 0.17 mmol) was added to a solution of 2-Amino-4-(4-hydroxy-2-methyl-phenyl)-thieno[2,3-d]pyrimidine-6-carboxylic acid ethyl ester (50 mg: 0.152 mmol) and potassium carbonate (25 mg; 0.18 mmol) in DMF (15 mL). Reaction mixture was heated to 50 degrees C. for 18 hours. Reaction mixture was allowed to cool and solvent removed in vacuo. Residue was partitioned between saturated aqueous sodium bicarbonate solution (10 mL) and ethyl acetate (20 mL). Organic phase was dried over Na$_2$SO$_4$ and filtered, filtrate solvents removed in vacuo to afford a yellow solid purified by flash chromatography on silica gel (eluting ethyl acetate in hexane) to afford product as yellow solid (45 mg; 80%)

LC-MS retention time: 2.821 minutes, [M+H]$^+$ 372 (Run time 3.75 mins)

This compound had activity A in the fluorescence polarization assay described below.

The following compounds (Table 4) were made by the method of Example 185, substituting the appropriate alkylating agent for bromopropane. The fourth column of Table 4 states the activity of the compound in the fluorescence polarization assay described below.

TABLE 4

| Example | Structure | MH+ | Hsp90 FP IC50 | Synthesis Comment |
|---|---|---|---|---|
| 186 | 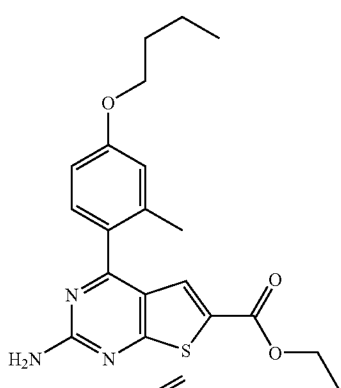 | 386 | B | Suzuki then alkylation |
| 187 | 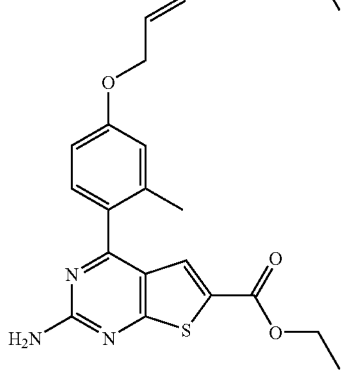 | 370 | A | Suzuki then alkylation |

TABLE 4-continued

| Example | Structure | MH+ | Hsp90 FP IC50 | Synthesis Comment |
| --- | --- | --- | --- | --- |
| 188 | 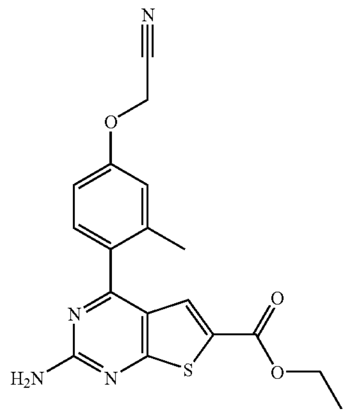 | 369 | A | Suzuki then alkylation |
| 189 | 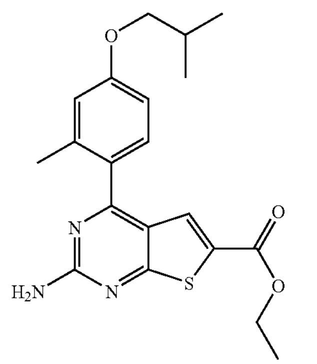 | 386 | B | Suzuki then alkylation |
| 190 | 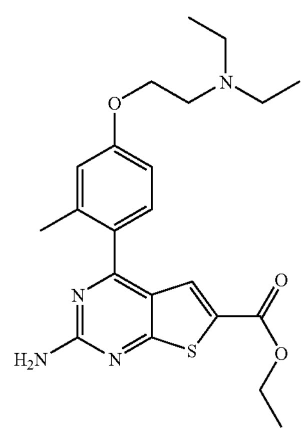 | 429 | B | Suzuki then alkylation |
| 191 | 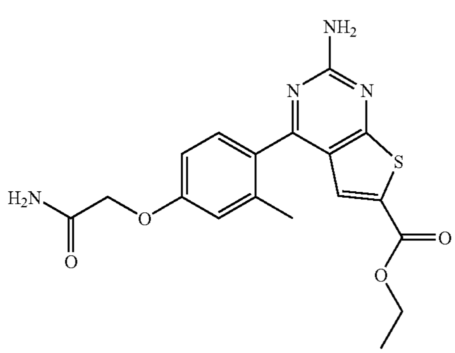 | 387 | A | Suzuki then alkylation |

TABLE 4-continued
| Example | Structure | MH+ | Hsp90 FP IC50 | Synthesis Comment |
|---|---|---|---|---|
| 192 | 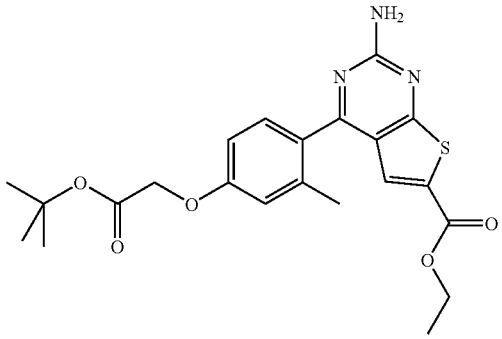 | 444 | B | Suzuki then alkylation |
| 193 | 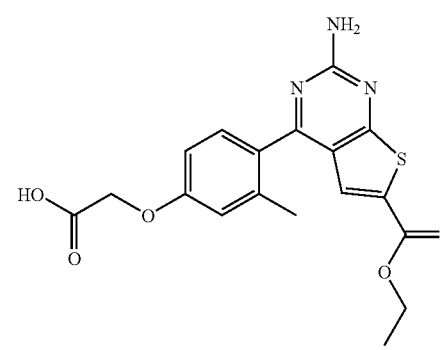 | 388 | B | Suzuki then alkylation |
| 194 | 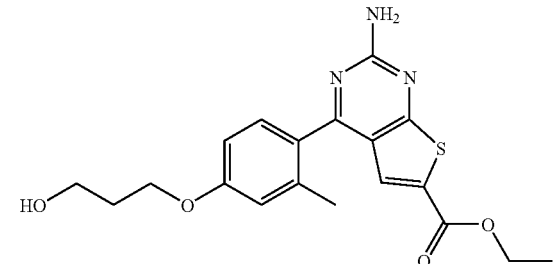 | 388 | A | Suzuki then alkylation |
| 195 | 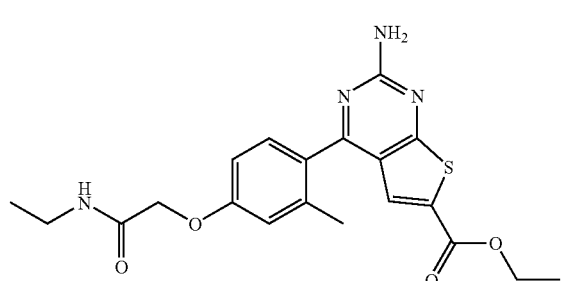 | 415 | A | Suzuki then alkylation |

EXAMPLE 196

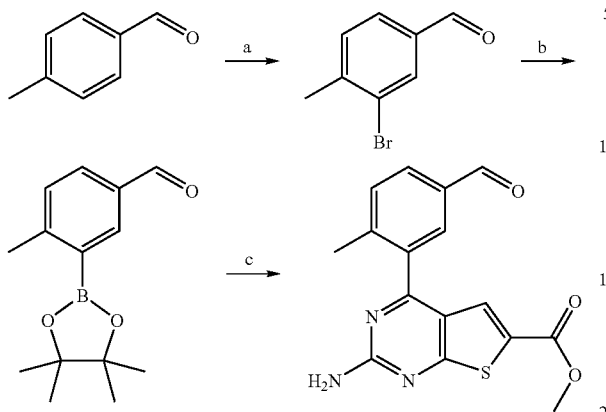

2-Amino-4-(5-formyl-2-methyl-phenyl)-thieno[2,3-d]pyrimidine-6-carboxylic acid ethyl ester

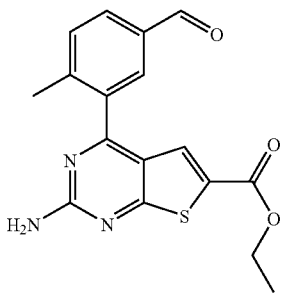

Step 1

3-Bromo-4-methyl-benzaldehyde

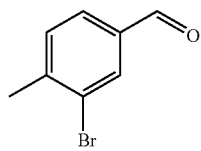

Prepared as described by Eizenber and Ammons, *Org Prep and Reactions Int.*, 6(5), 251-253 (1974) from p-tolualdehyde (12.00 g)

Yield: 10.97 g (55%)

LCMS retention time=2.57 min; no ionisation.

$^1$H NMR (400 MHz; CDCl$_3$) δ 2.50 (s, 3H), 7.43 (d, 1H, J=7.8 Hz), 7.75 (dd, 1H, J=7.8 and 1.6 Hz), 8.05 (d, 1H, J=1.6 Hz), 9.94 (s, 1H)

Step 2

4-Methyl-3-(4,4,5,5-tetramethyl-[1,3,2]dioxaborolan-2-yl)-benzaldehyde

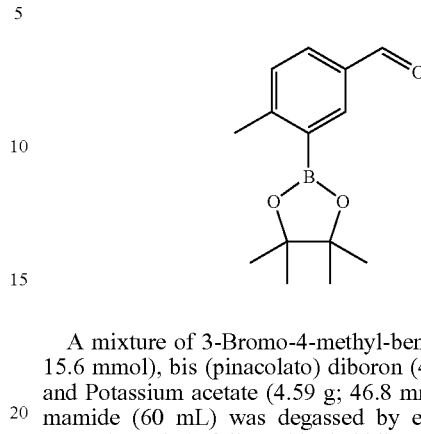

A mixture of 3-Bromo-4-methyl-benzaldehyde (3.105 g; 15.6 mmol), bis (pinacolato) diboron (4.29 g; 16.86 mmol) and Potassium acetate (4.59 g; 46.8 mmol) in dimethylformamide (60 mL) was degassed by evacuation—nitrogen purge (3 cycles), followed by bubbling nitrogen gas through the stirred reaction mixture for 5 minutes. Palladium acetate (0.120 g; 0.536 mmol) was added and reaction mixture was heated to 85 degrees C. (oil-bath temperature) for 2.5 hours. Reaction mixture was allowed to cool to room temperature and DMF removed in vacuo. The residue was partitioned between ethyl acetate (150 mL) and water (150 mL) and the mixture was filtered through a pad of celite to remove black Pd solids. Filter cake was washed with ethyl acetate (2×50 mL) and combined filtrate phases were separated and the organic phase was washed with water (2×150 mL) then saturated sodium chloride solution (150 mL). Organic phase was dried over Na$_2$SO$_4$ and filtered, filtrate solvents removed in vacuo to afford a yellow oil which was purified by flash chromatography on silica gel (50 g IST Flash; eluting 0 to 10% ethyl acetate in hexane) to afford product as a colourless solid Yield: 4.58 g; 85%

LC-MS retention time=2.799 min; [M+H]$^+$ 247

$^1$H NMR (400 MHz, CDCl$_3$) δ 1.36 (s, 12H), 2.62 (s, 3H), 7.31 (d, 1H, J=7.88 Hz), 7.83 (dd, 1H, J=7.88 and 1.9 Hz), 8.25 (d, 1H, J=1.9 Hz), 9.98 (s, 1H)

Step 3

2-Amino-4-(5-formyl-2-methyl-phenyl)-thieno[2,3-d]pyrimidine-6-carboxylic acid ethyl ester

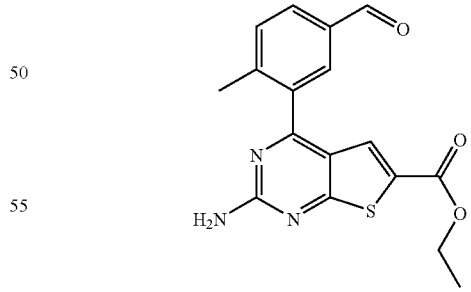

2-Amino-4-chloro-thieno[2,3-d]pyrimidine-6-carboxylic acid ethyl ester (7.62 g, 29.57 mmol) was added to 4-Methyl-3-(4,4,5,5-tetramethyl-[1,3,2]dioxaborolan-2-yl)-benzaldehyde (7.28 g, 29.57 mmol) followed by sodium hydrogen carbonate (7.45 g, 88.71 mmol). DMF (110 mL) was added followed by water (22 mL) and the suspension was degassed by evacuation—nitrogen purge (3 cycles), followed by bubbling nitrogen gas through the stirred reaction mixture for 5 minutes. Bis(triphenylphosphine)palladium (II) chloride (500 mg, 0.739 mmol) was added and reaction mixture was heated to 85 degrees C. (oil-bath temperature) for 18 hours. Reaction mixture was allowed to cool to room temperature and DMF removed in vacuo. The residue was partitioned between ethyl acetate (500 mL) and water (400 mL) and the mixture was stirred vigorously for 15 min before being filtered through a pad of celite to remove Pd solids. Filter cake was washed with ethyl acetate (2×50 mL) and combined filtrate phases were separated and the organic phase was washed with water (1×300 mL) then saturated sodium chloride solution (250 mL). Organic phase was dried over $Na_2SO_4$ and filtered, and filtrate solvents removed in vacuo to afford a brown oily solid which was triturated with ethyl acetate to afford product as a brown solid (5.42 g, 56%)

LC-MS retention time=2.436 min; $[M+H]^+$ 342

$^1$H NMR (400 MHz, $d_6$-DMSO) 1.30 (t, 3H), 2.38 (s, 3H), 4.32 (q, 2H), 7.48 (s, 2H), 7.71 (d, 2H), 7.91 (s, 1H), 7.97 (d, 1H), 10.11 (s, 1H)

This compound had activity A in the fluorescence polarization assay described below.

EXAMPLE 197

2-Amino-4-(2-methyl-5-propylaminomethyl-phenyl)-thieno[2,3-d]pyrimidine-6-carboxylic acid ethylamide

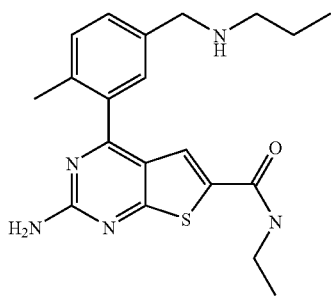

Methanol (5 mL) was added to 2-Amino-4-(5-formyl-2-methyl-phenyl)-thieno[2,3-d]pyrimidine-6-carboxylic acid ethyl ester (100 mg, 0.29 mmol) and propylamine (0.586 mmol) then added to resulting suspension. Reaction mixture was heated to reflux (affording homogeneous brown solution) for 4 hours then allowed to cool to ambient temperature. Sodium borohydride (23 mg; 0.58 mmol) was added and reaction mixture stirred for 30 mins. Methanol was removed in vacuo and the residue was partitioned between water (20 mL) and ethyl acetate (20 mL). The phases were separated and organic phase was dried over $Na_2SO_4$ and filtered, and filtrate solvents removed in vacuo to afford brown solid which was suspended 2.0M ethylamine in methanol solution (5.0 mL, 10 mmol) and heated in sealed tube at 85 degrees C. overnight. Reaction mixture was allowed to cool and solvents removed in vacuo to afford a brown solid which was triturated in hot ethyl acetate, filtered and dried to afford title product as light-brown solid (50 mg, 45%)

LC-MS retention time=2.436 min; $[M+H]^+$ 342

$^1$H NMR (400 MHz, $d_6$-DMSO) δ 0.79 (t, 3H, J=7.4 Hz), 1.01 (t, 3H, J=7.2 Hz), 1.35 (m, 2H), 2.12 (s, 3H), 2.39 (m, 2H), 3.13 (m, 2H), 3.25 (s, 2H), 3.65 (s, 2H), 7.02 (s, 2H), 7.2-7.38 (m, 3H), 7.48 (s, 1H), 8.52 (t, 3H, J=5.4 Hz)

This compound had activity A in the fluorescence polarization assay described below.

The following compounds (Table 5) were made by the method of Example 197, substituting the appropriate amine for propylamine. The fourth column of Table 5 states the activity of the compound in the fluorescence polarization assay described below.

TABLE 5

| Example | Structure | MH+ | Hsp90 FP IC50 | Synthesis Comment |
|---|---|---|---|---|
| 198 | 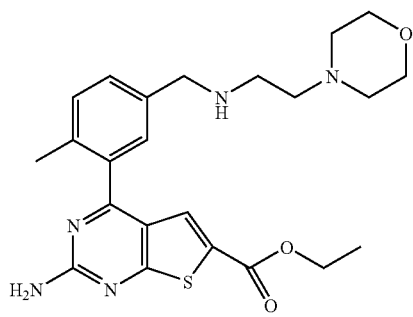 | 456 | A | Reductive amination |

TABLE 5-continued

| Example | Structure | MH+ | Hsp90 FP IC50 | Synthesis Comment |
|---|---|---|---|---|
| 199 | 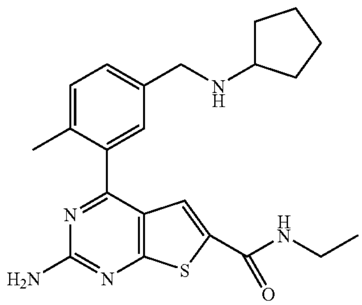 | 410 | A | Reductive amination then amide |
| 200 | 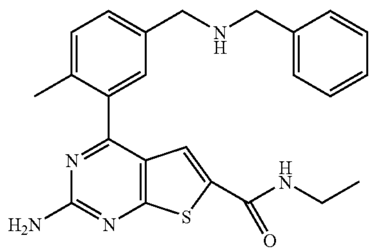 | 432 | A | Reductive amination then amide |
| 201 | 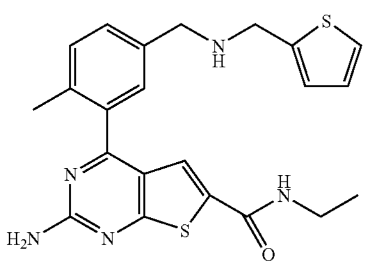 | 438 | A | Reductive amination then amide |
| 202 | 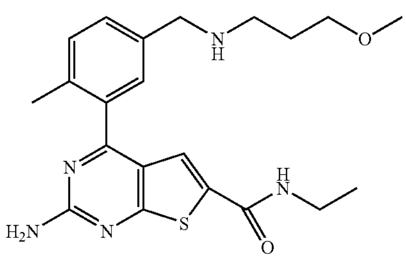 | 414 | A | Reductive amination then amide |
| 203 | 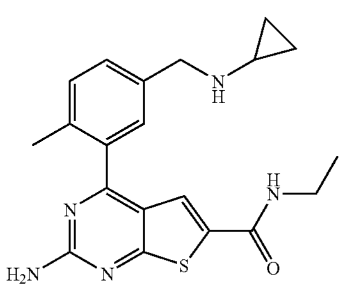 | 382 | A | Reductive amination then amide |

TABLE 5-continued

| Example | Structure | MH+ | Hsp90 FP IC50 | Synthesis Comment |
|---------|-----------|-----|---------------|-------------------|
| 204 | 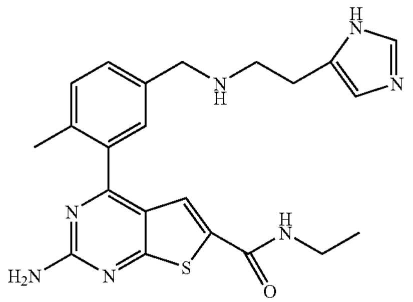 | 436 | A | Reductive amination then amide |
| 205 | 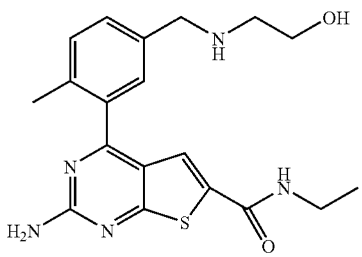 | 386 | A | Reductive amination then amide |
| 206 | 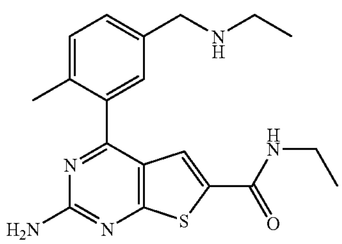 | 370 | A | Reductive amination then amide |
| 207 | 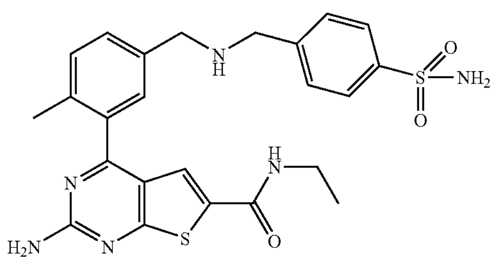 | 511 | A | Reductive amination then amide |
| 208 | 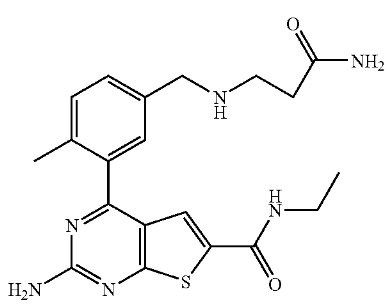 | 413 | A | Reductive amination then amide |

TABLE 5-continued

| Example | Structure | MH+ | Hsp90 FP IC50 | Synthesis Comment |
|---------|-----------|-----|---------------|-------------------|
| 209 | 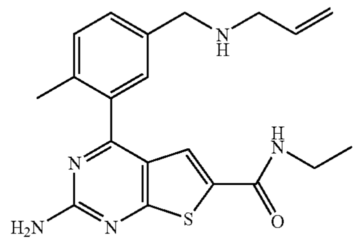 | 382 | A | Reductive amination then amide |
| 210 | 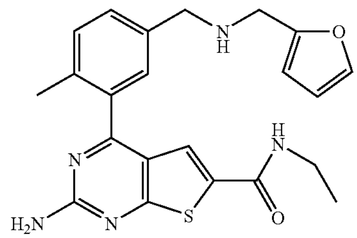 | 422 | A | Reductive amination then amide |
| 211 | 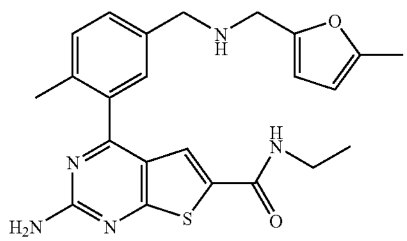 | 436 | A | Reductive amination then amide |
| 212 | 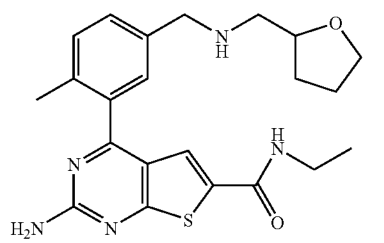 | 426 | A | Reductive amination then amide |
| 213 | 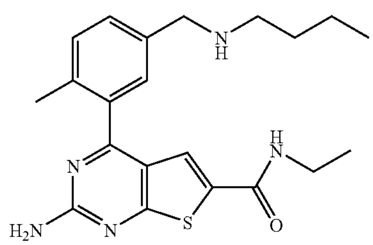 | 398 | A | Reductive amination then amide |
| 214 | 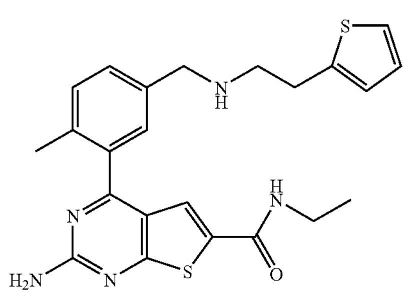 | 452 | A | Reductive amination then amide |

TABLE 5-continued

| Example | Structure | MH+ | Hsp90 FP IC50 | Synthesis Comment |
|---------|-----------|-----|---------------|-------------------|
| 215 | 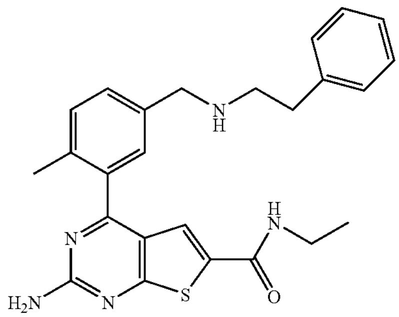 | 446 | A | Reductive amination then amide |
| 216 | 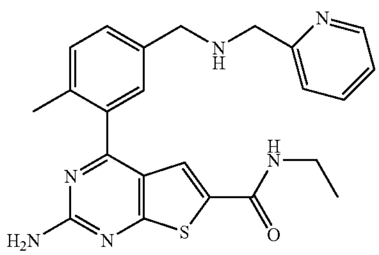 | 433 | A | Reductive amination then amide |
| 217 | 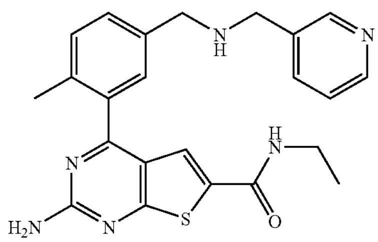 | 433 | A | Reductive amination then amide |
| 218 | 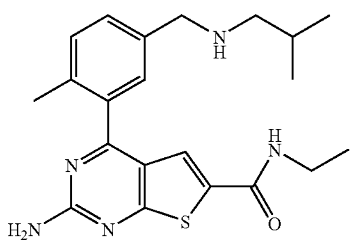 | 398 | A | Reductive amination then amide |
| 219 | 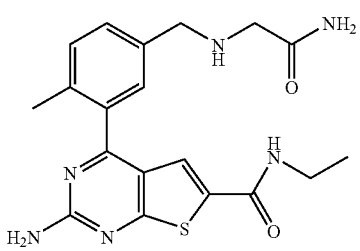 | 399 | A | Reductive amination then amide |
| 220 | 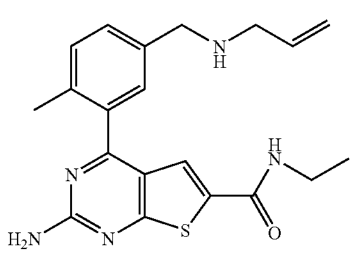 | 382 | A | Reductive amination then amide |

TABLE 5-continued

| Example | Structure | MH+ | Hsp90 FP IC50 | Synthesis Comment |
|---------|-----------|-----|---------------|-------------------|
| 221 | 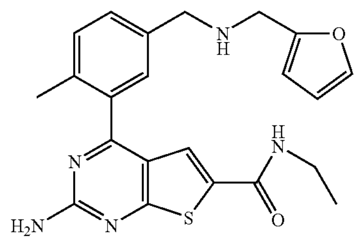 | 422 | A | Reductive amination then amide |
| 222 | 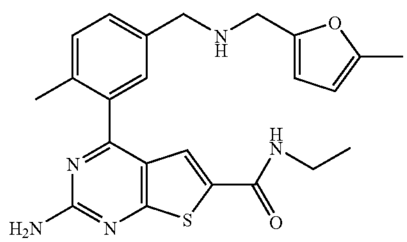 | 436 | A | Reductive amination then amide |
| 223 | 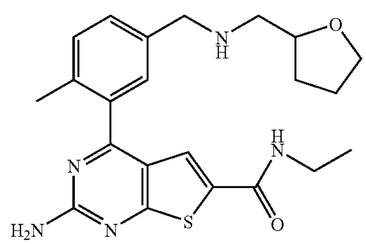 | 426 | A | Reductive amination then amide |
| 224 | 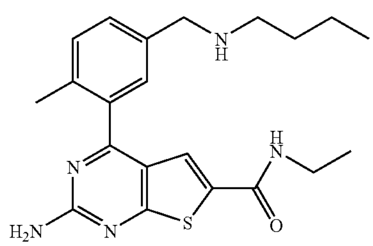 | 398 | A | Reductive amination then amide |
| 225 | 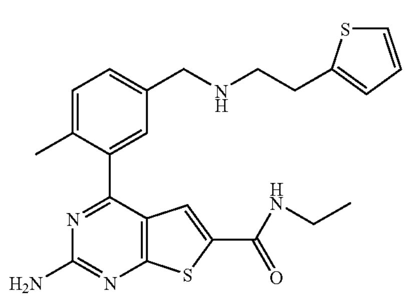 | 452 | A | Reductive amination then amide |

TABLE 5-continued

| Example | Structure | MH+ | Hsp90 FP IC50 | Synthesis Comment |
| --- | --- | --- | --- | --- |
| 226 | 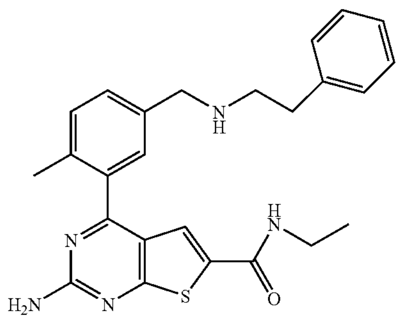 | 446 | A | Reductive amination then amide |
| 227 | 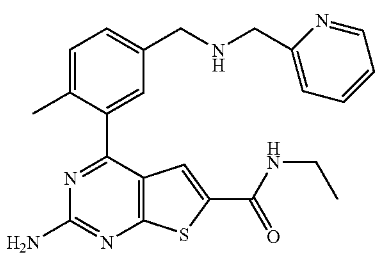 | 433 | A | Reductive amination then amide |
| 228 | 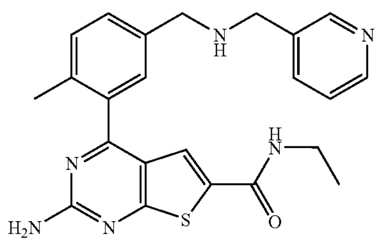 | 433 | A | Reductive amination then amide |
| 229 | 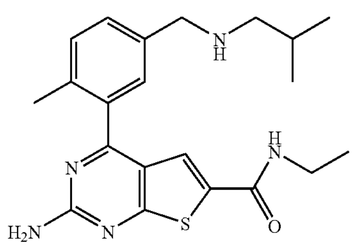 | 398 | A | Reductive amination then amide |
| 230 | 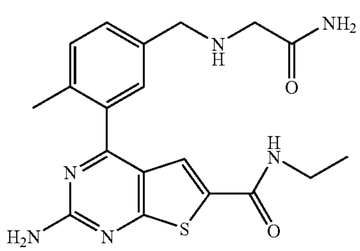 | 399 | A | Reductive amination then amide |

TABLE 5-continued

| Example | Structure | MH+ | Hsp90 FP IC50 | Synthesis Comment |
|---------|-----------|-----|---------------|-------------------|
| 231 | 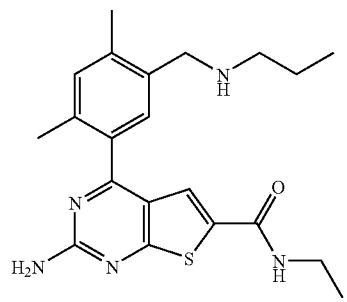 | 398 | A | Reductive amination then amide |
| 232 | 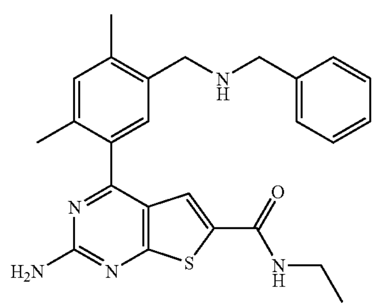 | 446 | A | Reductive amination then amide |
| 233 | 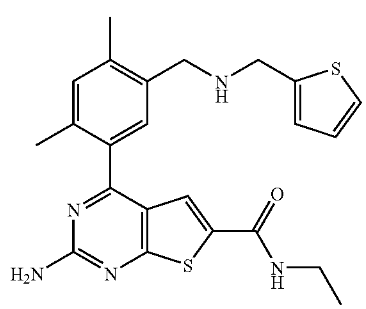 | 452 | A | Reductive amination then amide |
| 234 | 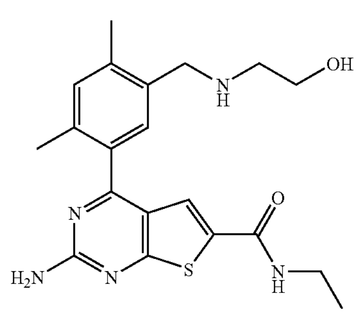 | 400 | A | Reductive amination then amide |

EXAMPLE 235

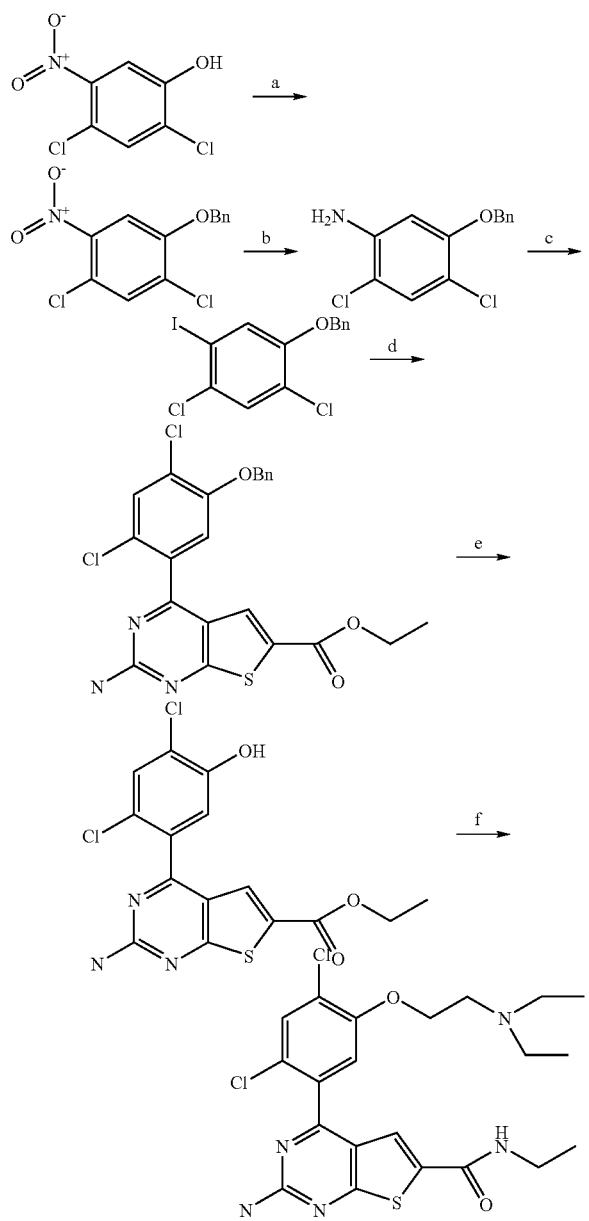

2-Amino-4-[2,4-dichloro-5-(2-diethylamino-ethoxy)-phenyl]-thieno[2,3-d]pyrimidine-6-carboxy-lic acid ethyl amide

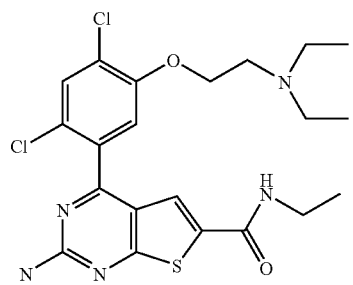

Step 1

1-Benzyloxy-2,4-dichloro-5-nitro-benzene

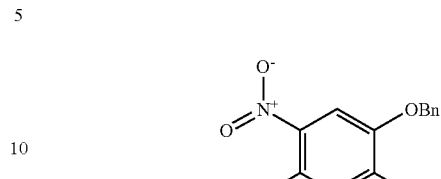

Potassium carbonate (12 g, 87 mmol) was added to a solution of the 2,4-dichloro-5-nitrophenol (15.6 g, 75 mmol) in acetone. Benzyl bromide (9 ml, 76 mmol) was added and the suspension heated, oil bath temperature 75° C., for 3 hrs. The resulting suspension was allowed to cool and water (500 ml) added, the mixture was extracted with dichloromethane (2×200 ml). The combined extracts were washed with aqueous sodium hydroxide (150 ml, 2M), water (2×200 ml) and saturated aqueous sodium chloride solution (150 ml). The solution was dried over anhydrous sodium sulphate and concentrated to a pale yellow solid (21.5 g, 96%)

$R_f$ 0.73 $CH_2Cl_2$ ($SiO_2$)

Step 2

5-Benzyloxy-2,4-dichloro-phenylamine

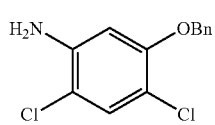

Iron powder (21 g, 376 mmol) was added to a suspension of the nitrobenzene (21.5 g, 72 mmol) in acetic acid (300 ml)/water (150 ml) and the mixture heated, oil bath temperature 85° C., for ~90 mins. The resulting suspension was filtered. The filtrate was allowed to cool, water (750 ml) was added and the mixture extracted with dichloromethane (3×150 ml). The combined extracts were washed with aqueous sodium hydroxide (300 ml, 2M), water (2×500 ml) and saturated aqueous sodium chloride solution (200 ml). The solution was dried over anhydrous sodium sulphate and concentrated to a pale brown solid (18.6 g, 96%)

$R_f$ 0.57 $CH_2Cl_2$ ($SiO_2$)

Step 3

1-Benzyloxy-2,4-dichloro-5-iodo-benzene

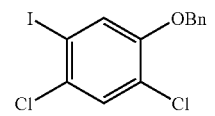

Hydrochloric acid (60 ml, 6M) was added to a solution of the aniline (16.2 g, 60 mmol) in acetic acid (240 ml) and the resulting suspension cooled (ice/water/salt). Aqueous sodium nitrite (4.8 g, 69.5 mmol in 40 ml) was added slowly (keeping the temperature <5° C.). On complete addition the resulting solution was stirred for ~30 mins.

The resulting solution was poured into a solution of potassium iodide (20 g, 120 mmol) and iodine (4 g, 16 mmol) in water (200 ml), and the mixture stirred for ~90 mins. Water (800 ml) was added and the mixture extracted with dichloromethane (3×250 ml). The combined extracts were washed with aqueous sodium thiosulphate solution (2×150 ml, 10%), aqueous sodium hydroxide (250 ml, 2M), water (2×250 ml) and saturated aqueous sodium chloride solution (200 ml). The solution was dried over anhydrous sodium sulphate and concentrated to a pale brown oil, solidified on standing. (20.6 g, 90%)

$R_f$ 0.82 $CH_2Cl_2$ ($SiO_2$)

Step 4

2-Amino-4-(5-benzyloxy-2,4-dichloro-phenyl)-thieno[2,3-d]pyrimidine-6-carboxylic acid ethyl ester

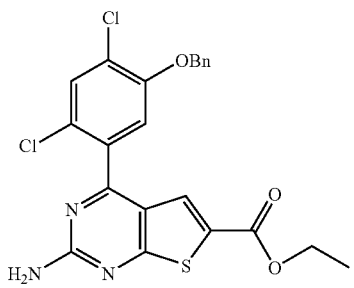

Potassium acetate (16 g, 163 mmol) was added to a solution of the iodobenzene (20.6 g, 54 mmol) and bis(pinacolato) diboron (14.5 g, 57 mmol) in DMF (50 ml), under a nitrogen atmosphere. Palladium acetate (450 mg, cat.) was added and the mixture heated, oil bath temperature 90° C., for ~18 hrs. The resulting solution was concentrated, and the residue taken up in ethyl acetate (200 ml), the solution was washed with water (3×200 ml) and saturated aqueous sodium chloride solution (150 ml). The solution was dried over anhydrous sodium sulphate and concentrated to a pale brown gum. The residue was taken up in 1,4-dioxan (160 ml) and 2-Amino-4-chloro-thieno[2,3-d]pyrimidine-6-carboxylic acid ethyl ester (12.85 g, 50 mmol) and aqueous potassium phosphate (40 ml, 2M) added, under a nitrogen atmosphere. Dichloro bis(triphenylphosphine) palladium(II) (cat.) was added and the mixture heated, oil bath temperature 100° C., for ~3 hrs. The mixture was allowed to cool and ethyl acetate (400 ml) added. The mixture was washed with saturated aqueous sodium chloride solution (100 ml). The solution was dried over anhydrous sodium sulphate and concentrated to a pale yellow solid. Solids were washed with diethyl ether/hexane (1:1), to give an off-white solid. Dried in vacuo (40° C.). 10.7 g (45%)

$R_f$ 0.13 EtOAc/Hex (1:3) ($SiO_2$)

LC retention time 2.891 min [M+H]$^+$ 474.1/476.1 (run time 3.75 min)

Step 5

2-Amino-4-(2,4-dichloro-5-hydroxy-phenyl)-thieno[2,3-d]pyrimidine-6-carboxylic acid ethyl amide

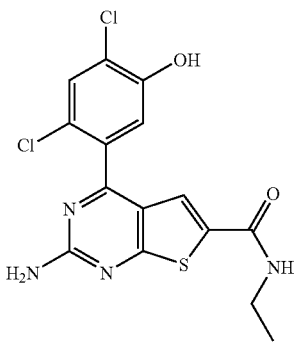

A suspension of 2-Amino-4-(5-benzyloxy-2,4-dichlorophenylthieno[2,3-d]pyrimidine-6-carboxylic acid ethyl ester in methanolic ethylamine (~2M) was heated, at ~75° C., for ~18 hrs. The resulting solution was concentrated and the residue triturated with diethyl ether/hexane to give a pale brown powder.

LC retention time 2.654 minutes [M+H]$^+$ 475.1/473.1 (Run time 3.75 mins)

Boron trichloride solution (1M in dichloromethane) was added to a suspension of 2-Amino-4-(5-benzyloxy-2,4-dichlorophenyl)-thieno[2,3-d]pyrimidine-6-carboxylic acid ethyl amide in dichloromethane, at −78° C. under a nitrogen atmosphere. The suspension was stirred for ~3 hrs at room temperature. The suspension was cooled in ice and methanol added, the resulting mixture was stirred for ~1 hr. and concentrated to a yellow green solid. The solids were suspended in aqueous sodium acetate (10%) and extracted with ethyl acetate. The extracts were washed with water and saturated aqueous sodium chloride solution. The solution was dried over anhydrous sodium sulphate and concentrated to a pale brown solid, washed with hexane dried in vacuo.

LC retention time 2.180 minutes [M+H]$^+$ 385/383 (Run time 3.75 mins)

Step 6

2-Amino-4-[2,4-dichloro-5-(2-diethylamino-ethoxy)-phenyl]-thieno[2,3-d]pyrimidine-6-carboxylic acid ethyl amide

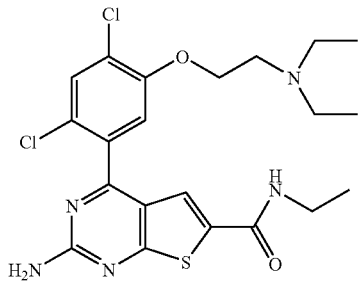

Cesium carbonate was added to a solution of 2-Amino-4-(2,4-dichloro-5-hydroxyphenyl)-thieno[2,3-d]pyrimidine-6-carboxylic acid ethyl amide in DMF, 2-Bromo-N,N-diethylethylamine hydrobromide was added and the suspension heated, at ~140° C., for ~2 hrs. The resulting suspension was allowed to cool and dichloromethane added. The mixture was washed with water and saturated aqueous sodium chloride solution. The solution was dried over anhydrous sodium sulphate and concentrated to a dark brown gum. The crude product was purified by chromatography on silica eluting with mixtures of dichloromethane and methanol.

$^1$H NMR (400 MHz, d$_6$-DMSO) δ 0.96 (t, 6H, J=7.1 Hz), 1.07 (t, 3H, J=7.2 Hz), 2.55 (q, 4H, J=7.1 Hz), 2.81 (t, 2H, J=5.8 Hz), 3.22 (m, 2H), 4.12 (t, 2H, J=5.8 Hz), 7.23 (s, 2H), 7.38 (s, 1H), 7.57 (s, 1H), 7.80 (s, 1H), 8.54 (t, 1H, J=5.5 Hz)

LC retention time 1.774 minutes [M+H]$^+$ 484/482 (Run time 3.75 mins)

This compound had activity A in the fluorescence polarization assay described below.

EXAMPLE 236

2-Amino-4-[2,4-dichloro-5-(2-morpholin-4-yl-ethoxy)-phenyl]-thieno[2,3-d]pyrimidine-6-carboxylic acid ethyl amide

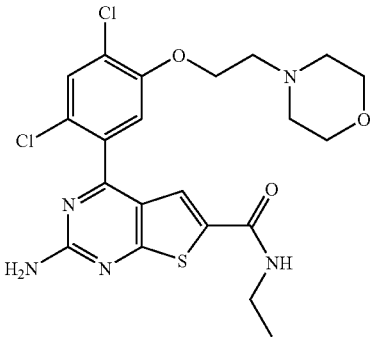

Step 1

2-Amino-4-[2,4-dichloro-5-(2,2-diethoxy-ethoxy)-phenyl]-thieno[2,3-d]pyrimidine-6-carboxylic acid ethyl amide

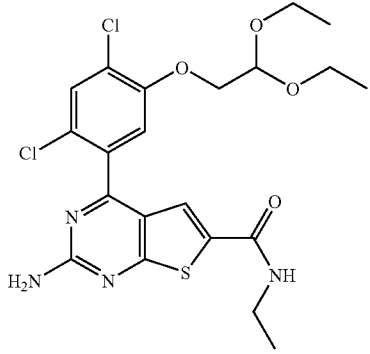

Potassium tert-butoxide was added to a suspension of 2-Amino-4-(2,4-dichloro-5-hydroxyphenyl)-thieno[2,3-d]pyrimidine-6-carboxylic acid ethyl amide in acetonitrile, bromoacetaldehyde diethyl acetal was added and the suspension heated under reflux for ~8 hrs. The resulting suspension was allowed to cool and water added, the mixture was extracted with ethyl acetate and the extracts washed with water and saturated aqueous sodium chloride solution. The solution was dried over anhydrous sodium sulphate and concentrated to a red/brown gum. The crude product was purified by chromatography on silica eluting with mixtures of ethyl acetate and hexane.

LC retention time 2.614 minutes [M+H]$^+$ 501/499 (Run time 3.75 mins)

Step 2

2-Amino-4-[2,4-dichloro-5-(2-morpholin-4-yl-ethoxy)-phenyl]-thieno[2,3-d]pyrimidine-6-carboxylic acid ethyl amide Hydrochloric acid was added to a solution of 2-Amino-4-(2,4-dichloro-5-(2,2-diethoxyethoxy)-phenyl)-thieno[2,3-d]pyrimidine-6-carboxylic acid ethyl amide in THF and the solution stirred for ~18 hrs. Morpholine was added and the solution stirred, sodium triacetoxyborohydride was added and the resulting suspension stirred for ~18 hrs. Dichloromethane was added and the mixture washed with aqueous ammonia (0.880), water and saturated aqueous sodium chloride solution. The solution was dried over anhydrous sodium sulphate and concentrated to a pale yellow solid. The crude product was purified by chromatography on silica eluting with mixtures of ethyl acetate and hexane.

LC retention time 1.795 minutes [M+H]$^+$ 498/496 (Run time 3.75 mins)

This compound had activity A in the fluorescence polarization assay described below.

EXAMPLE 237

2-Amino-4-[2,4-dichloro-5-(2-diethylamino-ethoxy)-phenyl]-thieno[2,3-d]pyrimidine-6-carboxylic acid isopropyl amide

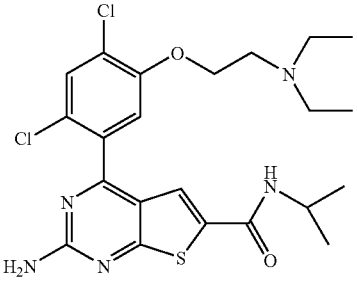

Step 1

2-Amino-4-(5-benzyloxy-2,4-dichloro-phenyl)-thieno[2,3-d]pyrimidine-6-carboxylic acid

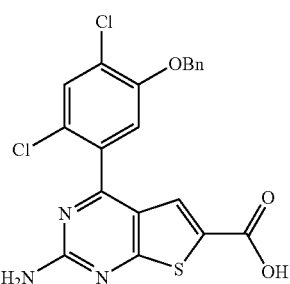

Sodium hydroxide (0.190 g; 4.75 mmol) was added to 2-Amino-4-(5-benzyloxy-2,4-dichloro-phenyl)-thieno[2,3-d]pyrimidine-6-carboxylic acid ethyl ester (step 4 example 235). Ethanol (25 ml) was added followed by water (2.5 ml) and the reaction mixture was heated to reflux for 1 hour. The reaction mixture was allowed to cool and solvents were removed in vacuo. The resulting residue was dissolved in water and stirred in ice-water bath and the neutralised by the drop-wise addition of 37% (aq) hydrochloric acid solution. The reaction mixture was freeze dried to afford product as a yellow powder (containing 2 equivalents of NaCl) 1.33 g; 100%.

LC retention time 2.579 minutes [M+H]$^+$ 448/446 (Run time 3.75 mins)

Step 2

2-Amino-4-(5-benzyloxy-2,4-dichloro-phenyl)-thieno[2,3-d]pyrimidine-6-carboxylic acid isopropylamide

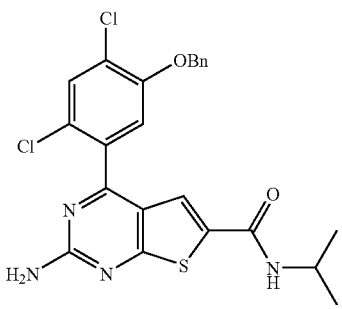

O-(7-azabenzotriazol-1-yl)-N,N,N',N'-tetramethyluronium hexafluorophosphate (1.176 g; 3.07 mmol) was added to 2-Amino-4-(5-benzyloxy-2,4-dichloro-phenyl)-thieno[2,3-d]pyrimidine-6-carboxylic acid.2NaCl (1.33 g; 2.38 mmol) then DMF (25 ml) was added to afford a turbid brown solution. Isopropylamine (1.01 ml; 11.9 mmol) was added and reaction mixture was heated at 60° C. (oil bath temperature) for 18 hours. Reaction mixture was allowed to cool to room temperature and DMF was removed in vacuo. The residue was partitioned between ethyl acetate (200 ml) and water (200 ml). The phases were separated and the organic phase was washed with saturated aqueous sodium chloride solution (200 ml) the dried over anhydrous sodium sulphate, filtered and the filtrate solvents removed in vacuo to afford a yellow solid. The crude product was purified by flash chromatography on silica gel (50 g IST Flash Si cartridge) eluting with a solvent gradient of 20 to 50% ethyl acetate in hexane. This affords product as a colourless solid (0.612 g; 53%)

LC retention time 2.756 minutes [M+H]$^+$ 489/487 (Run time 3.75 mins)

Step 3

2-Amino-4-(2,4-dichloro-5-hydroxy-phenyl)-thieno[2,3-d]pyrimidine-6-carboxylic acid isopropylamide

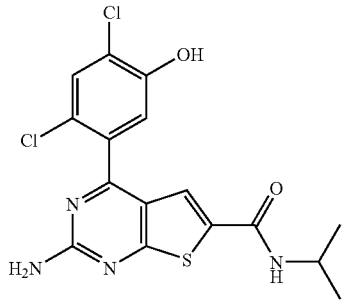

Prepared as for step 5 example 235 from 2-Amino-4-(5-benzyloxy-2,4-dichloro-phenyl)-thieno[2,3-d]pyrimidine-6-carboxylic acid isopropylamide (0.594 g). Product was purified by flash chromatography on silica gel (20 g IST Flash Si cartridge) eluting with a solvent gradient of 20 to 100% ethyl acetate in hexane. This affords product as a colourless solid (0.350 g; 72%)

LC retention time 2.353 minutes [M+H]$^+$ 399/397 (Run time 3.75 mins)

2-Amino-4-[2,4-dichloro-5-(2-diethylamino-ethoxy)-phenyl]-thieno[2,3-d]pyrimidine-6-carboxylic acid isopropyl amide

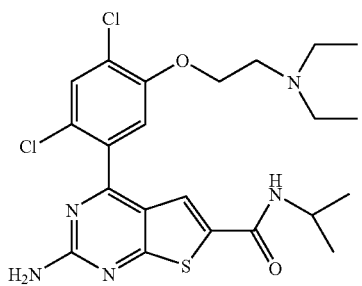

Prepared as for step 6 of example 235 from 2-Amino-4-(2,4-dichloro-5-hydroxy-phenyl)-thieno[2,3-d]pyrimidine-6-carboxylic acid isopropylamide (0.100 g). Product was purified by preparative HPLC.

LC retention time 1.965 minutes [M+H]$^+$ 498/496 (Run time 3.75 mins)

This compound had activity A in the fluorescence polarization assay described below.

The following compounds (Table 6) were made utilising the methods of examples 235, 236 and 237

The fourth column of Table 6 states the activity of the compound in the fluorescence polarization assay described below.

TABLE 6

| Example | Structure | MH+ | Hsp90 FP IC50 | Synthesis Comment |
|---|---|---|---|---|
| 238 | 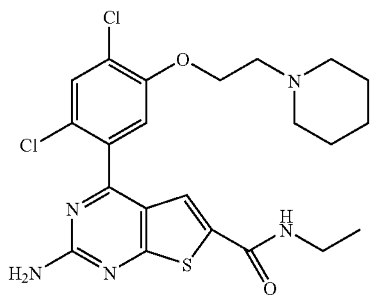 | 494 | A | Reductive amination |
| 239 | 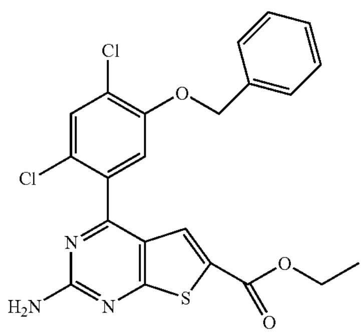 | 474 | A | Suzuki |
| 240 | 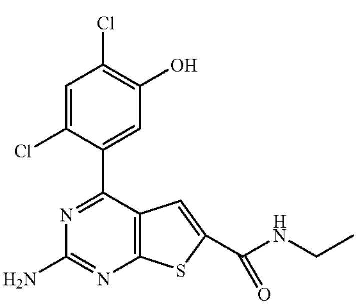 | 383 | A | Amide then debenzylation |
| 241 | 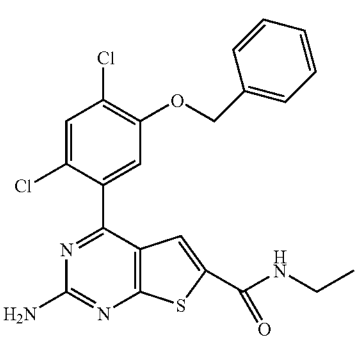 | 473 | A | Suzuki then amide |

TABLE 6-continued

| Example | Structure | MH+ | Hsp90 FP IC50 | Synthesis Comment |
|---|---|---|---|---|
| 242 | 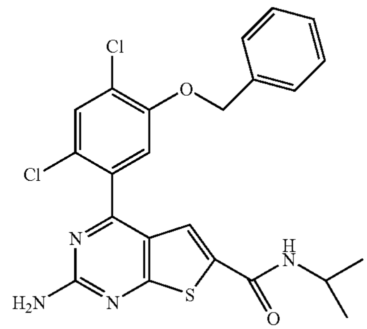 | 487 | A | Suzuki then amide |
| 243 | 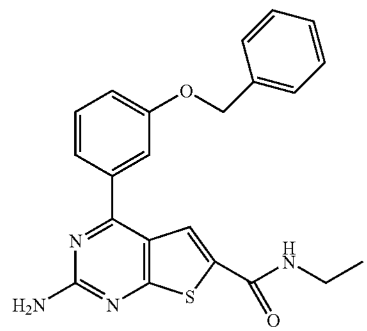 | 405 | A | Suzuki then amide |
| 244 | 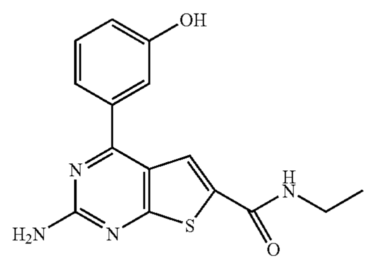 | 315 | A | Amide then debenzylation |
| 245 | 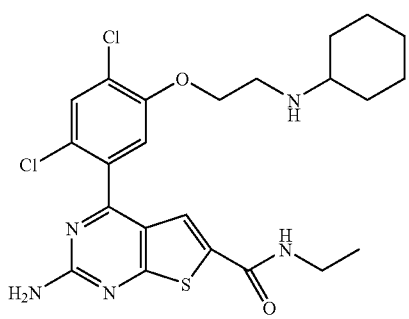 | 508 | A | Reductive amination |
| 246 | 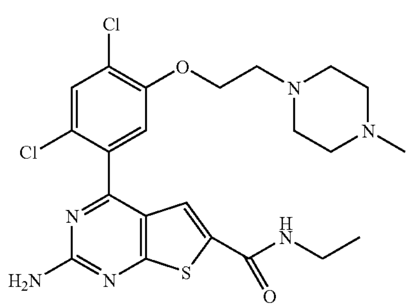 | 509 | A | Reductive amination |

TABLE 6-continued

| Example | Structure | MH+ | Hsp90 FP IC50 | Synthesis Comment |
|---------|-----------|-----|---------------|-------------------|
| 247 | 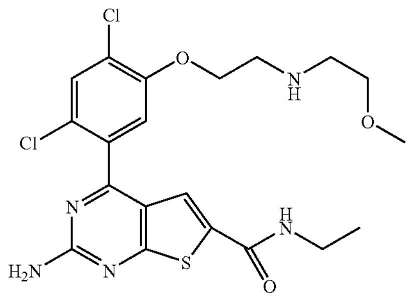 | 484 | A | Reductive amination |
| 248 | 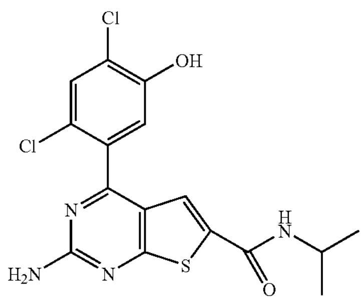 | 397 | A | Amide then debenzylation |
| 249 | 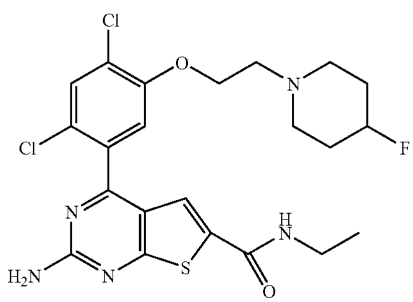 | 512 | A | Reductive amination |
| 250 | 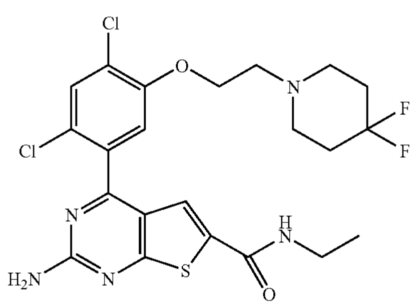 | 530 | A | Reductive amination |
| 251 | 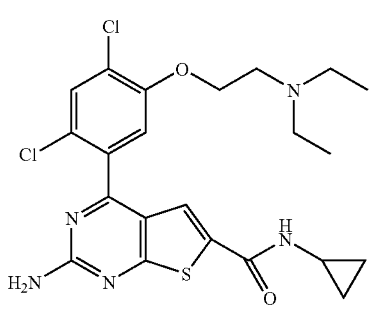 | 494 | A | Alkylation then amide |

TABLE 6-continued
| Example | Structure | MH+ | Hsp90 FP IC50 | Synthesis Comment |
|---------|-----------|-----|---------------|-------------------|
| 252 | 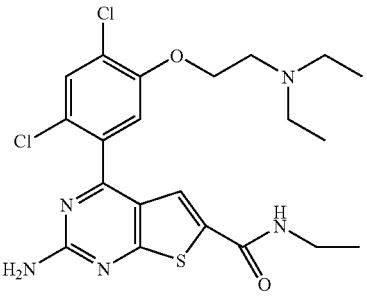 | 536 | A | Alkylation then amide |
| 253 | 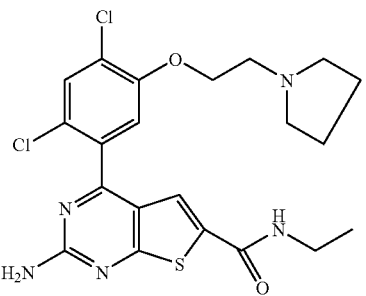 | 480 | A | Amide then alkylation |
| 254 | 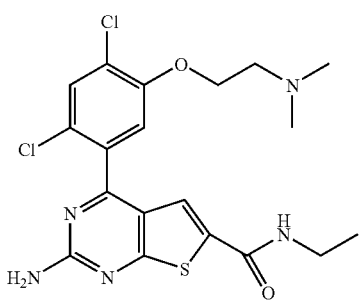 | 454 | A | Amide then alkylation |
| 255 | 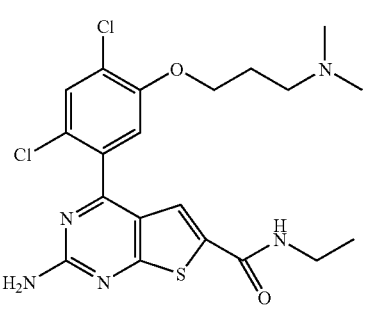 | 468 | A | Amide then alkylation |
| 256 | 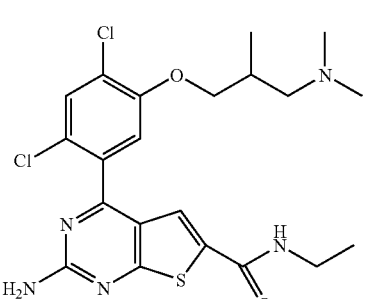 | 482 | A | Amide then alkylation |

TABLE 6-continued

| Example | Structure | MH+ | Hsp90 FP IC50 | Synthesis Comment |
|---|---|---|---|---|
| 257 | 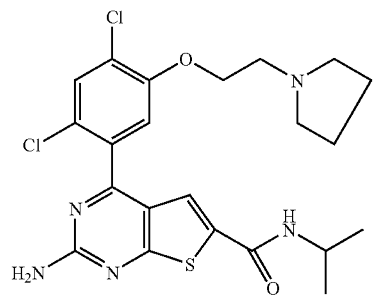 | 494 | A | Amide then alkylation |
| 258 | 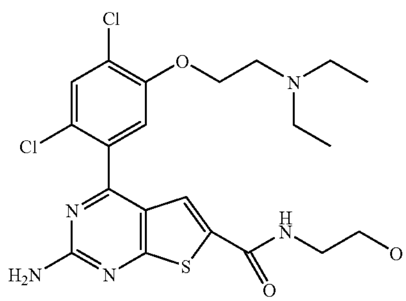 | 498 | A | Alkylation then amide |
| 259 | 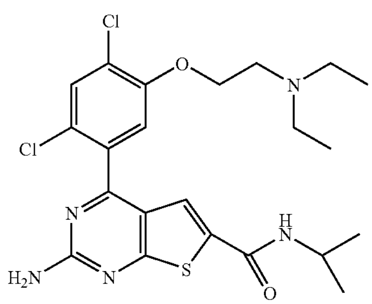 | 496 | A | Amide then alkylation |
| 260 | 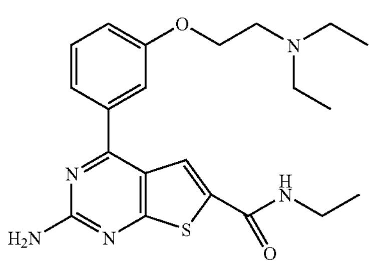 | 414 | A | Amide then alkylation |
| 261 | 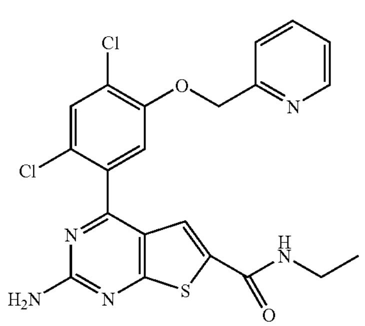 | 474 | A | Amide then alkylation |

TABLE 6-continued

| Example | Structure | MH+ | Hsp90 FP IC50 | Synthesis Comment |
|---------|-----------|-----|---------------|-------------------|
| 262 | 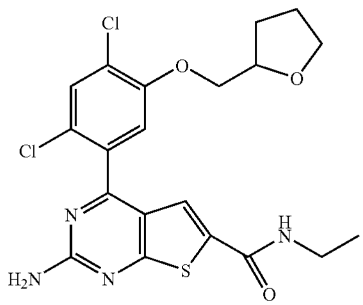 | 467 | A | Amide then alkylation |
| 263 | 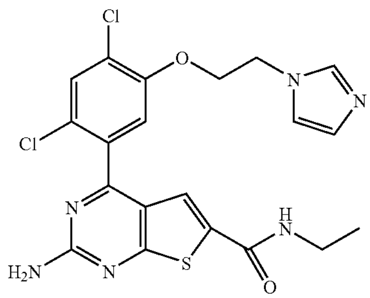 | 477 | A | Amide then alkylation |
| 264 | 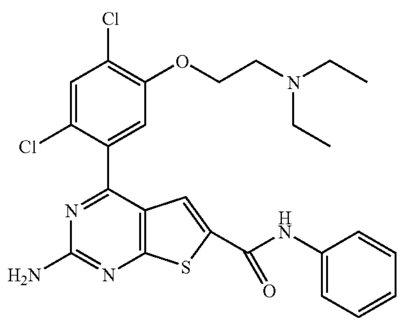 | 440 | A | Alkylation then amide |
| 265 | 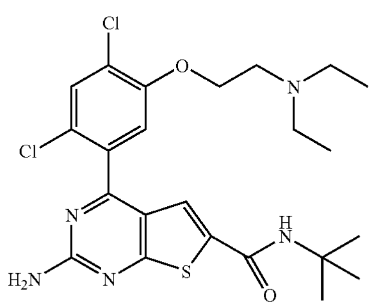 | 510 | A | Alkylation then amide |
| 266 | 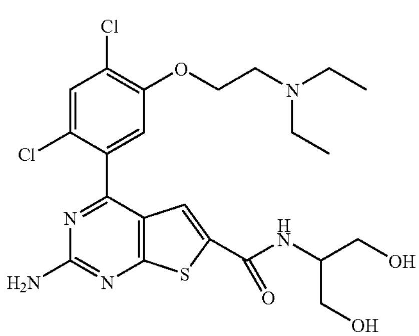 | 428 | A | Alkylation then amide |

TABLE 6-continued

| Example | Structure | MH+ | Hsp90 FP IC50 | Synthesis Comment |
|---------|-----------|-----|---------------|-------------------|
| 267 | 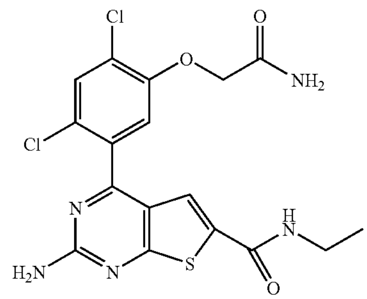 | 440 | A | Amide then alkylation |
| 268 | 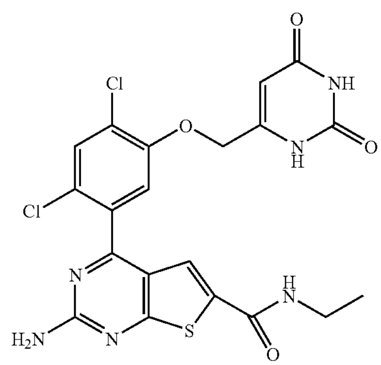 | 507 | A | Amide then alkylation |
| 269 | 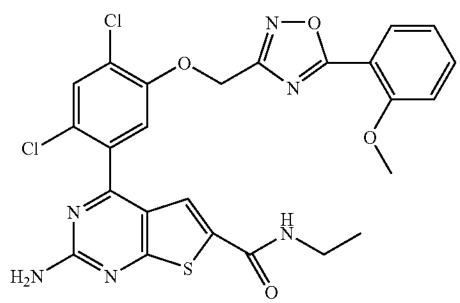 | 571 | A | Amide then alkylation |
| 270 | 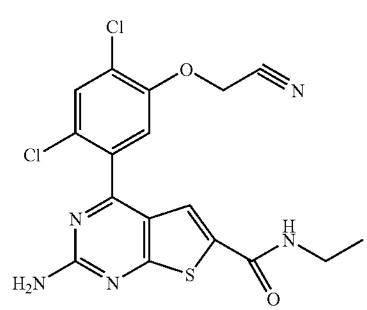 | 422 | A | Amide then alkylation |

TABLE 6-continued

| Example | Structure | MH+ | Hsp90 FP IC50 | Synthesis Comment |
|---|---|---|---|---|
| 271 | 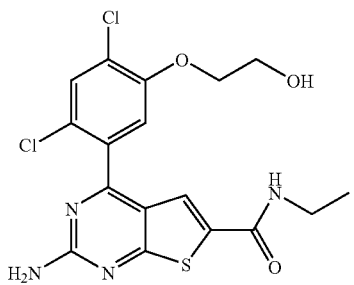 | 510 | A | Amide then alkylation |

EXAMPLE 272

2-Amino-4-[2,4-dichloro-5-(2-hydroxy-ethoxy)-phenyl]-thieno[2,3-d]pyrimidine-6-carboxylic acid ethylamide

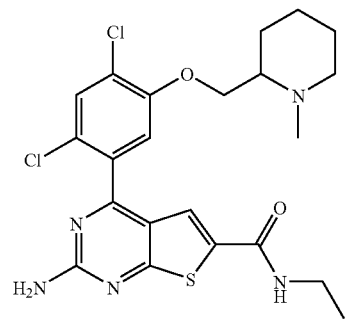

Hydrochloric acid was added to a solution of 2-Amino-4-(2,4-dichloro-5-(2,2-diethoxyethoxy)-phenyl)-thieno[2,3-d]pyrimidine-6-carboxylic acid ethyl amide in THF and the solution stirred for ~18 hrs. Dichloromethane was added and the mixture stirred, sodium borohydride was added and the resulting suspension stirred for ~5 hrs. Dichloromethane was added and the mixture washed with saturated ammonium chloride solution. The solution was dried over anhydrous sodium sulphate and concentrated to a pale yellow solid. The crude product was purified by preparative HPLC, to give the product as an off-white solid.

LC retention time 2.124 minutes [M+H]$^+$ 428.9/426 (Run time 3.75 mins)

EXAMPLE 273

2-Amino-4-[2,4-dichloro-5-(1-methyl-piperidin-2-ylmethoxy)-phenyl]-thieno[2,3d]pyrimidine-6-carboxylic acid ethylamide To a mixture of 2-Amino-4-(2,4-dichloro-5-hydroxy-phenyl)-thieno[2,3d]pyrimidine-6-carboxylic acid ethylamide (30 mg, 0.08 mmol) and (1-Methyl-piperidin-2-yl)-methanol (12 mg, 0.09 mmol) in dry tetrahydrofuran (10 ml) was added triphenylphosphine (33 mg, 0.13 mmol). Diethylazodicarboxylate (0.021 ml, 0.13 mmol) in dry tetrahydrofuran (1 ml) was added drop-wise over the space of 30 seconds at room temperature. The mixture was then stirred at room temperature for 30 minutes at which time ethyl acetate (30 ml) was added and the resultant solution was washed with 1M sodium bicarbonate solution (30 ml), followed by saturated brine (30 ml). The resultant organics were dried with sodium sulphate and concentrated to give a yellow oil which was purified by preparative LCMS, yielding a white solid (20.4 mg, 53%).

LC retention time 1.84 minutes, [M+H]$^+$ 494.

This compound had activity A in the fluorescence polarization assay described below.

EXAMPLE 274

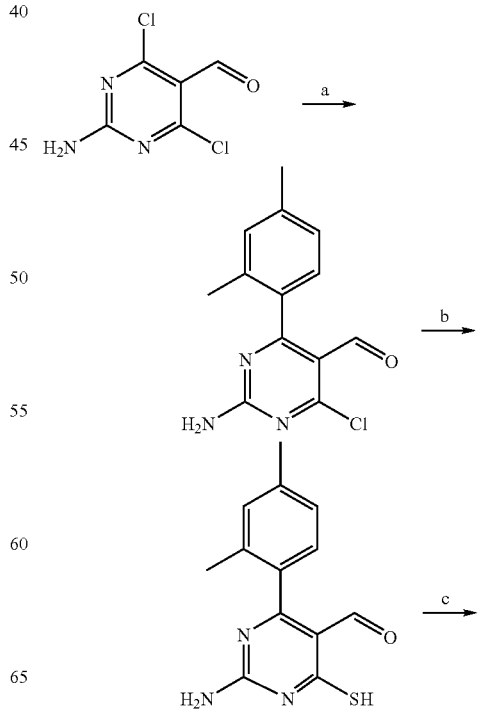

-continued

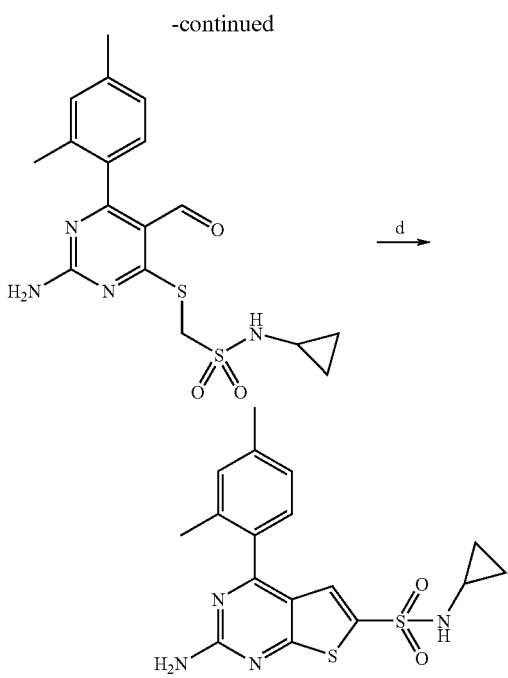

2-Amino-4-(2,4-dimethyl-phenyl)-thieno[2,3-d]pyrimidine-6-sulfonic acid cyclopropylamide

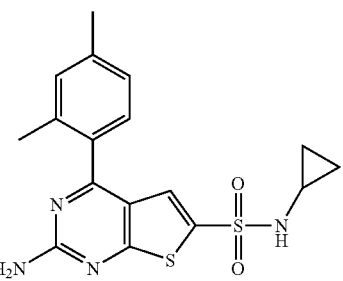

Step 1

2-Amino-4-chloro-6-(2,4-dimethyl-phenyl)-pyrimidine-5-carbaldehyde

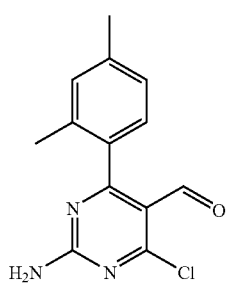

Aqueous potassium phosphate was added to a suspension of 2,4-dimethylbenzene boronic acid and 2-amino-4,6-dichloro-5-pyrimidinecarbaldehyde (3 eq) in 1,4-dioxan, under a nitrogen atmosphere. Dichloro bis(triphenylphosphine)palladium (II) (cat.) was added and the mixture heated, ~100° C., for ~90 mins. The resulting mixture was allowed to cool and dichloromethane added, the mixture was washed with water and saturated aqueous sodium chloride solution. The solution was dried over anhydrous sodium sulphate and concentrated to a pale yellow solid. The crude solid was purified by column chromatography on silica eluting with mixtures of diethyl ether and hexane.

LC retention time 2.354 minutes [M+H]$^+$ 262.0 (Run time 3.75 mins)

Step 2

2-Amino-4-(2,4-dimethyl-phenyl)-6-mercapto-pyrimidine-5-carbaldehyde

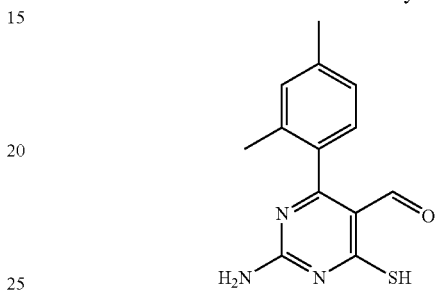

2-Amino-4-chloro-6-(2,4-dimethylphenyl)-pyrimidine-5-carbaldehyde was added to a suspension of sodium sulphide (5 eq.) in DMF and the mixture stirred for ~60 mins, to give a yellow suspension. The suspension was poured into water, and the solution filtered. The filtrate was acidified with acetic acid, to give a yellow precipitate. The solids were removed by filtration and washed with water and hexane, dried in vacuo, to give a yellow powder.

LC retention time 2.048 minutes [M+H]$^+$ 260.0 (Run time 3.75 mins)

Step 3

C-[2-amino-6-(2,4-dimethyl-phenyl)-5-formyl-pyrimidin-4-ylsulfanyl]-N-cyclopropyl-methanesulfonamide

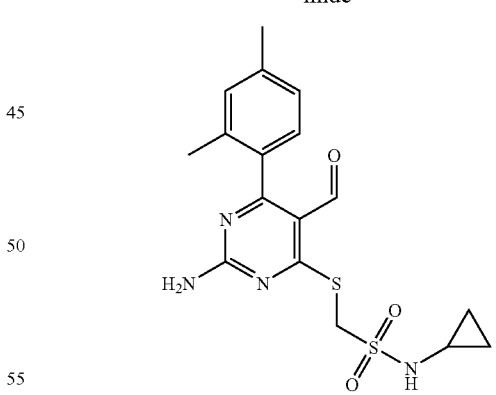

Sodium hydrogen carbonate was added to a solution of 2-Amino-4-(2,4-dimethylphenyl)-6-mercapto-pyrimidine-5-carbaldehyde in DMF and the suspension stirred. C-bromo-N-cyclopropyl-methane sulphonamide was added, and the mixture heated, ~85° C., for ~3 hrs. The resulting suspension was allowed to cool and ethyl acetate added, the mixture was washed with water and saturated aqueous sodium chloride solution. The solution was dried over anhydrous sodium sulphate and concentrated to a pale yellow solid. The crude solid was purified by column chromatography on silica eluting with mixtures of ethyl acetate and hexane.

LC retention time 2.413 minutes [M+H]+ 393.0 (Run time 3.75 mins)

Step 4

2-Amino-4-(2,4-dimethyl-phenyl)-thieno[2,3-d]pyrimidine-6-sulfonic acid cyclopropylamide

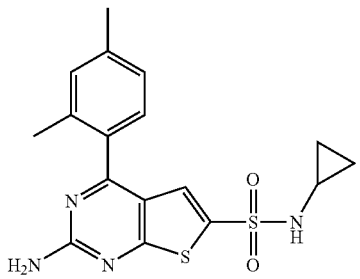

Pyridine was added to a suspension of C-[2-Amino-6-(2,4-dimethylphenyl)-5-formyl-pyrimidin-4-ylsulphanyl]-N-cyclopropyl-methane sulphonamide in dichloromethane and the mixture cooled, ice/water. Trifluoroacetic anhydride was added and the mixture stirred for ~2 hrs and heated under reflux for ~24 hrs. The resulting dark red solution was allowed to cool and aqueous ammonia (0.880) added and the mixture stirred for ~30 mins. Dichloromethane was added and the mixture washed with dilute hydrochloric acid, water and saturated aqueous sodium chloride solution. The solution was dried over anhydrous sodium sulphate and concentrated to a red/orange solid. The crude solid was purified by preparative HPLC.

$^1$H NMR (400 MHz, $d_6$-DMSO) δ 0.40-0.45 (m, 2H), 0.50-0.55 (m, 2H), 2.22 (s, 3H), 2.27 (m, 1H), 2.36 (s, 3H), 7.17 (bd, 1H, J=7.6 Hz), 7.18 (s, 1H), 7.21 (bs, 1H), 7.28 (d, 1H, J=7.6 Hz), 7.34 (s, 2H), 8.16 (bs, 1H)

LC retention time 2.478 minutes [M+H]+ 375.0 (Run time 3.75 mins)

This compound had activity A in the fluorescence polarization assay described below.

EXAMPLE 275

2-Amino-4-phenethyl-thieno[2,3-d]pyrimidine-6-carboxylic acid ethyl ester

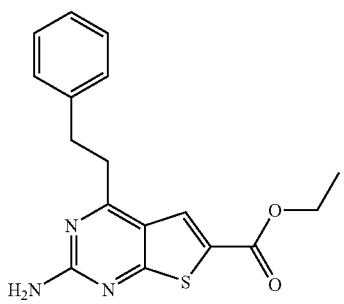

Step 1

2-Amino-4-styryl-thieno[2,3-d]pyrimidine-6-carboxylic acid ethyl ester

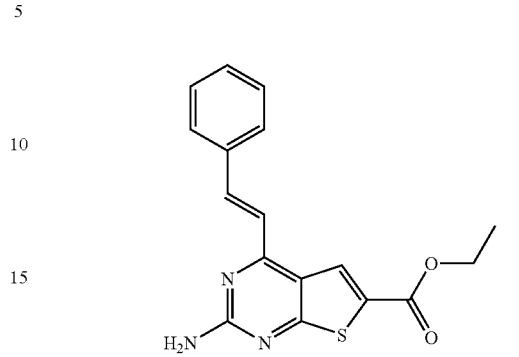

To a solution of 2-amino-4-chloro-thieno[2,3-d]pyrimidine-6-carboxylic acid ethyl ester (0.193 g, 0.75 mmol.) and alpha-phenyl vinyl boronic acid (0.17 g, 1.5 equiv.) in DMF at room temperature was added 1M sodium hydrogen carbonate solution (1.88 ml, 2.5 equiv) followed by bis(triphenylphosphine)palladium (II) chloride (26 mg, 0.05 equiv.). Nitrogen was bubbled through the mixture for 5 minutes before heating to 85° C. and stirring for 10 hours. The cooled solution was partitioned between ethyl acetate and water, the combined organics washed with water and brine before being loaded directly on to an Isolute SCX II ion exchange column. On elution with 1M Ammonia in methanol and evaporation in vacuo, pure product was recovered as an orange powder (0.169 g, 70%)

$^1$H NMR (CDCl$_3$) δ=8.03 (1H, s); 8.03 (1H, d, J=15 Hz); 7.59 (2H, m); 7.41-7.30 (4H, m); 5.19 (2H, broad s); 4.31 (2H, q, J=7.1 Hz) and 1.35 (3H, t, J=7.1 Hz).

LCMS retention time 7.47 mins, [M+H]+=326.12 (run time 15 minutes)

This compound had activity 'A' in the fluorescence polarization assay described below.

Step 2

2-Amino-4-phenethyl-thieno[2,3-d]pyrimidine-6-carboxylic acid ethyl ester

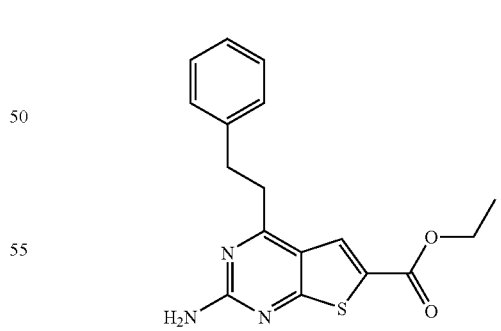

To a solution of 2-amino-4-styryl-thieno[2,3-d]pyrimidine-6-carboxylic acid ethyl ester (78 mg, 0.18 mmol) in ethanol was added 5% palladium on activated charcoal (51 mg) which was stirred overnight under a hydrogen atmosphere. The suspension was filtered through celite, the volatiles removed in vacuo and the residue purified using semi-preparative HPLC to yield the pure compound as an orange powder.

¹H NMR (CDCl₃) δ=7.82 (1H, s); 7.35-7.11 (5H, m); 5.33 (2H, broad s); 4.40 (2H, q, J=7.1 Hz); 3.26 (2H, m); 3.22 (2H, m) and 1.43 (3H, t, J=7.1 Hz).

LCMS retention time 7.11 mins, [M+H]⁺=327.92 (run time 15 minutes)

This compound had activity 'A' in the fluorescence polarization assay described below.

The following compounds (Table 7) were made by the methods of Example 275 substituting the appropriate boronic acid or boronate ester. The corresponding amides were synthesised directly from the ester (example 235, step 5) or by hydrolysis (example 43, step 1) followed by amine coupling (example 43, step 2) and purified by semi-preparative HPLC. The fourth column of Table 7 states the activity of the compound in the fluorescence polarization assay described below.

TABLE 7

| Example | Structure | MH+ | Hsp90 FP IC50 | Synthesis Comment |
|---------|-----------|------|---------------|-------------------|
| 276 | 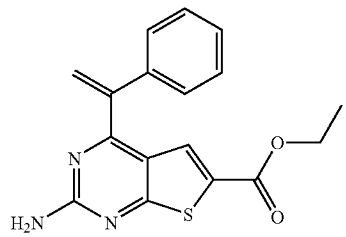 | 326.1 | A | Suzuki |
| 277 | 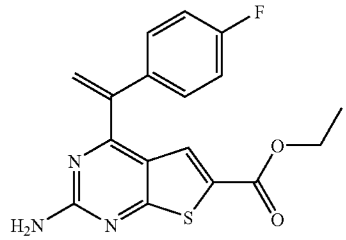 | 344.0 | A | Suzuki |
| 278 | 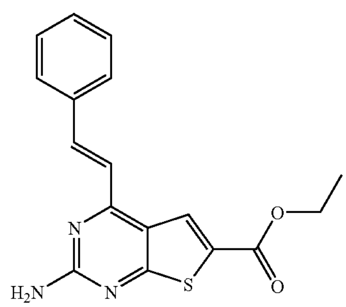 | 326.1 | A | Suzuki |
| 279 | 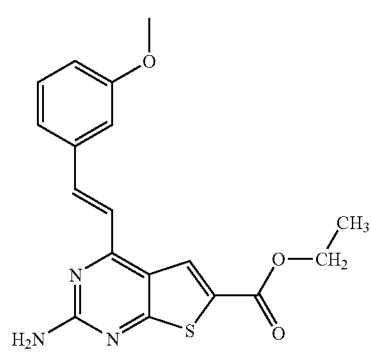 | 356.1 | A | Suzuki |

TABLE 7-continued

| Example | Structure | MH+ | Hsp90 FP IC50 | Synthesis Comment |
|---|---|---|---|---|
| 280 | 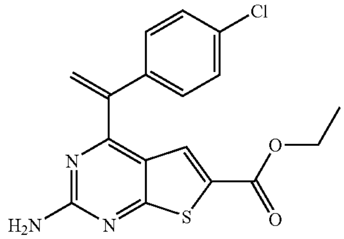 | 360.0 | A | Suzuki |
| 281 | 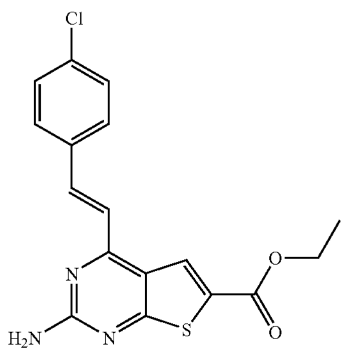 | 360.1 | A | Suzuki |
| 282 | 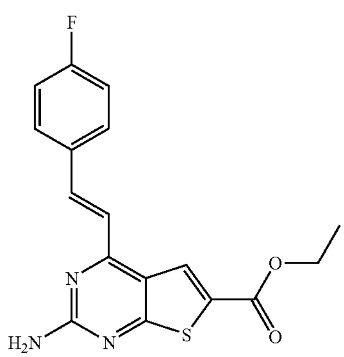 | 344.2 | A | Suzuki |
| 283 | 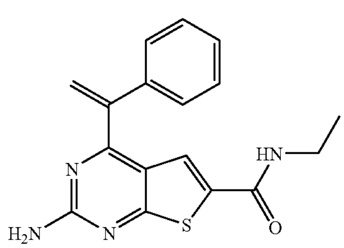 | 325.1 | A | Suzuki hydrolysed then amidation |
| 284 | 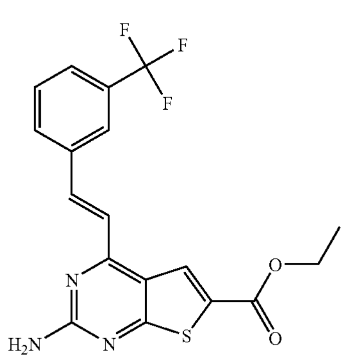 | 393.8 | A | Suzuki |

TABLE 7-continued

| Example | Structure | MH+ | Hsp90 FP IC50 | Synthesis Comment |
|---|---|---|---|---|
| 285 | 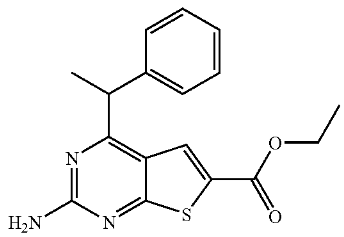 | 328.09 | A | Suzuki then Hydrogenation |
| 286 | 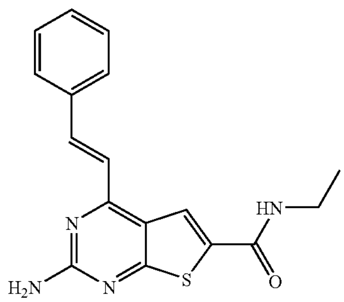 | 325.0 | A | Suzuki then amidation |
| 287 | 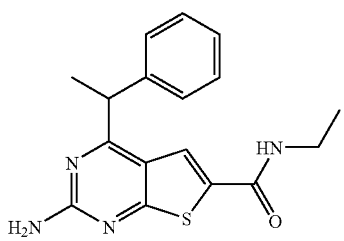 | 327.1 | A | Suzuki, Hydrogenation then amidation |
| 288 | 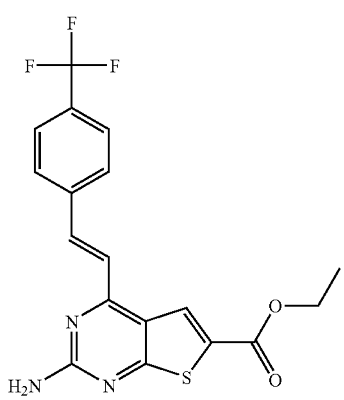 | 394.1 | A | Suzuki |
| 289 | 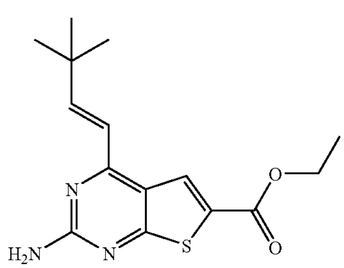 | 306.2 | B | Suzuki |

TABLE 7-continued
| Example | Structure | MH+ | Hsp90 FP IC50 | Synthesis Comment |
|---|---|---|---|---|
| 290 | 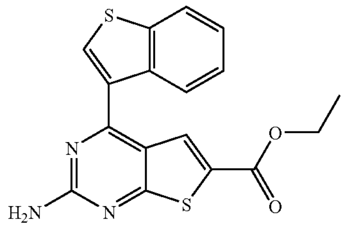 | 355.8 | B | Suzuki |
| 291 | 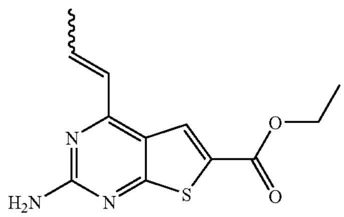 | 264.1 | B | Suzuki |
| 292 | 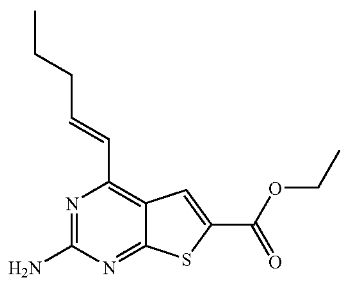 | 292.1 | B | Suzuki |
| 293 | 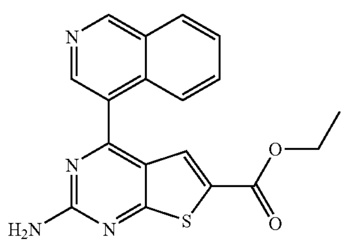 | 351.1 | A | Suzuki |
EXAMPLE 294
2-Amino-4-(1H-indol-3-yl)-thieno[2,3-d]pyrimidine-6-carboxylic acid ethyl ester
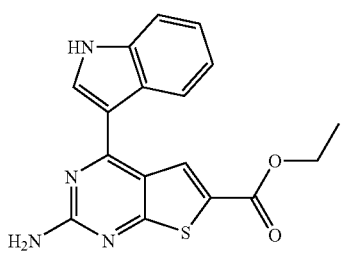
Step 1
2-Amino-4-(1-benzenesulfonyl-1H-indol-3-yl)-thieno[2,3-d]pyrimidine-6-carboxylic acid ethyl ester
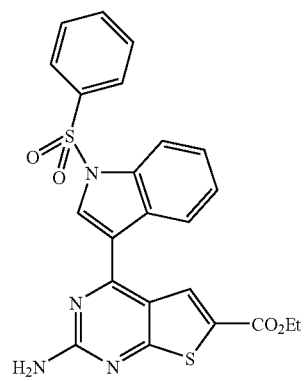

Using 1-(phenylsulfonyl)-3-indole botonic acid and method of Example 275 step 1, the desired product was synthesised as an orange solid (105 g, 29%).

LCMS retention time 7.72 min, [M+H]$^+$=478. (run time 15 mins)

Step 2

2-Amino-4-(1H-indol-3-yl)-thieno[2,3-d]pyrimidine-6-carboxylic acid

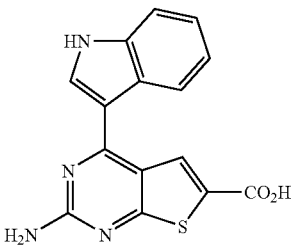

A solution of 2-amino-4-(1-benzenesulfonyl-1H-indol-3-yl)-thieno[2,3-d]pyrimidine-6-carboxylic acid ethyl ester (80 mg, 0.17 mmol) in ethanol (6 ml) was heated to 65° C., 2M potassium hydroxide added (0.25 ml, 3 equiv.) and stirred overnight. Water was added and the volatile removed in vacuo. The solution was then neutralised and freeze dried.

LCMS retention time 5.72 min, [M+H]$^+$=311.07 (run time 15 minutes)

Step 3

2-Amino-4-(1H-indol-3-yl)-thieno[2,3-d]pyrimidine-6-carboxylic acid ethyl ester

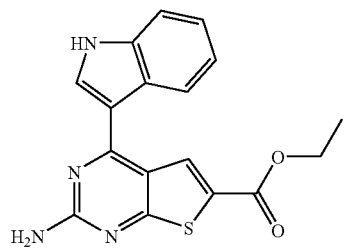

The crude 2-amino-4-(1H-indol-3-yl)-thieno[2,3-d]pyrimidine-6-carboxylic acid was dissolved in ethanol (2 ml) and conc. sulphuric acid was added (5 drops). The solution was refluxed overnight before water was added and the volatiles were removed in vacuo. The aqueous solution was partitioned with 1M sodium hydrogen carbonate solution and ethyl acetate. The organics were combined, dried over sodium sulphate and evaporated to dryness. The pure compounds was obtained after preparative TLC as an off white coloured powder.

$^1$H NMR (d$_6$-DMSO) δ=11.93 (1H, broad s); 8.62 (1H, d, J=7.5 Hz); 8.43 (1H, s); 8.27 (1H, s); 7.53 (1H, d, J=7.5 Hz); 7.27-7.15 (1H+1H+2H, m); 4.34 (2H, q, J=7.1 Hz) and 1.34 (3H, t, J=7.1 Hz).

LCMS retention time 6.70 min, [M+H]$^+$=339.08 (run time 15 minutes)

This compound had activity 'B' in the fluorescence polarization assay described below.

EXAMPLE 294

2-Amino-4-benzyloxy-thieno[2,3-d]pyrimidine-6-carboxylic acid ethylamide

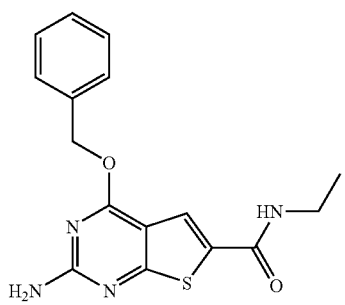

Step 1

2-Amino-4-benzyloxy-thieno[2,3-d]pyrimidine-6-carboxylic acid

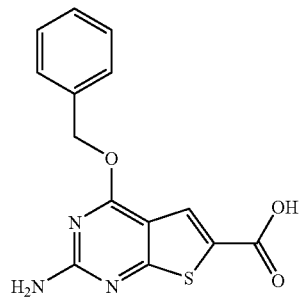

To a nitrogen filled flask containing sodium hydride (0.5 mmol, 60% in mineral oil) in anhydrous THF (5 ml) was added benzyl alcohol (0.5 mmol). The suspension was stirred vigorously for 10 minutes until no more gas was evolved before being transferred to a microwave reaction tube containing 2-amino-4-chloro-thieno[2,3-d]pyrimidine-6-carboxylic acid ethyl ester (0.129 g, 0.5 mmol). The sealed tube was heated to 90° C. for 5 mins using 300 W in a CEM microwave apparatus (CARE!). The reaction mixture was partitioned between DCM and water, the water layer neutralised and evaporated to dryness in vacuo to leave the pure product.

LCMS retention time 6.35 min, [M+H]$^+$=301.93 (run time 15 minutes)

Step 2

2-Amino-4-benzyloxy-thieno[2,3-d]pyrimidine-6-carboxylic acid ethylamide

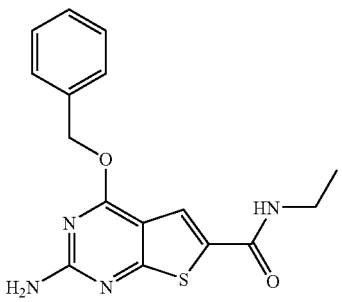

The amide was synthesised using the HATU coupling conditions given in example 43, step 2 and purified by column chromatography.

$^1$H NMR (CDCl$_3$) δ=7.49 (1H, s); 7.39-7.25 (5H, m); 6.03 (1H, broad t, J=5 Hz); 5.39 (2H, s); 5.15 (2H, broad s); 3.38 (2H, dq, J=5.7 Hz and J=7.2 Hz); 1.14 (3H, t, J=7.2 Hz).

LCMS retention time 6.34 min, [M+H]$^+$=329.05 (run time 15 minutes)

This compound had activity 'B' in the fluorescence polarization assay described below.

EXAMPLE 295

2-Amino-4-(4-chloro-benzoyl)-thieno[2,3-d]pyrimidine-6-carboxylic acid ethyl ester

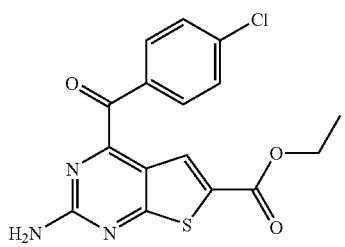

To a solution of 2-amino-4-chloro-thieno[2,3-d]pyrimidine-6-carboxylic acid ethyl ester (1 mole eq.), p-chlorobenzaldehyde (1 mole eq.) and 3-ethyl-1-methyl-3H-imidazol-1-ium bromide (0.3 mole eq.) in DMF at room temperature, sodium hydride (1.1 mole eq., 60% in mineral oil) was added. The solution turned dark immediately and was stirred for 3 hours during which it turned to an orange solution. This was filtered through a sinter glass funnel, brine added and the resulting precipitate was filtered and dried. The resulting yellow solids were purified either by preparative TLC or preparative HPLC $^1$H NMR (d$_6$-acetone) δ=8.11 (2H, d, J=8.8 Hz); 8.03 (1H, s); 7.57 (2H, d, J=8.8 Hz); 6.86 (2H, s); 4.33 (2H, q, J=7.0 Hz) and 1.34 (3H, t, J=7.0 Hz).

LCMS retention time 7.49 min, [M+H]$^+$=362.06 (run time 15 minutes)

This compound had activity 'A' in the fluorescence polarization assay described below.

The following compounds (Table 8) were made by the method of Example 295 substituting the appropriate benzaldehyde. The fourth column of Table 8 states the activity of the compound in the fluorescence polarization assay described below.

TABLE 8

| Example | Structure | MH+ | Hsp90 FP IC50 | Synthesis Comment |
|---|---|---|---|---|
| 296 | 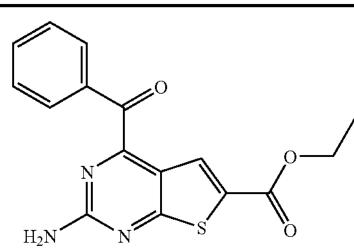 | 328.0 | A | Aroylation |
| 297 | 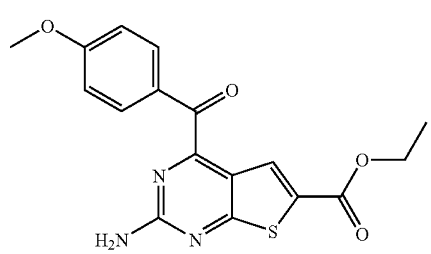 | 358.1 | A | Aroylation |

TABLE 8-continued

| Example | Structure | MH+ | Hsp90 FP IC50 | Synthesis Comment |
|---|---|---|---|---|
| 298 | 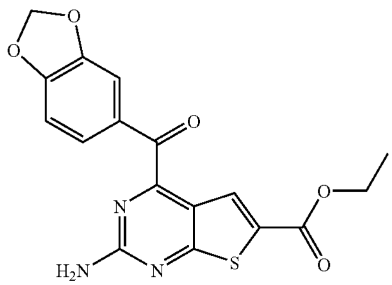 | 372.0 | A | Aroylation |
| 299 | 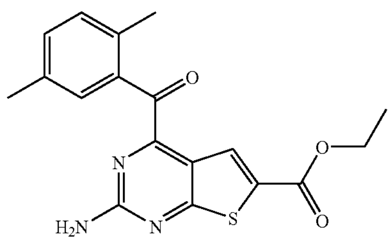 | 356.1 | A | Aroylation |
| 300 | 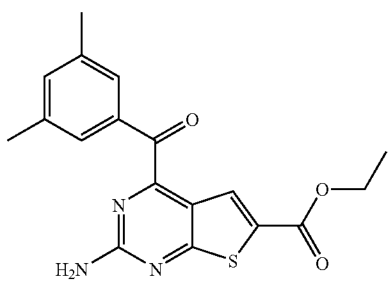 | 356.1 | A | Aroylation |
| 301 | 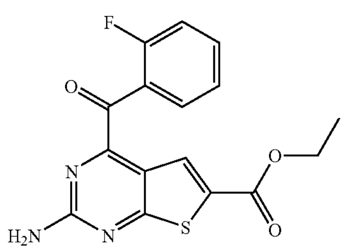 | 346.0 | A | Aroylation |
| 302 | 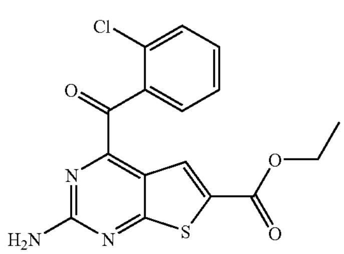 | 362.0 | A | Aroylation |

TABLE 8-continued

| Example | Structure | MH+ | Hsp90 FP IC50 | Synthesis Comment |
|---------|-----------|-----|---------------|-------------------|
| 303 | 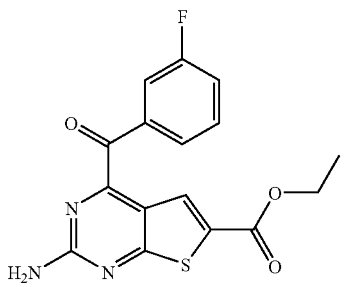 | 346.0 | A | Aroylation |
| 304 | 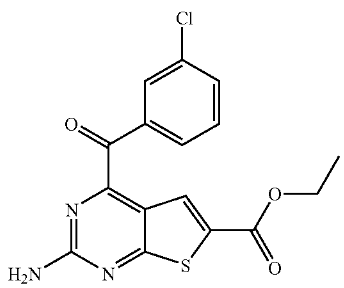 | 362.1 | A | Aroylation |
| 305 | 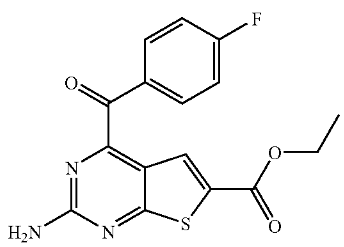 | 346.0 | A | Aroylation |
| 306 | 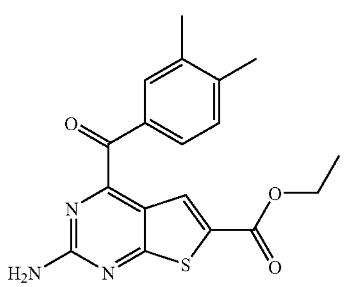 | 356.1 | A | Aroylation |
| 307 | 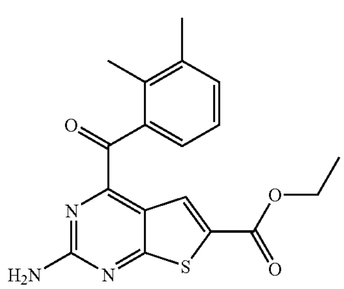 | 356.1 | A | Aroylation |

TABLE 8-continued

| Example | Structure | MH+ | Hsp90 FP IC50 | Synthesis Comment |
|---|---|---|---|---|
| 308 | 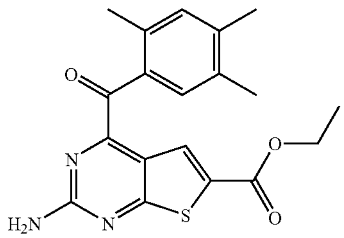 | 370.1 | A | Aroylation |
| 309 | 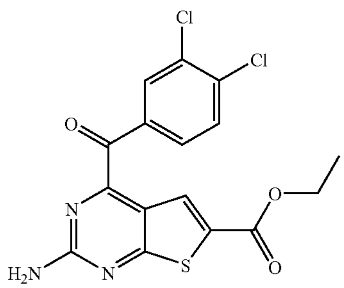 | 396.0 | A | Aroylation |
| 310 | 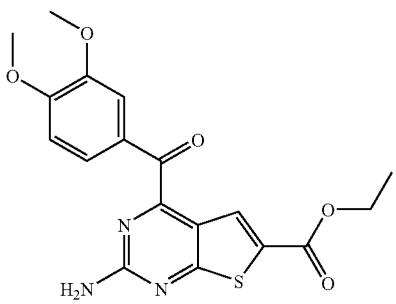 | 388.1 | A | Aroylation |
| 311 | 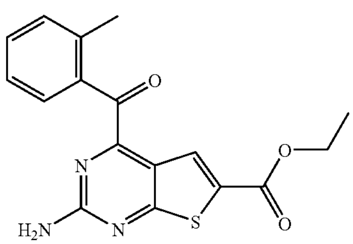 | 342.1 | A | Aroylation |
| 312 | 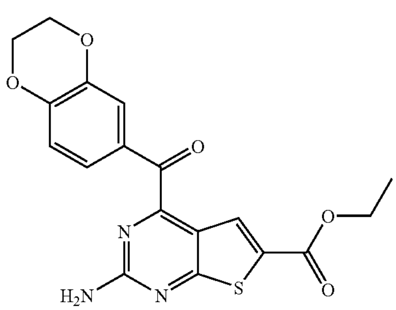 | 386.1 | A | Aroylation |

TABLE 8-continued

| Example | Structure | MH+ | Hsp90 FP IC50 | Synthesis Comment |
|---------|-----------|-----|---------------|-------------------|
| 313 | 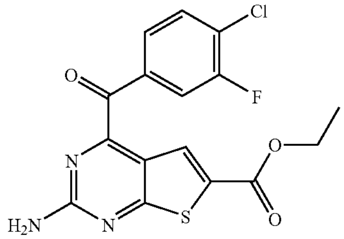 | 380.0 | A | Aroylation |
| 314 | 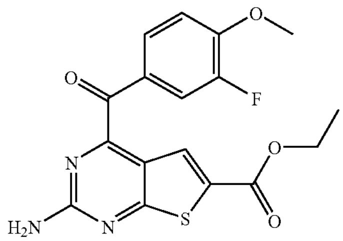 | 376.1 | A | Aroylation |

EXAMPLE 315

2-Amino-4-(1-benzo[1,3]dioxol-5-yl-1-hydroxy-ethyl)-thieno[2,3-d]pyrimidine-6-carboxylic acid ethyl ester

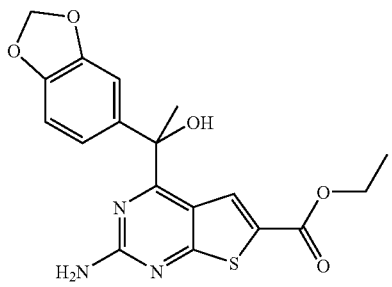

2-Amino-4-(benzo[1,3]dioxole-5-carbonyl)-thieno[2,3-d]pyrimidine-6-carboxylic acid ethyl ester (example 312) (100 mg) was dissolved in anhydrous THF under a nitrogen atmosphere before methyl magnesium bromide (3.0M solution in diethyl ether, 5 equiv.) was added. The solution was stirred at 40° C. overnight before being partitioned between 10% aqueous ammonium chloride solution and ethyl acetate. The organic layer was washed with brine, dried over magnesium sulphate and evaporated to yield a crude product that was purified by preparative TLC to give the desired compound as a yellow powder.

$^1$H NMR (d$_6$-acetone) δ=8.04 (1H, s); 6.94 (1H, d, J=7.7 Hz); 6.91 (1H, s); 6.64 (1H, d, J=7.7 Hz); 6.50 (2H, broad s); 5.81 (2H, s); 5.46 (1H, s); 4.17 (2H, q, J=7.1 Hz); 1.81 (3H, s) and 1.19 (3H, t, J=7.1 Hz).

LCMS retention time 6.37 min, (elimination of H$_2$O in LCMS) [M+H]$^+$=370.07 (run time 15 minutes).

This compound had activity 'A' in the fluorescence polarization assay described below.

EXAMPLE 316

2-Amino-4-(benzo[1,3]dioxol-5-yl-cyano-methyl)-thieno[2,3-d]pyrimidine-6-carboxylic acid ethyl ester

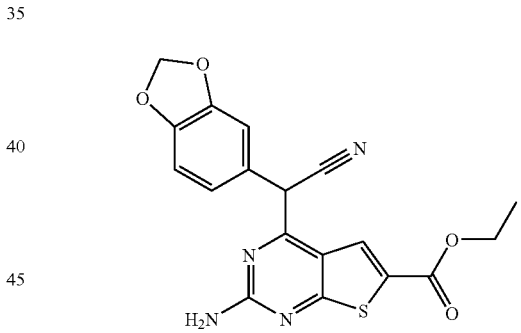

To a solution of 2-amino-4-chloro-thieno[2,3-d]pyrimidine-6-carboxylic acid ethyl ester (1 equiv.) and benzo[1,3]dioxol-5-yl-acetonitrile (1 mole eq.) in DMF at room temperature, sodium hydride (1.1 mole eq., 60% in mineral oil) was added. The mixture was stirred at this temperature overnight under argon. After that, it was diluted with brine and extracted with ethyl acetate. The combined organic portions were washed with brine and water and dried with sodium sulphate. After filtration and evaporation of the solvent, brown solids were obtained which were purified either by preparative TLC or preparative HPLC.

$^1$H NMR (d$_6$-acetone) δ=7.76 (1H, s); 6.84 (1H, d, J=8.0 Hz); 6.56 (1H+1H+1H, m); 6.10 (1H, d, J=1.0 Hz); 6.05 (1H, d, J=1.0 Hz); 4.30 (2H, q, J=7.0 Hz) and 1.30 (3H, t, J=7.0 Hz).

LCMS retention time 7.04 min, [M+H]$^+$=383.06 (run time 15 minutes)

This compound had activity 'A' in the fluorescence polarization assay described below.

The following compounds (Table 9) were made by the method of Example 316 substituting the appropriate acetonitrile. The fourth column of Table 9 states the activity of the compound in the fluorescence polarization assay described below.

solution, where the larger molecule the more polarized the fluorescence emission. When the fluorophore is excited with polarized light, the emitted light is also polarized. The molecular size is proportional to the polarization of the fluorescence emission.

TABLE 9

| Example | Structure | MH+ | Hsp90 FP IC50 | Synthesis Comment |
|---|---|---|---|---|
| 317 | 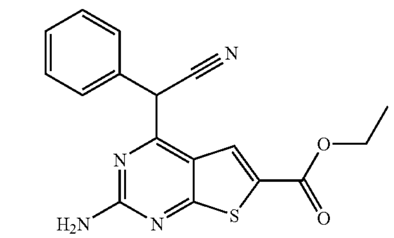 | 339.1 | A | Chloride displacement |
| 318 | 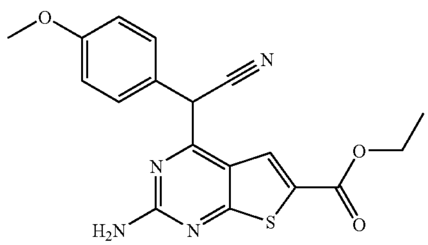 | 369.1 | B | Chloride displacement |

EXAMPLE 319

2-Amino-4-cyano-thieno[2,3-d]pyrimidine-6-carboxylic acid ethyl ester

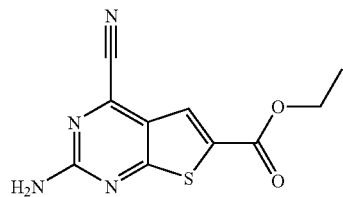

2-Amino-4-chloro-thieno[2,3-d]pyrimidine-6-carboxylic acid ethyl ester (1 equiv.), $Zn(CN)_2$ (0.6 equiv.), Zn dust (0.12 equiv.), $Pd_2(dba)_3$ (0.02 mole eq.) and 1,1'-bis(diphenylphosphino)ferrocene (0.04 equiv.) were mixed in DMA and the mixture was stirred under argon at 120° C. for 24 hours. The resulting suspension was filtered through a short Celite column, the filtrate was diluted with brine and extracted with ethyl acetate. The organic layer was then washed with brine, water and dried over sodium sulphate. After evaporation of the solvent, the crude oil was purified by preparative TLC.

$^1$H NMR ($d_6$-acetone) δ=7.92 (1H, s); 7.08 (1H, s); 4.42 (2H, q, J=7.0 Hz) and 1.40 (3H, t, J=7.0 Hz).

LCMS retention time 6.10 min [M+H]+=249.04 (run time 15 minutes)

This compound had activity 'A' in the fluorescence polarization assay described below.

Fluorescence Polarization Assay

Fluorescence polarization {also known as fluorescence anisotropy} measures the rotation of a fluorescing species in The fluoroscein-labelled probe—RBT0045864-FAM—

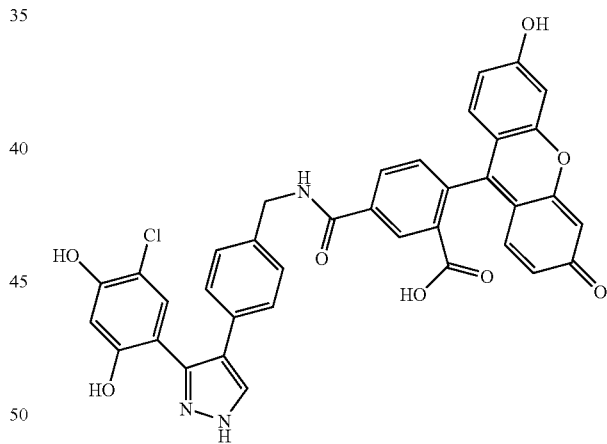

binds to HSP90 {full-length human, full-length yeast or N-terminal domain HSP90} and the anisotropy {rotation of the probe:protein complex} is measured.

Test compound is added to the assay plate, left to equilibrate and the anisotropy measured again. Any change in anisotropy is due to competitive binding of compound to HSP90, thereby releasing probe.

Materials

Chemicals are of the highest purity commercially available and all aqueous solutions are made up in AR water.

1) Costar 96-well black assay plate #3915
2) Assay buffer of (a) 100 mM Tris pH7.4; (b) 20 mM KCl; (c) 6 mM $MgCl_2$. Stored at room temperature.

3) BSA (bovine serum albumen) 10 mg/ml (New England Biolabs # B9001S)
4) 20 mM probe in 100% DMSO stock concentration. Stored in the dark at RT. Working concentration is 200 nM diluted in AR water and stored at 4° C. Final concentration in assay 80 nM.
5) E. coli expressed human full-length HSP90 protein, purified >95% (see, e.g., Panaretou et al., 1998) and stored in 50 μL aliquots at −80° C.

Protocol
1) Add 100 μl 1× buffer to wells 11A and 12A (=FP BLNK)
2) Prepare assay mix—all reagents are kept on ice with a lid on the bucket as the probe is light-sensitive.

|  | i. Final Conc$^n$ |  |
| --- | --- | --- |
| 1× Hsp90 FP Buffer | 10 ml | 1× |
| BSA 10 mg/ml (NEB) | 5.0 μl | 5 μg/ml |
| Probe 200 μM | 4.0 μl | 80 nM |
| Human full-length Hsp90 | 6.25 μl | 200 nM |

3) Aliquot 100 μl assay mix to all other wells
4) Seal plate and leave in dark at room temp for 20 minutes to equilibrate Compound Dilution Plate—1×3 Dilution Series
1) In a clear 96-well v-bottom plate—{# VWR 007/008/257} add 10 μl 100% DMSO to wells B1 to H11
2) To wells A1 to A11 add 17.5 μl 100% DMSO
3) Add 2.5 μl cpd to A1. This gives 2.5 mM {50×} stock cpd—assuming cpds 20 mM.
4) Repeat for wells A2 to A10. Control in columns 11 and 12.
5) Transfer 5 μl from row A to row B—not column 12. Mix well.
6) Transfer 5 μl from row B to row C. Mix well.
7) Repeat to row G.
8) Do not add any compound to row H—this is the 0 row.
9) This produces a 1×3 dilution series from 50 μM to 0.07 μM.
10) In well B12 prepare 20 μl of 100 μM standard compound.
11) After first incubation the assay plate is read on a Fusion™ α-FP plate reader (Packard BioScience, Pangbourne, Berkshire, UK).
12) After the first read, 2 μl of diluted compound is added to each well for columns 1 to 10. In column 11 {provides standard curve} only add compound B11-H11. Add 2 μl of 100 mM standard cpd to wells B12-H12 {is positive control}
13) The Z' factor is calculated from zero controls and positive wells. It typically gives a value of 0.7-0.9.

The compounds tested in the above assay were assigned to one of two activity ranges, namely A=<10 μM; B=>10 μM, and those assignments are reported above.

A growth inhibition assay was also employed for the evaluation of candidate HSP90 inhibitors:

Assessment of Cytotoxicity by Sulforhodamine B (SRB) Assay: Calculation of 50% Inhibitory Concentration ($IC_{50}$).

Day 1
1) Determine cell number by haemocytometer.
2) Using an 8 channel multipipettor, add 1601 μl of the cell suspension (3600 cells/well or $2 \times 10^4$ cells/ml) to each well of a 96-well microtitre plate.
3) Incubate overnight at 37° C. in a $CO_2$ incubator.

Day 2
4) Stock solutions of drugs are prepared, and serial dilutions of each drug are performed in medium to give final concentrations in wells.
5) Using a multipipettor, 40 μl of drug (at 5× final concentration) is added to quadruplicate wells.
6) Control wells are at either side of the 96 well plates, where 40 μl of medium is added.
7) Incubate plates in $CO_2$ incubator for 4 days (48 hours).

Day 6
8) Tip off medium into sink and immerse plate slowly into 10% ice cold trichloroacetic acid (TCA). Leave for about 30 mins on ice.
9) Wash plates three times in tap water by immersing the plates into baths of tap water and tipping it off.
10) Dry in incubator.
11) Add 100 μl of 0.4% SRB in 1% acetic acid to each well (except the last row (right hand) of the 96 well plate, this is the 0% control, ie no drug, no stain. The first row will be the 100% control with no drug, but with stain). Leave for 15 mins.
12) Wash off unbound SRB stain with four washes of 1% acetic acid.
13) Dry plates in incubator.
14) Solubilise SRB using 100 μl of 10 mM Tris base and put plates on plate shaker for 5 mins.
15) Determine absorbance at 540 nm using a plate reader. Calculate mean absorbance for quadruplicate wells and express as a percentage of value for control, untreated wells.
16) Plot % absorbance values versus log drug concentration and determine the $IC_{50}$.

By way of illustration, the compound of Example 2 gave an IC50 in the 'A' range (<50 uM) for the SRB growth arrest assay.

REFERENCES

A number of publications are cited above in order to more fully describe and disclose the invention and the state of the art to which the invention pertains. Full citations for these references are provided below. Each of these references is incorporated herein by reference in its entirety into the present disclosure.

Argon Y and Simen B B. 1999 "Grp94, an ER chaperone with protein and peptide binding properties", *Semin. Cell Dev. Biol.*, Vol. 10, pp. 495-505.

Bijlmakers M-J J E, Marsh M. 2000 "Hsp90 is essential for the synthesis and subsequent membrane association, but not the maintenance, of the Src-kinase p56lck", *Molecular Biology of the Cell*, Vol. 11 (5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", *Brit. J. Pharmacol.*, Vol 131(1), pp. 13-16.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", *Mol. Cell. Biol.*, Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289-299.

Conroy S E and Latchman D S. 1996 "Do heat shock proteins have a role in breast cancer?", *Brit. J. Cancer*, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilizes delta F508 CFTR in the rabbit reticulocyte lysate", *J. Biol. Chem.*; Vol 275(48), pp. 37462-37468.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.*, Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res.*, Vol. 61, pp. 4003-4009.

Hur E, Kim H-H, Choi S M, Kim J H, Yim S, Kwon H J, Choi Y, Kim D K, Lee M-O, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", *Mol. Pharmacol.*, Vol 62(5), pp. 975-982.

Hutter et al, 1996, *Circulation*, Vol. 94, pp. 1408.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409-415.

Jolly C and Morimoto R I. 2000 "Role of the heat shock response and molecular chaperones in oncogenesis and cell death", *J. Natl. Cancer Inst.*, Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp. 1649-1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", *Jap. J. Cancer Res.*, Vol 92(12), 1342-1351.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem.*, Vol. 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp. 1125-1132.

Marcu M G, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181-37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232-2238.

Neckers L, Schulte T W and Momnaaugh E. 1999 "Geldanamycin as a potential anti-cancer agent: its molecular target and biochemical activity", *Invest. New Drugs*, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J.*, Vol. 17, pp. 4829-4836.

Plumier et al, 1997, *Cell. Stress Chap.*, Vol. 2, pp. 162

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297-326.

Prodromou C and Pearl L H. 2000a "Structure and in vivo function of HSP90", *Curr. Opin. Struct. Biol.*, Vol. 10, pp. 46-51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65-75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.*, Vol. 19, pp. 4383-4392.

Rajder et al, 2000, *Ann. Neurol.*, Vol. 47, pp. 782.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp. 260-266.

Rutherford S L and Lindquist S. 1998 "HSP90 as a capacitor for morphological evolution. *Nature*, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp. 100-108.

Schulte T W and Neckers L M. 1998 "The benzoquinone ansamycin 17-allylamino-17-deemthoxygeldanamcyin binds to HSP90 and shares important biologic activities with geldanamycin", *Cancer Chemother. Pharmacol.*, Vol. 42, pp. 273-279.

Sittler et al, 2001, *Hum. Mol. Genet.*, Vol. 10, pp. 1307.

Smith D F. 2001 "Chaperones in signal transduction", in: *Molecular chaperones in the cell* (P Lund, ed.; Oxford University Press, Oxford and NY), pp. 165-178.

Smith D F, Whitesell L and Katsanis E. 1998 "Molecular chaperones: Biology and prospects for pharmacological intervention", *Pharmacological Reviews*, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", *J. Biol. Chem.*, Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", *Cell*, Vol. 89, pp. 239-250.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305-315.

Tratzelt et al, 1995, *Proc. Nat. Acad. Sci.*, Vol. 92, pp. 2944.

Trost et al, 1998, *J. Clin. Invest.*, Vol. 101, pp. 855.

Tytell M and Hooper P L. 2001 "Heat shock proteins: new keys to the development of cytoprotective therapies", *Emerging Therapeutic Targets*, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198-2206.

Waxman, Lloyd H. Inhibiting hepatitis C virus processing and replication. (Merck & Co., Inc., USA). PCT Int. Appl. (2002), WO 0207761

Winklhofer et al, 2001, *J. Biol. Chem.*, Vol. 276, 45160.

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. USA.*, Vol. 91, pp. 8324-8328.

Yorgin et al. 2000 "Effects of geldanamycin, a heat-shock protein 90-binding agent, on T cell function and T cell nonreceptor protein tyrosine kinases", *J. Immunol.*, Vol 164(6), pp. 2915-2923.

Young J C, Moarefi I and Hartl F U. 2001 "HSP90: a specialized but essential protein-folding tool", *J. Cell. Biol.*, Vol. 154, pp. 267-273.

Zhao J F, Nakano H and Sharma S. 1995 "Suppression of RAS and MOS transformation by radicicol", *Oncogene*, Vol. 11, pp. 161-173.

The invention claimed is:

1. A compound of formula (I), or a salt or N-oxide thereof:

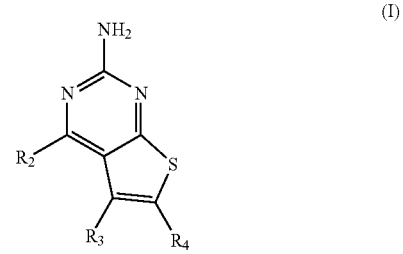

(I)

wherein
R$_2$ is a group of formula (IA):

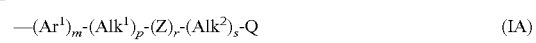

(IA)

wherein
Ar$^1$ is an optionally substituted aryl or heteroaryl radical,
Alk$^1$ and Alk$^2$ are optionally substituted divalent C$_1$-C$_3$ alkylene or C$_2$-C$_3$ alkenylene radicals,
m, p, r and s are independently 0 or 1,
Z is —O—, —S—, —(C=O)—, —(C=S)—, —SO$_2$—, —C(=O)O—, —C(=O)NR$^A$—, —C(=S)NR$^A$—, —SO$_2$NR$^A$—, —NR$^A$C(=O)—, —NR$^A$SO$_2$— or —NR$^A$— wherein R$^A$ is hydrogen or C$_1$-C$_6$ alkyl, and
Q is hydrogen or an optionally substituted carbocyclic or heterocyclic radical;
R$_3$ is hydrogen, an optional substituent, or an optionally substituted (C$_1$-C$_6$)alkyl, aryl or heteroaryl radical; and
R$_4$ is a carboxylic ester, carboxamide or sulfonamide group,
wherein when optionally substituted, substituent(s) is/are selected from the group consisting of (C$_1$-C$_6$)alkyl, (C$_1$-C$_6$)alkoxy, hydroxy, hydroxy(C$_1$-C$_6$)alkyl, mercapto, mercapto(C$_1$-C$_6$)alkyl, (C$_1$-C$_6$)alkylthio, halo, trifluoromethyl, trifluoromethoxy, nitro, nitrile (—CN), oxo, phenyl, —COOH, —COO R$^F$, —CO R$^F$, —SO$_2$R$^F$, —CONH$_2$, —SO$_2$NH$_2$, —CONHR$^F$, —SO$_2$NHR$^F$, —CONR$^F$R$^G$, —SO$_2$NR$^F$R$^G$, —NH$_2$, —NHR$^F$, —NR$^F$R$^G$, —OCONH$_2$, —OCONHR$^F$, —OCONR$^F$R$^G$, —NHCOR$^F$, —NHCOOR$^F$, —NR$^F$COOR$^F$, —NHSO$_2$OR$^F$, NR$^G$SO$_2$OR$^F$, —NHCONH$_2$, —NR$^F$CONH$_2$, —NHCONHR$^G$, —NR$^F$CONHR$^G$, —NHCONR$^F$R$^G$, or —NR$^F$CONR$^F$R$^G$ wherein R$^F$ and R$^G$ are independently a (C$_1$-C$_6$)alkyl group;
provided that (i) R$_3$ is not —NH$_2$ and (ii) when R$_4$ is —COOCH$_3$ and R$_3$ is hydrogen then R$_2$ is not —NH$_2$, ethylamino, diethylamino, phenylamino, N(Ph)(C$_2$H$_5$) wherein Ph is phenyl, pyrrolidin—1—yl or morpholin—4—yl and (iii) when R$_4$ is —CONH$_2$ and R$_3$ is hydrogen then R$_2$ is not —NH$_2$.

2. A compound as claimed in claim 1 wherein R$_3$ is hydrogen.

3. A compound as claimed in claim 1 wherein m is 1, each of p, r and s is 0, and Q is hydrogen.

4. A compound as claimed in claim 3 wherein R$_2$ is optionally substituted phenyl, 2- or 3-thienyl, 2- or 3- furanyl, 2-, 3- or 4-pyridinyl, morpholinyl, or piperidinyl.

5. A compound as claimed in claim 3 wherein R$_2$ is phenyl, optionally substituted by methyl, ethyl, n- or isopropyl, vinyl, allyl, methoxy, ethoxy, n-propyloxy, benzyloxy, allyloxy, cyanomethoxy, chloro, bromo, cyano, formyl, methyl-, ethyl-, or n-propyl-carbonyloxy, methyl- or ethylaminocarbonyl.

6. A compound as claimed in claim 5 wherein optional substituents are in the 2- and/or 4- and/or 5-position of the phenyl ring.

7. A compound as claimed in claim 1 wherein m is 1, and p, r and s are 0, and Q is an optionally substituted carbocyclic or heterocyclic ring.

8. A compound as claimed in claim 1 wherein m is 1 and at least one of p, r and s is 1.

9. A compound as claimed in claim 1 wherein $Ar^1$ is an optionally substituted phenyl ring.

10. A compound as claimed in claim 1 wherein m is 0.

11. A compound as claimed in claim 8 wherein $Alk^1$ when present is optionally substituted —$CH_2$, $CH_2CH_2$— or —CH=CH—; $Alk^2$ when present is optionally substituted —$CH_2$, $CH_2CH_2$— or —CH=CH—; Z when present is —O—or —NH—; and Q is hydrogen.

12. A compound as claimed in claim 11 wherein Z and $Alk^2$ are present, and $Alk^2$ is substituted by di($C_1$-$C_3$alkyl)amino or $C_1$-$C_3$alkoxy.

13. A compound as claimed in claim 1 wherein $R_4$ is a carboxamide group of formula —$CONR^B(Alk)_nR^D$or a sulphonamide group of formula —$SO_2NR^B(Alk)_nR^D$wherein Alk is an optionally substituted divalent alkylene, alkenylene or alkynylene radical, n is 0 or 1, $R^B$ is hydrogen or a $C_1$-$C_6$ alkyl or $C_2$-$C_6$ alkenyl group, —$R^D$ is hydroxy or optionally substituted carbocyclic, or heterocyclyl, any of which heterocyclic rings may be substituted, or —$R^D$ and $R^B$ taken together with the nitrogen to which they are attached form an N-heterocyclic ring which may optionally contain one or more additional hetero atoms selected from O, S and N, and which may be optionally substituted on one or more ring C or N atoms: wherein optionally substituted is as defined in claim 1.

14. A compound as claimed in claim 13 wherein

Alk is optionally substituted —$CH_2$—, —$CH_2CH_2$—, —$CH_2CH_2CH_2$—, —$CH_2CH=CH$—, or —$CH_2CCCH_2$—, $R^B$ is hydrogen or methyl, ethyl, n- or iso-propyl, or allyl, —$R^D$ is hydroxy or optionally substituted phenyl, 3,4 methylenedioxyphenyl, pyridyl, furyl, thienyl, N-piperazinyl, or N-morpholinyl, or —$R^D$ and $R^B$ taken together with the nitrogen to which they are attached form an N-heterocyclic ring which may optionally contain one or more additional hetero atoms selected from O, S and N, and which may be optionally substituted on one or more ring C or N atoms: wherein optionally substituted is as defined in claim 13.

15. A compound as claimed in claim 13 wherein $R_4$ is the carboxamide group of formula —$CONR^B(Alk)_nR^D$.

16. A compound as claimed in claim 1 wherein $R_4$ is a carboxylic ester group of formula —$COOR^C$ wherein $R^C$ is a $C_1$-$C_6$ alkyl or $C_2$-$C_6$ alkenyl group, or an optionally substituted aryl or heteroaryl group, or an optionally substituted aryl($C_1$-$C_6$ alkyl)- or heteroaryl($C_1$-$C_6$ alkyl)- group or an optionally substituted cycloalkyl group: wherein optionally substituted is as defined in claim 1.

17. A compound as claimed in claim 1 wherein $R_4$ is a carboxylic ester group of formula —$COOR^C$ wherein $R^C$ is optionally substituted methyl, ethyl, n- or iso- propyl, allyl, phenyl, pyridyl, thiazolyl, benzyl, pyridylmethyl, cyclopentyl or cyclohexyl;

wherein optionally substituted is as defined in claim 1.

18. A compound as claimed in claim 1 having formula (II):

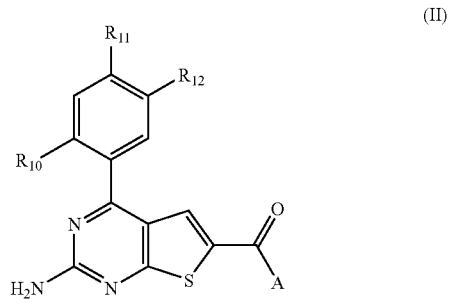

(II)

wherein
A is a secondary amino group
$R_{10}$ is H, Cl, Br, or $CH_3$;
$R_{11}$ is hydrogen, Cl, Br, CN, methyl, ethyl, n- or iso-propyl, vinyl or allyl;
$R_{12}$ is (i) a radical of formula —$O(CH_2)_nZ^1$ wherein n is 1, 2 or 3 and $Z^1$ is a primary, secondary, tertiary or cyclic amino group, or a $C_1$-$C_6$alkoxy group; or (ii) a radical of formula -$(Alk^3)_mZ^1$ wherein $Alk^3$ is a divalent straight or branched chain ($C_1$-$C_3$) alkylene, m is 0 or 1, and $Z^1$ is a primary, secondary, tertiary or cyclic amino group, or a $C_1$-$C_6$alkoxy group.

19. A compound as claimed in claim 18 wherein A is a secondary $C_1$-$C_6$alkylamino group.

20. A compound as claimed in claim 18 wherein $R_{12}$ is (i) a radical of formula —$O(CH_2)_nZ^1$ wherein n is 1, 2 or 3 and $Z^1$ is di($C_1$-$C_3$alkyl)amino or $C_1$-$C_3$ alkoxy.

21. A compound having the structure

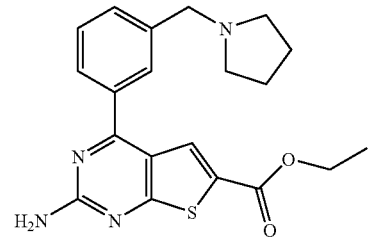

or a salt thereof.

22. A pharmaceutical or veterinary composition comprising a compound as claimed in claim 1, together with one or more pharmaceutically or veterinarily acceptable carriers and/or excipients.

23. A compound as claimed in claim 13 wherein $R^D$ is hydroxyl-substituted phenyl, chloro-substituted phenyl, 3,4-methylenedioxyphenyl, pyridyl, furyl, thienyl, N-piperazinyl, or N-morpholinyl.

* * * * *

UNITED STATES PATENT AND TRADEMARK OFFICE
CERTIFICATE OF CORRECTION

| | | |
|---|---|---|
| PATENT NO. | : 7,820,658 B2 | Page 1 of 1 |
| APPLICATION NO. | : 10/569287 | |
| DATED | : October 26, 2010 | |
| INVENTOR(S) | : Brian William Dymock et al. | |

It is certified that error appears in the above-identified patent and that said Letters Patent is hereby corrected as shown below:

In Column 174, Claim 1, Lines 55-56:
　　Please replace "Ph is phenyl, pyrrolidin—1—yl or morpholin—4—yl and (iii) when $R_4$ is" with --Ph is phenyl, and (iii) when $R_4$ is--

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,820,658 B2 | Page 1 of 1 |
| APPLICATION NO. | : 10/569287 | |
| DATED | : October 26, 2010 | |
| INVENTOR(S) | : Brian William Dymock et al. | |

It is certified that error appears in the above-identified patent and that said Letters Patent is hereby corrected as shown below:

Column 174, Claim 1, Lines 55-56 should read:
"Ph is phenyl, pyrrolidin—1—yl or morphlin—4—yl and (iii) when $R_4$ is"

Signed and Sealed this
Twenty-ninth Day of May, 2012

David J. Kappos
*Director of the United States Patent and Trademark Office*